US012691250B2

(12) United States Patent
Hughett, Sr. et al.

(10) Patent No.: US 12,691,250 B2
(45) Date of Patent: Jul. 28, 2026

(54) INTERMITTENT-CATHETER ASSEMBLIES AND METHODS THEREOF

(71) Applicant: C. R. Bard, Inc., Franklin Lakes, NJ (US)

(72) Inventors: James David Hughett, Sr., Monroe, GA (US); Ronald N. Legaspi, Alpharetta, GA (US); Kyle Daw, Smyrna, GA (US); Steven M. Breen, Decatur, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 451 days.

(21) Appl. No.: 18/019,647

(22) PCT Filed: Jul. 30, 2021

(86) PCT No.: PCT/US2021/044021
§ 371 (c)(1),
(2) Date: Feb. 3, 2023

(87) PCT Pub. No.: WO2022/031550
PCT Pub. Date: Feb. 10, 2022

(65) Prior Publication Data
US 2023/0293849 A1      Sep. 21, 2023

Related U.S. Application Data

(60) Provisional application No. 63/060,627, filed on Aug. 3, 2020.

(51) Int. Cl.
*A61M 25/00*          (2006.01)

(52) U.S. Cl.
CPC ...... *A61M 25/002* (2013.01); *A61M 25/0043* (2013.01); *A61M 2025/0046* (2013.01); *A61M 2025/006* (2013.01)

(58) Field of Classification Search
CPC ............ A61M 25/002; A61M 25/0111; A61M 39/20; A61M 39/162; A61M 25/0017;
(Continued)

(56) References Cited

U.S. PATENT DOCUMENTS

| 426,931 A | 4/1890 | Flower |
| 734,498 A | 7/1903 | Bachler |
| | (Continued) | |

FOREIGN PATENT DOCUMENTS

| AU | 2016283336 A1 | 12/2017 |
| AU | 2014362360 B2 | 1/2020 |
| | (Continued) | |

OTHER PUBLICATIONS

U.S. Appl. No. 13/662,278, filed Oct. 26, 2012 Examiner's Answer dated Jun. 2, 2017.
(Continued)

*Primary Examiner* — Adam Marcetich
(74) *Attorney, Agent, or Firm* — Rutan & Tucker LLP

(57) ABSTRACT

Disclosed are an intermittent-catheter assemblies and packages, carrying cases, and methods thereof. For example, an intermittent-catheter assembly can include an intermittent catheter and a catheter housing. The intermittent catheter can include a proximal piece (106), a cap (110) configured to cap a proximal opening of the proximal piece, and a catheter tube (114) fluidly connected to the proximal piece. The catheter housing can be around at least the catheter tube. The catheter housing can include a distal piece (130) and a collapsible sheath (148). The distal piece can include a lubricating means for lubricating the catheter tube when the distal piece is proximally slid over the catheter tube. The collapsible sheath can include a distal portion (146) coupled to the distal piece and a proximal portion (148) coupled to a neck of the proximal piece. An entirety of the catheter tube
(Continued)

can be disposed in the catheter housing in a packaged state of the intermittent-catheter assembly.

19 Claims, 12 Drawing Sheets

(58) Field of Classification Search
CPC .. A61M 25/0097; A61M 39/16; A61M 39/10; A61M 2207/00; A61M 2210/1089; A61M 25/0113; A61M 39/18; A61M 2025/0681; A61M 2202/0496; A61M 2210/1078; A61M 2210/1096; A61M 39/165; A61M 2039/167
See application file for complete search history.

(56) References Cited

U.S. PATENT DOCUMENTS

| | | | |
|---|---|---|---|
| 1,131,865 A | 3/1915 | Putnam et al. |
| 1,235,142 A | 7/1917 | Ichilian |
| 1,304,396 A | 5/1919 | Smith |
| 1,643,289 A | 9/1927 | Peglay |
| 1,661,494 A | 3/1928 | Nielsen |
| 1,876,229 A | 9/1932 | Oliver et al. |
| 1,888,349 A | 11/1932 | Jacoby |
| 1,978,497 A | 10/1934 | Lind |
| 2,043,630 A | 6/1936 | Raiche |
| 2,213,210 A | 9/1940 | Egbert |
| 2,228,992 A | 1/1941 | Fry |
| 2,230,226 A | 2/1941 | Auzin |
| 2,248,934 A | 7/1941 | Auzin |
| 2,262,749 A | 11/1941 | Berwald |
| 2,285,502 A | 6/1942 | Dreyfus |
| 2,308,484 A | 1/1943 | Auzin et al. |
| 2,314,262 A | 3/1943 | Winder |
| 2,320,157 A | 5/1943 | Raiche |
| 2,322,858 A | 6/1943 | Limbert et al. |
| 2,330,399 A | 9/1943 | Winder |
| 2,330,400 A | 9/1943 | Winder |
| 2,389,831 A | 11/1945 | Welsh |
| 2,390,070 A | 12/1945 | Auzin |
| 2,481,488 A | 9/1949 | Auzin |
| 2,494,393 A | 1/1950 | Lamson |
| 2,610,626 A | 9/1952 | Edwards |
| 2,638,093 A | 5/1953 | Kulick |
| 2,648,463 A | 8/1953 | Scherer |
| 2,649,619 A | 8/1953 | Killian |
| 2,649,854 A | 8/1953 | Salm |
| 2,690,595 A | 10/1954 | Raiche |
| 2,712,161 A | 7/1955 | Moss |
| 2,856,932 A | 10/1958 | Griffitts |
| 2,912,981 A | 11/1959 | Keough |
| 2,919,697 A | 1/1960 | Kim |
| 3,035,691 A | 5/1962 | Kai et al. |
| 3,044,468 A | 7/1962 | Birtwell |
| 3,053,257 A | 9/1962 | Birtwell |
| 3,076,464 A | 2/1963 | Rosenberg |
| 3,169,527 A | 2/1965 | Sheridan |
| 3,173,566 A | 3/1965 | Talbert |
| 3,211,151 A | 10/1965 | Foderick et al. |
| 3,246,075 A | 4/1966 | Dansard |
| 3,249,285 A | 5/1966 | Franz et al. |
| 3,304,353 A | 2/1967 | Harautuneian |
| 3,344,791 A | 10/1967 | Foderick |
| 3,345,988 A | 10/1967 | Vitello |
| 3,394,704 A | 7/1968 | Dery |
| 3,394,705 A | 7/1968 | Abramson |
| 3,403,682 A | 10/1968 | McDonell |
| 3,409,016 A | 11/1968 | Foley |
| 3,434,869 A | 3/1969 | Davidson |
| 3,463,141 A | 8/1969 | Mozolf |
| 3,478,743 A | 11/1969 | Ericson |
| 3,503,400 A | 3/1970 | Osthagen |
| 3,508,959 A | 4/1970 | Krahnke |
| 3,509,884 A | 5/1970 | Bell |

| | | | |
|---|---|---|---|
| 3,520,305 A | 7/1970 | Davis |
| 3,539,674 A | 11/1970 | Dereniuk et al. |
| 3,544,668 A | 12/1970 | Dereniuk |
| 3,548,805 A | 12/1970 | Datsenko |
| 3,556,294 A | 1/1971 | Walck et al. |
| 3,556,874 A | 1/1971 | McClain |
| 3,566,874 A | 3/1971 | Shepherd et al. |
| 3,593,713 A | 7/1971 | Bogoff et al. |
| 3,598,127 A | 8/1971 | Wepsic |
| 3,606,889 A | 9/1971 | Arblaster |
| 3,642,004 A | 2/1972 | Osthagen et al. |
| 3,646,929 A | 3/1972 | Bonnar |
| 3,648,704 A | 3/1972 | Jackson |
| 3,648,891 A | 3/1972 | Katz et al. |
| 3,651,615 A | 3/1972 | Bohner et al. |
| 3,683,928 A | 8/1972 | Kuntz |
| 3,695,921 A | 10/1972 | Shepherd et al. |
| 3,699,956 A | 10/1972 | Kitrilakis et al. |
| 3,699,964 A | 10/1972 | Ericson |
| 3,708,324 A | 1/1973 | Stebleton |
| 3,726,281 A | 4/1973 | Norton et al. |
| 3,739,783 A | 6/1973 | Broerman |
| 3,761,013 A | 9/1973 | Schuster |
| 3,762,399 A | 10/1973 | Riedell |
| 3,768,102 A | 10/1973 | Kwan-Gett et al. |
| 3,788,324 A | 1/1974 | Lim |
| 3,794,042 A | 2/1974 | De Klotz et al. |
| 3,797,478 A | 3/1974 | Walsh et al. |
| 3,802,987 A | 4/1974 | Noll |
| 3,835,992 A | 9/1974 | Adams, IV |
| 3,838,728 A | 10/1974 | Voegele |
| 3,841,304 A | 10/1974 | Jones |
| 3,854,483 A | 12/1974 | Powers |
| 3,861,395 A | 1/1975 | Taniguchi |
| 3,875,937 A | 4/1975 | Schmitt et al. |
| 3,879,516 A | 4/1975 | Wolvek |
| 3,882,220 A | 5/1975 | Ryder |
| 3,889,685 A | 6/1975 | Miller, Jr. et al. |
| 3,894,540 A | 7/1975 | Bonner, Jr. |
| 3,898,993 A | 8/1975 | Taniguchi |
| 3,924,634 A | 12/1975 | Taylor et al. |
| 3,926,309 A | 12/1975 | Center |
| 3,926,705 A | 12/1975 | Todd |
| 3,930,580 A | 1/1976 | Bazell et al. |
| 3,934,721 A | 1/1976 | Juster et al. |
| 3,962,519 A | 6/1976 | Rusch et al. |
| 3,967,728 A | 7/1976 | Gordon et al. |
| 3,981,299 A | 9/1976 | Murray |
| 3,983,879 A | 10/1976 | Todd |
| 4,026,296 A | 5/1977 | Stoy et al. |
| 4,029,104 A | 6/1977 | Kerber |
| 4,051,849 A | 10/1977 | Poncy et al. |
| 4,055,682 A | 10/1977 | Merrill |
| 4,062,363 A | 12/1977 | Bonner, Jr. |
| 4,069,359 A | 1/1978 | DeMarse et al. |
| 4,091,922 A | 5/1978 | Egler |
| 4,119,094 A | 10/1978 | Micklus et al. |
| 4,120,715 A | 10/1978 | Ockwell et al. |
| 4,133,303 A | 1/1979 | Patel |
| 4,140,127 A | 2/1979 | Cianci et al. |
| 4,149,539 A | 4/1979 | Cianci |
| 4,168,699 A | 9/1979 | Hauser |
| 4,170,996 A * | 10/1979 | Wu ..................... A61M 25/002 604/171 |
| 4,186,745 A | 2/1980 | Lewis et al. |
| 4,187,851 A | 2/1980 | Hauser |
| 4,196,731 A | 4/1980 | Laurin et al. |
| 4,198,983 A | 4/1980 | Becker et al. |
| 4,198,984 A | 4/1980 | Taylor |
| 4,209,010 A | 6/1980 | Ward et al. |
| 4,225,371 A | 9/1980 | Taylor et al. |
| 4,230,115 A | 10/1980 | Walz, Jr. et al. |
| 4,245,639 A | 1/1981 | La Rosa |
| 4,246,909 A | 1/1981 | Wu et al. |
| 4,249,535 A | 2/1981 | Hargest, III |
| 4,252,760 A | 2/1981 | Foster et al. |
| 4,265,848 A | 5/1981 | Rusch |
| 4,266,999 A | 5/1981 | Baier |
| 4,269,310 A | 5/1981 | Uson |

(56) References Cited

U.S. PATENT DOCUMENTS

| | | |
|---|---|---|
| 4,284,459 A | 8/1981 | Patel et al. |
| 4,287,227 A | 9/1981 | Kamada et al. |
| 4,306,557 A | 12/1981 | North |
| 4,311,146 A | 1/1982 | Wonder |
| 4,311,659 A | 1/1982 | Rey et al. |
| 4,318,406 A | 3/1982 | McLeod |
| 4,318,947 A | 3/1982 | Joung |
| 4,341,817 A | 7/1982 | Tozier et al. |
| 4,343,788 A | 8/1982 | Mustacich et al. |
| 4,350,161 A | 9/1982 | Davis, Jr. |
| 4,351,333 A | 9/1982 | Lazarus et al. |
| 4,366,901 A | 1/1983 | Short |
| 4,367,732 A | 1/1983 | Poulsen et al. |
| 4,378,018 A | 3/1983 | Alexander et al. |
| 4,378,796 A | 4/1983 | Milhaud |
| 4,379,506 A | 4/1983 | Davidson |
| 4,381,008 A | 4/1983 | Thomas et al. |
| 4,381,380 A | 4/1983 | LeVeen et al. |
| 4,392,848 A | 7/1983 | Lucas et al. |
| 4,395,806 A | 8/1983 | Wonder et al. |
| 4,411,648 A | 10/1983 | Davis et al. |
| 4,419,097 A | 12/1983 | Rowland |
| 4,428,365 A | 1/1984 | Hakky |
| 4,449,971 A | 5/1984 | Cawood |
| 4,457,299 A | 7/1984 | Cornwell |
| 4,472,226 A | 9/1984 | Redinger et al. |
| 4,475,910 A | 10/1984 | Conway et al. |
| 4,477,325 A | 10/1984 | Osburn |
| 4,479,795 A | 10/1984 | Mustacich et al. |
| 4,486,504 A | 12/1984 | Chung |
| 4,496,354 A | 1/1985 | Steer et al. |
| 4,515,593 A | 5/1985 | Norton |
| 4,517,971 A | 5/1985 | Sorbonne |
| 4,534,768 A | 8/1985 | Osburn et al. |
| 4,539,234 A | 9/1985 | Sakamoto et al. |
| 4,540,409 A | 9/1985 | Nystrom et al. |
| 4,552,269 A | 11/1985 | Chang |
| 4,553,533 A | 11/1985 | Leighton |
| 4,560,382 A | 12/1985 | Sono et al. |
| 4,563,184 A | 1/1986 | Korol |
| 4,568,340 A | 2/1986 | Giacalone |
| 4,571,239 A | 2/1986 | Heyman |
| 4,571,240 A | 2/1986 | Samson et al. |
| 4,571,241 A | 2/1986 | Christopher |
| 4,576,599 A | 3/1986 | Lipner |
| 4,581,026 A | 4/1986 | Schneider |
| 4,581,028 A | 4/1986 | Fox, Jr. et al. |
| 4,582,762 A | 4/1986 | Onohara et al. |
| 4,585,666 A | 4/1986 | Lambert |
| 4,586,974 A | 5/1986 | Nystrom et al. |
| 4,589,874 A | 5/1986 | Riedel et al. |
| 4,592,920 A | 6/1986 | Murtfeldt |
| 4,597,765 A | 7/1986 | Klatt |
| 4,597,931 A | 7/1986 | Watanabe et al. |
| 4,601,713 A | 7/1986 | Fuqua |
| 4,603,152 A | 7/1986 | Laurin et al. |
| 4,607,746 A | 8/1986 | Stinnette |
| 4,610,670 A | 9/1986 | Spencer |
| 4,612,337 A | 9/1986 | Fox, Jr. et al. |
| 4,613,324 A | 9/1986 | Ghajar |
| 4,615,692 A | 10/1986 | Giacalone et al. |
| 4,615,697 A | 10/1986 | Robinson |
| 4,619,642 A | 10/1986 | Spencer |
| 4,622,033 A | 11/1986 | Taniguchi |
| 4,623,329 A | 11/1986 | Drobish et al. |
| 4,626,250 A | 12/1986 | Schneider |
| 4,627,844 A | 12/1986 | Schmitt |
| 4,634,433 A | 1/1987 | Osborne |
| 4,637,907 A | 1/1987 | Hegel et al. |
| 4,638,790 A | 1/1987 | Conway et al. |
| 4,639,246 A | 1/1987 | Dudley |
| 4,640,688 A | 2/1987 | Hauser |
| 4,652,259 A | 3/1987 | O'Neil |
| 4,664,657 A | 5/1987 | Williamitis et al. |
| 4,673,401 A | 6/1987 | Jensen et al. |
| 4,677,143 A | 6/1987 | Laurin et al. |
| 4,681,572 A | 7/1987 | Tokarz et al. |
| 4,685,913 A | 8/1987 | Austin |
| 4,686,124 A | 8/1987 | Onohara et al. |
| 4,687,470 A | 8/1987 | Okada |
| 4,692,152 A | 9/1987 | Emde |
| 4,692,154 A | 9/1987 | Singery et al. |
| 4,696,672 A | 9/1987 | Mochizuki et al. |
| 4,699,616 A | 10/1987 | Nowak et al. |
| 4,704,102 A | 11/1987 | Guthery |
| 4,710,169 A | 12/1987 | Christopher |
| 4,710,181 A | 12/1987 | Fuqua |
| 4,723,946 A | 2/1988 | Kay |
| 4,731,064 A | 3/1988 | Heyden |
| 4,737,219 A | 4/1988 | Taller et al. |
| 4,738,667 A | 4/1988 | Galloway |
| 4,739,768 A | 4/1988 | Engelson |
| 4,747,845 A | 5/1988 | Korol |
| 4,754,877 A | 7/1988 | Johansson et al. |
| 4,759,753 A | 7/1988 | Schneider et al. |
| 4,762,128 A | 8/1988 | Rosenbluth |
| 4,769,013 A | 9/1988 | Lorenz et al. |
| 4,769,099 A | 9/1988 | Therriault et al. |
| 4,772,473 A | 9/1988 | Patel et al. |
| 4,773,901 A | 9/1988 | Norton |
| 4,775,371 A | 10/1988 | Mueller, Jr. |
| 4,784,651 A | 11/1988 | Hickey et al. |
| 4,790,834 A | 12/1988 | Austin |
| 4,790,835 S | 12/1988 | Elias |
| D299,865 S | 2/1989 | Kamstrup-Larsen et al. |
| 4,810,247 A | 3/1989 | Glassman |
| 4,811,847 A | 3/1989 | Reif et al. |
| 4,813,935 A | 3/1989 | Haber et al. |
| 4,820,270 A | 4/1989 | Hardcastle et al. |
| 4,820,289 A | 4/1989 | Coury et al. |
| 4,820,291 A | 4/1989 | Terauchi et al. |
| 4,820,292 A | 4/1989 | Korol et al. |
| 4,834,721 A | 5/1989 | Onohara et al. |
| 4,838,876 A | 6/1989 | Wong et al. |
| 4,846,784 A | 7/1989 | Haber |
| 4,846,909 A | 7/1989 | Klug et al. |
| 4,850,969 A | 7/1989 | Jackson |
| 4,861,337 A | 8/1989 | George |
| 4,863,424 A | 9/1989 | Blake, III et al. |
| 4,863,444 A | 9/1989 | Blomer |
| 4,863,449 A | 9/1989 | Therriault et al. |
| 4,867,748 A | 9/1989 | Samuelsen |
| 4,874,373 A | 10/1989 | Luther et al. |
| 4,876,109 A | 10/1989 | Mayer et al. |
| 4,885,049 A | 12/1989 | Johannesson |
| 4,886,508 A | 12/1989 | Washington |
| 4,888,005 A | 12/1989 | Dingeman et al. |
| 4,893,623 A | 1/1990 | Rosenbluth |
| 4,894,059 A | 1/1990 | Larsen et al. |
| 4,902,503 A | 2/1990 | Umemura et al. |
| 4,904,260 A | 2/1990 | Ray et al. |
| 4,917,113 A | 4/1990 | Conway et al. |
| 4,917,686 A | 4/1990 | Bayston et al. |
| RE33,206 E | 5/1990 | Conway et al. |
| 4,923,450 A | 5/1990 | Maeda et al. |
| 4,925,668 A | 5/1990 | Khan et al. |
| 4,930,522 A | 6/1990 | Busnel et al. |
| 4,931,056 A | 6/1990 | Ghajar et al. |
| 4,932,938 A | 6/1990 | Goldberg et al. |
| 4,932,948 A | 6/1990 | Kernes et al. |
| 4,934,999 A | 6/1990 | Bader |
| 4,935,260 A | 6/1990 | Shlenker |
| 4,950,256 A | 8/1990 | Luther et al. |
| 4,957,487 A | 9/1990 | Gerow |
| 4,963,137 A | 10/1990 | Heyden |
| 4,968,294 A | 11/1990 | Salama |
| 4,968,507 A | 11/1990 | Zentner et al. |
| 4,976,703 A | 12/1990 | Franetzki et al. |
| 4,981,471 A | 1/1991 | Quinn et al. |
| 4,994,047 A | 2/1991 | Walker et al. |
| 4,997,426 A | 3/1991 | Dingeman et al. |
| 5,001,009 A | 3/1991 | Whitbourne |
| 5,004,454 A | 4/1991 | Beyar et al. |
| 5,007,897 A | 4/1991 | Kalb et al. |

(56)　　　　　　References Cited

U.S. PATENT DOCUMENTS

| | | | |
|---|---|---|---|
| 5,013,306 A | 5/1991 | Solomon et al. | |
| 5,013,717 A | 5/1991 | Solomon et al. | |
| 5,019,096 A | 5/1991 | Fox, Jr. et al. | |
| 5,019,378 A | 5/1991 | Allen | |
| 5,019,601 A | 5/1991 | Allen | |
| 5,045,078 A | 9/1991 | Asta | |
| 5,059,190 A | 10/1991 | Novak | |
| 5,062,716 A | 11/1991 | Conrad et al. | |
| 5,071,406 A | 12/1991 | Jang | |
| 5,077,352 A | 12/1991 | Elton | |
| 5,078,707 A | 1/1992 | Peter Klug | |
| 5,082,006 A | 1/1992 | Jonasson | |
| 5,084,037 A | 1/1992 | Barnett | |
| 5,087,252 A | 2/1992 | Denard | |
| 5,088,980 A | 2/1992 | Leighton | |
| 5,089,205 A | 2/1992 | Huang et al. | |
| 5,090,424 A | 2/1992 | Simon et al. | |
| 5,098,379 A | 3/1992 | Conway et al. | |
| 5,100,396 A | 3/1992 | Zamierowski | |
| 5,102,401 A | 4/1992 | Lambert et al. | |
| 5,102,405 A | 4/1992 | Conway et al. | |
| 5,109,378 A | 4/1992 | Proctor et al. | |
| 5,109,601 A | 5/1992 | McBride | |
| 5,112,306 A | 5/1992 | Burton et al. | |
| 5,114,398 A | 5/1992 | Trick et al. | |
| 5,118,007 A | 6/1992 | Lewis et al. | |
| 5,128,088 A | 7/1992 | Shimomura et al. | |
| 5,131,906 A | 7/1992 | Chen | |
| 5,137,671 A | 8/1992 | Conway et al. | |
| 5,140,999 A | 8/1992 | Ardito | |
| 5,147,341 A | 9/1992 | Starke et al. | |
| 5,165,952 A | 11/1992 | Solomon et al. | |
| 5,174,290 A | 12/1992 | Fiddian-Green | |
| 5,176,666 A | 1/1993 | Conway et al. | |
| 5,179,174 A | 1/1993 | Elton | |
| 5,180,591 A | 1/1993 | Magruder et al. | |
| 5,186,172 A | 2/1993 | Fiddian-Green | |
| 5,188,596 A | 2/1993 | Condon et al. | |
| 5,197,957 A | 3/1993 | Wendler | |
| 5,201,724 A | 4/1993 | Hukins et al. | |
| 5,209,726 A | 5/1993 | Goosen | |
| 5,209,728 A | 5/1993 | Kraus et al. | |
| 5,211,640 A | 5/1993 | Wendler | |
| 5,224,953 A | 7/1993 | Morgentaler | |
| 5,226,530 A | 7/1993 | Golden | |
| 5,234,411 A | 8/1993 | Vaillancourt et al. | |
| 5,236,422 A | 8/1993 | Eplett, Jr. | |
| 5,242,391 A | 9/1993 | Place et al. | |
| 5,242,398 A | 9/1993 | Knoll et al. | |
| 5,242,428 A | 9/1993 | Palestrant | |
| 5,261,896 A | 11/1993 | Conway et al. | |
| 5,263,947 A | 11/1993 | Kay | |
| 5,269,755 A | 12/1993 | Bodicky | |
| 5,269,770 A | 12/1993 | Conway et al. | |
| 5,270,358 A | 12/1993 | Asmus | |
| 5,282,795 A | 2/1994 | Finney | |
| 5,290,306 A | 3/1994 | Trotta et al. | |
| 5,306,226 A | 4/1994 | Salama | |
| 5,334,175 A | 8/1994 | Conway et al. | |
| 5,336,211 A | 8/1994 | Metz | |
| 5,346,483 A | 9/1994 | Thaxton, Sr. | |
| 5,348,536 A | 9/1994 | Young et al. | |
| 5,352,182 A | 10/1994 | Kalb et al. | |
| 5,354,132 A | 10/1994 | Young et al. | |
| 5,360,402 A | 11/1994 | Conway et al. | |
| 5,360,414 A | 11/1994 | Yarger | |
| 5,366,449 A | 11/1994 | Gilberg | |
| 5,368,575 A | 11/1994 | Chang | |
| 5,370,899 A | 12/1994 | Conway et al. | |
| 5,376,085 A | 12/1994 | Conway et al. | |
| 5,380,312 A | 1/1995 | Goulter | |
| 5,395,333 A | 3/1995 | Brill | |
| 5,409,014 A | 4/1995 | Napoli et al. | |
| 5,409,495 A | 4/1995 | Osborn | |
| 5,415,165 A | 5/1995 | Fiddian-Green | |
| 5,415,635 A | 5/1995 | Bagaoisan et al. | |
| 5,417,226 A | 5/1995 | Juma | |
| 5,417,666 A | 5/1995 | Coulter | |
| 5,423,784 A | 6/1995 | Metz | |
| 5,433,705 A | 7/1995 | Giebel et al. | |
| 5,433,713 A | 7/1995 | Trotta | |
| 5,445,626 A | 8/1995 | Gigante et al. | |
| 5,447,231 A | 9/1995 | Kastenhofer | |
| 5,451,424 A | 9/1995 | Solomon et al. | |
| 5,454,798 A | 10/1995 | Kubalak et al. | |
| 5,456,251 A | 10/1995 | Fiddian-Green | |
| 5,464,650 A | 11/1995 | Berg et al. | |
| 5,466,229 A | 11/1995 | Elson et al. | |
| 5,476,434 A | 12/1995 | Kalb et al. | |
| 5,479,945 A | 1/1996 | Simon | |
| 5,482,740 A | 1/1996 | Conway et al. | |
| 5,483,976 A | 1/1996 | McLaughlin et al. | |
| 5,497,601 A | 3/1996 | Gonzalez | |
| 5,501,669 A | 3/1996 | Conway et al. | |
| 5,509,427 A | 4/1996 | Simon et al. | |
| 5,509,889 A | 4/1996 | Kalb et al. | |
| 5,509,899 A | 4/1996 | Fan et al. | |
| 5,513,659 A | 5/1996 | Buuck et al. | |
| 5,513,660 A | 5/1996 | Simon et al. | |
| 5,514,112 A | 5/1996 | Chu et al. | |
| 5,520,636 A | 5/1996 | Korth et al. | |
| 5,531,715 A | 7/1996 | Engelson et al. | |
| 5,531,717 A | 7/1996 | Roberto et al. | |
| 5,536,258 A | 7/1996 | Folden | |
| 5,538,584 A | 7/1996 | Metz | |
| 5,554,140 A | 9/1996 | Michels et al. | |
| 5,554,141 A | 9/1996 | Wendler | |
| 5,558,900 A | 9/1996 | Fan et al. | |
| 5,562,599 A | 10/1996 | Beyschlag | |
| 5,567,495 A | 10/1996 | Modak et al. | |
| 5,569,219 A | 10/1996 | Hakki et al. | |
| 5,582,599 A | 12/1996 | Daneshvar | |
| 5,591,292 A | 1/1997 | Blomqvist | |
| 5,593,718 A | 1/1997 | Conway et al. | |
| 5,599,321 A | 2/1997 | Conway et al. | |
| 5,601,537 A | 2/1997 | Frassica | |
| 5,607,417 A | 3/1997 | Batich et al. | |
| 5,614,143 A | 3/1997 | Hager | |
| 5,616,126 A | 4/1997 | Malekmehr et al. | |
| 5,620,109 A | 4/1997 | Madden | |
| 5,624,395 A | 4/1997 | Mikhail et al. | |
| 5,630,429 A | 5/1997 | Dann | |
| 5,643,235 A | 7/1997 | Figuerido | |
| 5,645,048 A * | 7/1997 | Brodsky ........... | A61M 16/0841 |
| | | | 128/207.14 |
| 5,653,700 A | 8/1997 | Byrne et al. | |
| 5,670,111 A | 9/1997 | Conway et al. | |
| 5,671,755 A | 9/1997 | Simon et al. | |
| 5,688,516 A | 11/1997 | Raad et al. | |
| 5,695,456 A | 12/1997 | Cartmell et al. | |
| 5,695,485 A | 12/1997 | Duperret et al. | |
| 5,702,381 A | 12/1997 | Cottenden | |
| 5,704,353 A | 1/1998 | Kalb et al. | |
| 5,707,357 A | 1/1998 | Mikhail et al. | |
| 5,709,672 A | 1/1998 | Ilner | |
| 5,711,841 A | 1/1998 | Jaker | |
| 5,724,994 A | 3/1998 | Simon et al. | |
| 5,730,733 A | 3/1998 | Mortier et al. | |
| 5,736,152 A | 4/1998 | Dunn | |
| 5,749,826 A | 5/1998 | Faulkner | |
| 5,752,525 A | 5/1998 | Simon et al. | |
| 5,756,144 A | 5/1998 | Wolff et al. | |
| 5,762,996 A | 6/1998 | Lucas et al. | |
| 5,779,670 A | 7/1998 | Bidwell et al. | |
| 5,782,808 A | 7/1998 | Folden | |
| 5,785,694 A | 7/1998 | Cohen et al. | |
| 5,788,687 A | 8/1998 | Batich et al. | |
| 5,789,018 A | 8/1998 | Engelson et al. | |
| 5,795,332 A | 8/1998 | Lucas et al. | |
| 5,795,334 A | 8/1998 | Cochrane, III | |
| 5,795,524 A | 8/1998 | Basso, Jr. et al. | |
| 5,800,339 A | 9/1998 | Salama | |
| 5,806,527 A | 9/1998 | Borodulin et al. | |
| 5,810,789 A | 9/1998 | Powers et al. | |

(56) References Cited

U.S. PATENT DOCUMENTS

| | | | |
|---|---|---|---|
| 5,817,067 A | 10/1998 | Tsukada et al. |
| 5,820,583 A | 10/1998 | Demopulos et al. |
| 5,820,607 A | 10/1998 | Tcholakian et al. |
| 5,827,247 A | 10/1998 | Kay |
| 5,827,249 A | 10/1998 | Jensen |
| 5,830,932 A | 11/1998 | Kay |
| 5,840,151 A | 11/1998 | Munsch |
| 5,848,691 A | 12/1998 | Morris et al. |
| 5,853,518 A | 12/1998 | Utas |
| 5,871,475 A | 2/1999 | Frassica |
| 5,877,243 A | 3/1999 | Sarangapani |
| 5,895,374 A | 4/1999 | Rodsten |
| 5,897,535 A | 4/1999 | Feliziani et al. |
| 5,902,631 A | 5/1999 | Wang et al. |
| 5,906,575 A | 5/1999 | Conway et al. |
| 5,919,170 A | 7/1999 | Woessner |
| 5,941,856 A | 8/1999 | Kovacs et al. |
| 5,958,167 A | 9/1999 | Van Driel et al. |
| 5,971,954 A | 10/1999 | Conway et al. |
| 5,980,483 A | 11/1999 | Dimitri |
| 5,980,507 A | 11/1999 | Fassuliotis et al. |
| 5,989,230 A | 11/1999 | Frassica |
| 5,997,517 A | 12/1999 | Whitbourne |
| 6,004,305 A | 12/1999 | Hursman et al. |
| 6,007,521 A | 12/1999 | Bidwell et al. |
| 6,007,524 A | 12/1999 | Schneider |
| 6,007,526 A | 12/1999 | Passalaqua et al. |
| 6,024,751 A | 2/2000 | Lovato et al. |
| 6,050,934 A | 4/2000 | Mikhail et al. |
| 6,053,905 A | 4/2000 | Daignault, Jr. et al. |
| 6,056,715 A | 5/2000 | Demopulos et al. |
| 6,059,107 A | 5/2000 | Nosted et al. |
| 6,063,063 A | 5/2000 | Harboe et al. |
| 6,065,597 A | 5/2000 | Pettersson et al. |
| 6,070,275 A | 6/2000 | Garlock |
| 6,090,075 A | 7/2000 | House |
| 6,097,976 A | 8/2000 | Yang et al. |
| 6,102,929 A | 8/2000 | Conway et al. |
| 6,113,582 A | 9/2000 | Dwork |
| 6,119,697 A | 9/2000 | Engel et al. |
| 6,131,575 A | 10/2000 | Lenker et al. |
| 6,132,399 A | 10/2000 | Shultz |
| 6,156,049 A | 12/2000 | Lovato et al. |
| 6,162,201 A | 12/2000 | Cohen et al. |
| 6,183,461 B1 | 2/2001 | Matsuura et al. |
| 6,186,990 B1 | 2/2001 | Chen et al. |
| 6,190,353 B1 | 2/2001 | Makower et al. |
| 6,206,885 B1 | 3/2001 | Ghahremani et al. |
| 6,210,394 B1 | 4/2001 | Demopulos et al. |
| 6,217,569 B1 | 4/2001 | Fiore |
| 6,221,056 B1 | 4/2001 | Silverman |
| 6,231,501 B1 | 5/2001 | Ditter |
| 6,238,383 B1 | 5/2001 | Karram et al. |
| 6,254,570 B1 | 7/2001 | Rutner et al. |
| 6,254,582 B1 | 7/2001 | O'Donnell et al. |
| 6,254,585 B1 | 7/2001 | Demopulos et al. |
| 6,256,525 B1 | 7/2001 | Yang et al. |
| 6,261,255 B1 | 7/2001 | Mullis et al. |
| 6,261,271 B1 | 7/2001 | Solomon et al. |
| 6,261,279 B1 | 7/2001 | Demopulos et al. |
| 6,270,902 B1 | 8/2001 | Tedeschi et al. |
| 6,280,425 B1 | 8/2001 | Del Guercio |
| 6,287,285 B1 | 9/2001 | Michal et al. |
| 6,293,923 B1 | 9/2001 | Yachia et al. |
| 6,296,627 B1 | 10/2001 | Edwards |
| 6,299,598 B1 | 10/2001 | Bander |
| 6,306,176 B1 | 10/2001 | Whitbourne |
| 6,306,422 B1 | 10/2001 | Batich et al. |
| 6,309,104 B1 | 10/2001 | Koch et al. |
| 6,315,711 B1 | 11/2001 | Conway et al. |
| 6,329,488 B1 | 12/2001 | Terry et al. |
| 6,340,359 B1 | 1/2002 | Silverman |
| 6,340,465 B1 | 1/2002 | Hsu et al. |
| 6,355,004 B1 | 3/2002 | Pedersen et al. |
| 6,358,229 B1 | 3/2002 | Tihon |
| 6,368,315 B1 | 4/2002 | Gillis et al. |
| 6,368,317 B2 | 4/2002 | Chang |
| 6,379,334 B1 | 4/2002 | Frassica |
| 6,383,434 B2 | 5/2002 | Conway et al. |
| 6,387,080 B1 | 5/2002 | Rodsten |
| 6,391,010 B1 | 5/2002 | Wilcox |
| 6,391,014 B1 | 5/2002 | Silverman |
| 6,398,718 B1 | 6/2002 | Yachia et al. |
| 6,402,726 B1 | 6/2002 | Genese |
| 6,409,717 B1 | 6/2002 | Sraelsson et al. |
| 6,423,041 B1 | 7/2002 | Grant |
| 6,437,038 B1 | 8/2002 | Chen |
| 6,440,060 B1 | 8/2002 | Latour, Jr. |
| 6,458,867 B1 | 10/2002 | Wang et al. |
| 6,468,245 B2 | 10/2002 | Alexandersen |
| 6,479,000 B2 | 11/2002 | Conway et al. |
| 6,479,726 B1 | 11/2002 | Cole |
| 6,485,476 B1 | 11/2002 | von Dyck et al. |
| 6,509,319 B1 | 1/2003 | Raad et al. |
| 6,544,240 B1 | 4/2003 | Borodulin et al. |
| 6,551,293 B1 | 4/2003 | Mitchell |
| 6,558,369 B2 | 5/2003 | Rosenblum |
| 6,558,792 B1 | 5/2003 | Vaabengaard et al. |
| 6,558,798 B2 | 5/2003 | Zhong et al. |
| 6,578,709 B1 | 6/2003 | Kavanagh et al. |
| 6,579,539 B2 | 6/2003 | Lawson et al. |
| 6,582,401 B1 | 6/2003 | Windheuser et al. |
| 6,596,401 B1 | 7/2003 | Terry et al. |
| 6,602,244 B2 | 8/2003 | Kavanagh et al. |
| 6,613,014 B1 | 9/2003 | Chi |
| 6,613,342 B2 | 9/2003 | Aoki |
| 6,626,888 B1 | 9/2003 | Conway et al. |
| 6,629,969 B2 | 10/2003 | Chan et al. |
| 6,632,204 B2 | 10/2003 | Guldfeldt et al. |
| 6,634,498 B2 | 10/2003 | Kayerod et al. |
| 6,638,269 B2 | 10/2003 | Wilcox |
| 6,648,906 B2 | 11/2003 | Lasheras et al. |
| 6,659,937 B2 | 12/2003 | Polsky et al. |
| 6,682,555 B2 | 1/2004 | Cioanta et al. |
| 6,693,189 B2 | 2/2004 | Holt et al. |
| 6,695,831 B1 | 2/2004 | Tsukada et al. |
| 6,706,025 B2 | 3/2004 | Engelson et al. |
| 6,711,436 B1 | 3/2004 | Duhaylongsod |
| 6,716,895 B1 | 4/2004 | Terry |
| 6,719,709 B2 | 4/2004 | Whalen et al. |
| 6,723,350 B2 | 4/2004 | Burrell et al. |
| 6,730,113 B2 | 5/2004 | Eckhardt et al. |
| 6,733,474 B2 | 5/2004 | Kusleika |
| 6,736,805 B2 | 5/2004 | Israelsson et al. |
| 6,740,273 B2 | 5/2004 | Lee |
| 6,746,421 B2 | 6/2004 | Yachia et al. |
| 6,767,551 B2 | 7/2004 | McGhee et al. |
| 6,780,504 B2 | 8/2004 | Rupprecht et al. |
| 6,783,520 B1 | 8/2004 | Candray et al. |
| D496,266 S | 9/2004 | Nestenborg |
| 6,787,156 B1 | 9/2004 | Bar-Shalom |
| 6,797,743 B2 | 9/2004 | McDonald et al. |
| 6,824,532 B2 | 11/2004 | Gillis et al. |
| 6,835,183 B2 | 12/2004 | Lennox et al. |
| 6,835,410 B2 | 12/2004 | Chabrecek et al. |
| 6,840,379 B2 | 1/2005 | Franks-Farah et al. |
| 6,848,574 B1 | 2/2005 | Israelsson et al. |
| 6,849,070 B1 | 2/2005 | Hansen et al. |
| 6,852,098 B2 | 2/2005 | Byrne |
| 6,852,105 B2 | 2/2005 | Bolmsjo et al. |
| D503,335 S | 3/2005 | Risberg et al. |
| 6,869,416 B2 | 3/2005 | Windheuser et al. |
| 6,872,195 B2 | 3/2005 | Modak et al. |
| 6,887,223 B2 | 5/2005 | Bisbee |
| 6,887,230 B2 | 5/2005 | Kubalak et al. |
| 6,889,740 B1 | 5/2005 | Globensky et al. |
| 6,918,924 B2 | 7/2005 | Lasheras et al. |
| 6,926,708 B1 | 8/2005 | Franks-Farah et al. |
| 6,939,339 B1 | 9/2005 | Axexandersen et al. |
| 6,939,554 B2 | 9/2005 | McDonald et al. |
| 6,941,171 B2 | 9/2005 | Mann et al. |
| 6,942,634 B2 | 9/2005 | Odland |
| 6,945,957 B2 | 9/2005 | Freyman |
| 6,949,598 B2 | 9/2005 | Terry |

(56) References Cited

U.S. PATENT DOCUMENTS

| | | |
|---|---|---|
| 6,951,902 B2 | 10/2005 | McDonald et al. |
| 6,972,040 B2 | 12/2005 | Rioux et al. |
| 7,001,370 B2 | 2/2006 | Kubalak et al. |
| 7,033,367 B2 | 4/2006 | Ghahremani et al. |
| 7,048,717 B1 | 5/2006 | Frassica |
| 7,059,330 B1 | 6/2006 | Makower et al. |
| 7,066,912 B2 | 6/2006 | Nestenborg et al. |
| 7,087,041 B2 | 8/2006 | von Dyck et al. |
| 7,087,048 B2 | 8/2006 | Israelsson et al. |
| 7,094,220 B2 | 8/2006 | Tanghoj et al. |
| 7,112,298 B2 | 9/2006 | Kampa et al. |
| 7,160,277 B2 | 1/2007 | Elson et al. |
| 7,166,092 B2 | 1/2007 | Elson et al. |
| 7,195,608 B2 | 3/2007 | Burnett |
| 7,204,940 B2 | 4/2007 | McDonald et al. |
| 7,211,275 B2 | 5/2007 | Mng et al. |
| 7,244,242 B2 | 7/2007 | Freyman |
| 7,250,043 B2 | 7/2007 | Chan et al. |
| 7,255,687 B2 | 8/2007 | Huang et al. |
| 7,270,647 B2 | 9/2007 | Karpowicz et al. |
| 7,294,117 B2 | 11/2007 | Provost-tine et al. |
| 7,311,690 B2 | 12/2007 | Burnett |
| 7,311,698 B2 | 12/2007 | Tanghoj et al. |
| 7,329,412 B2 | 2/2008 | Modak et al. |
| 7,331,948 B2 | 2/2008 | Skarda |
| 7,334,679 B2 | 2/2008 | Givens, Jr. |
| 7,374,040 B2 | 5/2008 | Lee et al. |
| 7,380,658 B2 | 6/2008 | Murray et al. |
| 7,402,559 B2 | 7/2008 | Catania et al. |
| 7,445,812 B2 | 11/2008 | Schmidt et al. |
| 7,458,964 B2 | 12/2008 | Mosler et al. |
| 7,476,223 B2 | 1/2009 | McBride |
| 7,507,229 B2 | 3/2009 | Hewitt et al. |
| 7,517,343 B2 | 4/2009 | Tanghoj et al. |
| 7,537,589 B2 | 5/2009 | Tsukada et al. |
| 7,571,804 B2 | 8/2009 | Kjellmann Bruun et al. |
| 7,601,158 B2 | 10/2009 | House |
| 7,615,045 B2 | 11/2009 | Israelsson et al. |
| 7,628,784 B2 | 12/2009 | Diaz et al. |
| 7,632,256 B2 | 12/2009 | Mosler et al. |
| D609,819 S | 2/2010 | Tomes et al. |
| 7,662,146 B2 | 2/2010 | House |
| 7,670,331 B2 | 3/2010 | Tanghoej |
| 7,682,353 B2 | 3/2010 | Tanghoj et al. |
| 7,682,669 B1 | 3/2010 | Michal et al. |
| 7,691,091 B1 | 4/2010 | Baggett |
| 7,691,476 B2 | 4/2010 | Finley |
| 7,717,902 B2 | 5/2010 | Sauer |
| 7,749,529 B2 | 7/2010 | Ash et al. |
| 7,770,726 B2 | 8/2010 | Murray et al. |
| 7,770,728 B2 | 8/2010 | Kaem |
| 7,780,640 B1 | 8/2010 | Amador |
| 7,780,642 B2 | 8/2010 | Rasmussen et al. |
| 7,789,873 B2 | 9/2010 | Kubalak et al. |
| 7,820,734 B2 | 10/2010 | McGhee |
| 7,823,722 B2 | 11/2010 | Bezou et al. |
| 7,846,133 B2 | 12/2010 | Windheuser et al. |
| 7,867,220 B2 | 1/2011 | Tanghoj |
| 7,886,907 B2 | 2/2011 | Murray et al. |
| 7,896,857 B2 | 3/2011 | Kay et al. |
| 7,918,831 B2 | 4/2011 | House |
| 7,938,838 B2 | 5/2011 | House |
| 7,947,021 B2 | 5/2011 | Bourne et al. |
| 7,985,217 B2 | 7/2011 | Mosler et al. |
| 8,007,464 B2 | 8/2011 | Gellman |
| 8,011,505 B2 | 9/2011 | Murray et al. |
| 8,051,981 B2 | 11/2011 | Murray et al. |
| 8,052,673 B2 | 11/2011 | Nestenborg |
| 8,053,030 B2 | 11/2011 | Gilman |
| 8,066,693 B2 | 11/2011 | Tanghoj et al. |
| 8,127,922 B2 | 3/2012 | Nordholm et al. |
| 8,133,580 B2 | 3/2012 | Dias et al. |
| 8,163,327 B2 | 4/2012 | Finley |
| 8,177,774 B2 | 5/2012 | House |
| 8,181,778 B1 | 5/2012 | van Groningen et al. |
| 8,192,413 B2 | 6/2012 | Bjerregaard |
| 8,201,689 B2 | 6/2012 | Kaern |
| 8,205,745 B2 | 6/2012 | Murray et al. |
| 8,207,393 B2 | 6/2012 | Bach |
| 8,230,993 B2 | 7/2012 | Tanghoej |
| 8,267,919 B2 | 9/2012 | Utas et al. |
| 8,282,624 B2 | 10/2012 | Tanghoej et al. |
| 8,287,519 B2 | 10/2012 | Smith |
| 8,287,890 B2 | 10/2012 | Elton |
| 8,298,202 B2 | 10/2012 | McCray |
| 8,303,556 B2 | 11/2012 | White |
| 8,317,775 B2 | 11/2012 | House |
| 8,328,792 B2 | 12/2012 | Nishtala et al. |
| 8,356,457 B2 | 1/2013 | Murray et al. |
| 8,377,498 B2 | 2/2013 | Rindlav-Westling et al. |
| 8,377,559 B2 | 2/2013 | Gilman |
| 8,382,708 B2 | 2/2013 | Mayback et al. |
| 8,398,615 B2 | 3/2013 | Torstensen et al. |
| 8,409,171 B2 | 4/2013 | Hannon et al. |
| 8,454,569 B2 | 6/2013 | Kull-Osterlin et al. |
| 8,459,455 B2 | 6/2013 | Frojd |
| 8,475,434 B2 | 7/2013 | Frojd |
| 8,523,843 B2 | 9/2013 | Kavanagh et al. |
| 8,556,884 B2 | 10/2013 | Hong et al. |
| 8,608,718 B1 | 12/2013 | Patterson-Young |
| 8,668,683 B2 | 3/2014 | Golden |
| 8,720,685 B2 | 5/2014 | Murray et al. |
| 8,805,533 B2 | 8/2014 | Boggs, II et al. |
| 8,871,869 B2 | 10/2014 | Dias et al. |
| 8,888,747 B2 | 11/2014 | House |
| 8,919,553 B2 | 12/2014 | Murray et al. |
| 8,974,438 B2 | 3/2015 | Hong et al. |
| 8,998,882 B2 | 4/2015 | Knapp et al. |
| 9,033,149 B2 | 5/2015 | Terry |
| 9,072,862 B2 | 7/2015 | Murray et al. |
| 9,078,760 B2 | 7/2015 | Marshall |
| 9,108,020 B1 | 8/2015 | Feloney |
| 9,114,227 B2 | 8/2015 | Blanchard |
| 9,138,510 B2 | 9/2015 | Madsen |
| 9,144,659 B2 | 9/2015 | Tanghoj |
| 9,168,354 B2 | 10/2015 | Hannon et al. |
| 9,186,438 B2 | 11/2015 | Gravesen et al. |
| 9,192,506 B2 | 11/2015 | Tanghoej et al. |
| 9,192,740 B2 | 11/2015 | Frojd |
| 9,199,057 B2 | 12/2015 | Nielsen |
| 9,205,222 B2 | 12/2015 | Tanghoj |
| 9,220,866 B2 | 12/2015 | Van Groningen et al. |
| 9,289,575 B2 | 3/2016 | Dye |
| 9,314,585 B2 | 4/2016 | Nestenborg et al. |
| 9,345,855 B2 | 5/2016 | Young |
| 9,511,204 B2 | 12/2016 | Tanghøj |
| 9,561,889 B2 | 2/2017 | Dayrit et al. |
| 9,649,472 B2 | 5/2017 | Kearns et al. |
| 9,669,187 B2 | 6/2017 | Tjassens et al. |
| 9,687,628 B2 | 6/2017 | Paz |
| 9,694,113 B2 | 7/2017 | Knapp et al. |
| 9,694,157 B2 | 7/2017 | Palmer |
| 9,707,375 B2 | 7/2017 | Conway et al. |
| 9,731,093 B2 | 8/2017 | Terry |
| 9,775,965 B2 | 10/2017 | Tanghoej et al. |
| 9,801,979 B2 | 10/2017 | Utas et al. |
| 9,821,139 B2 | 11/2017 | Carleo |
| 9,872,969 B2 | 1/2018 | Conway et al. |
| 9,884,167 B2 | 2/2018 | Gustavsson |
| 9,918,869 B2 | 3/2018 | Henry et al. |
| 9,937,334 B2 | 4/2018 | Fröjd et al. |
| 10,112,031 B2 | 10/2018 | Matthiassen |
| 10,118,019 B2 | 11/2018 | Murray et al. |
| 10,149,961 B2 | 12/2018 | Carleo |
| 10,166,366 B2 | 1/2019 | Murray et al. |
| 10,179,676 B1 | 1/2019 | Taylor |
| 10,207,076 B2 | 2/2019 | Foley et al. |
| 10,265,499 B2 | 4/2019 | Hong et al. |
| 10,328,237 B2 | 6/2019 | Kelly et al. |
| 10,406,322 B2 | 9/2019 | O'Flynn et al. |
| 10,441,454 B2 | 10/2019 | Tanghoej et al. |
| 10,449,328 B2 | 10/2019 | Tanghoej et al. |
| 10,449,329 B2 | 10/2019 | Foley et al. |
| 10,518,000 B2 | 12/2019 | Knapp et al. |

(56)                References Cited

U.S. PATENT DOCUMENTS

| | | |
|---|---|---|
| 10,561,817 B2 | 2/2020 | Hannon et al. |
| 10,569,046 B2 | 2/2020 | Steindahl et al. |
| 10,569,051 B2 | 2/2020 | Conway et al. |
| 10,639,451 B2 | 5/2020 | Keams et al. |
| 10,646,688 B2 | 5/2020 | Hannon et al. |
| 10,702,671 B2 | 7/2020 | Terry |
| 10,758,704 B2 | 9/2020 | Hickmott et al. |
| 10,765,833 B2 | 9/2020 | Keams |
| 10,857,324 B2 | 12/2020 | Yin et al. |
| 10,874,825 B2 | 12/2020 | Yin et al. |
| RE48,426 E | 2/2021 | Murray et al. |
| 10,912,917 B2 | 2/2021 | Terry |
| 11,020,561 B2 | 6/2021 | O'Brien et al. |
| 11,103,676 B2 | 8/2021 | McMenamin et al. |
| 11,129,961 B2 | 9/2021 | O'Flynn |
| 11,141,562 B2 | 10/2021 | McMenamin et al. |
| 11,154,688 B2 | 10/2021 | Schertiger |
| 11,167,107 B2 | 11/2021 | Schertiger et al. |
| 11,235,130 B2 | 2/2022 | Murray et al. |
| 11,241,566 B1 | 2/2022 | Lindsay |
| 11,253,675 B2 | 2/2022 | Fletter |
| 11,344,702 B2 | 5/2022 | Subramaniam et al. |
| 11,400,257 B2 | 8/2022 | Tierney et al. |
| 11,420,017 B2 | 8/2022 | Hilton et al. |
| 11,534,573 B2 | 12/2022 | Hannon et al. |
| 11,547,833 B2 | 1/2023 | Murray et al. |
| 11,607,524 B2 | 3/2023 | Conway et al. |
| 11,660,385 B1 | 5/2023 | Thakore et al. |
| 12,076,506 B2 | 9/2024 | Palmer |
| 12,383,700 B2 | 8/2025 | Murray et al. |
| 2001/0001443 A1 | 5/2001 | Kayerod et al. |
| 2001/0027299 A1 | 10/2001 | Yang et al. |
| 2001/0031933 A1 | 10/2001 | Cannon |
| 2001/0031952 A1 | 10/2001 | Karram et al. |
| 2001/0047147 A1 | 11/2001 | Slepian et al. |
| 2001/0054562 A1 | 12/2001 | Pettersson et al. |
| 2002/0007175 A1 | 1/2002 | Chang |
| 2002/0032406 A1 | 3/2002 | Kusleika |
| 2002/0037943 A1 | 3/2002 | Madsen |
| 2002/0045855 A1 | 4/2002 | Frassica |
| 2002/0055730 A1 | 5/2002 | Yachia et al. |
| 2002/0077611 A1 | 6/2002 | von Dyck et al. |
| 2002/0082551 A1 | 6/2002 | Yachia et al. |
| 2002/0087131 A1 | 7/2002 | Wolff et al. |
| 2002/0094322 A1 | 7/2002 | Lawson et al. |
| 2002/0095133 A1 | 7/2002 | Gillis et al. |
| 2002/0099356 A1 | 7/2002 | Unger et al. |
| 2002/0103467 A1 | 8/2002 | Kubalak |
| 2002/0107467 A1 | 8/2002 | Levin |
| 2002/0132013 A1 | 9/2002 | Moulis |
| 2002/0132049 A1 | 9/2002 | Leonard et al. |
| 2002/0133130 A1 | 9/2002 | Wilcox |
| 2002/0156440 A1 | 10/2002 | Israelsson et al. |
| 2002/0165427 A1 | 11/2002 | Yachia et al. |
| 2002/0169438 A1 | 11/2002 | Sauer |
| 2002/0182265 A1 | 12/2002 | Burrell et al. |
| 2003/0004496 A1 | 1/2003 | Tanghoj |
| 2003/0018293 A1 | 1/2003 | Tanghoj et al. |
| 2003/0018302 A1 | 1/2003 | Kavanagh et al. |
| 2003/0018322 A1 | 1/2003 | Tanghoj et al. |
| 2003/0023222 A1 | 1/2003 | Chen |
| 2003/0028174 A1 | 2/2003 | Chan et al. |
| 2003/0036802 A1 | 2/2003 | Lennox et al. |
| 2003/0055403 A1 | 3/2003 | Nestenborg et al. |
| 2003/0060807 A1 | 3/2003 | Tanghoj et al. |
| 2003/0065292 A1 | 4/2003 | Darouiche et al. |
| 2003/0083644 A1 | 5/2003 | Avaltroni |
| 2003/0130646 A1 | 7/2003 | Kubalak et al. |
| 2003/0132307 A1 | 7/2003 | Park |
| 2003/0135200 A1 | 7/2003 | Byrne |
| 2003/0163079 A1 | 8/2003 | Burnett |
| 2003/0168365 A1 | 9/2003 | Kaem |
| 2003/0195478 A1 | 10/2003 | Russo |
| 2003/0225392 A1 | 12/2003 | McMichael et al. |
| 2003/0233084 A1 | 12/2003 | Slepian et al. |
| 2004/0030301 A1 | 2/2004 | Hunter |
| 2004/0034329 A1 | 2/2004 | Mankus et al. |
| 2004/0044307 A1 | 3/2004 | Richardson et al. |
| 2004/0049152 A1 | 3/2004 | Nayak |
| 2004/0049170 A1 | 3/2004 | Snell |
| 2004/0055925 A1 | 3/2004 | Franks-Farah et al. |
| 2004/0059280 A1 | 3/2004 | Makower et al. |
| 2004/0068251 A1 | 4/2004 | Chan et al. |
| 2004/0074794 A1 | 4/2004 | Conway et al. |
| 2004/0097892 A1 | 5/2004 | Evans et al. |
| 2004/0116551 A1 | 6/2004 | Terry |
| 2004/0122382 A1 | 6/2004 | Johnson et al. |
| 2004/0127848 A1 | 7/2004 | Freyman |
| 2004/0133156 A1 | 7/2004 | Diaz et al. |
| 2004/0147871 A1 | 7/2004 | Burnett |
| 2004/0153049 A1 | 8/2004 | Hewitt et al. |
| 2004/0153051 A1 | 8/2004 | Israelsson et al. |
| 2004/0158231 A1 | 8/2004 | Tanghoj et al. |
| 2004/0163980 A1 | 8/2004 | Tanghoj et al. |
| 2004/0176747 A1 | 9/2004 | Feneley |
| 2004/0193143 A1 | 9/2004 | Sauer |
| 2004/0234572 A1 | 11/2004 | Martinod et al. |
| 2004/0236293 A1 | 11/2004 | Tanghoj et al. |
| 2004/0243104 A1 | 12/2004 | Seddon |
| 2004/0249343 A1 | 12/2004 | Cioanta |
| 2004/0254562 A1 | 12/2004 | Tanghoj et al. |
| 2004/0256264 A1 | 12/2004 | Israelsson et al. |
| 2005/0003118 A1 | 1/2005 | Takala |
| 2005/0011790 A1 | 1/2005 | Harrold |
| 2005/0015076 A1 | 1/2005 | Giebmeyer et al. |
| 2005/0031872 A1 | 2/2005 | Schmidt et al. |
| 2005/0033222 A1 | 2/2005 | Haggstrom et al. |
| 2005/0043715 A1 | 2/2005 | Nestenborg et al. |
| 2005/0049577 A1 | 3/2005 | Snell et al. |
| 2005/0059990 A1 | 3/2005 | Ayala et al. |
| 2005/0065499 A1 | 3/2005 | Douk et al. |
| 2005/0070882 A1 | 3/2005 | McBride |
| 2005/0080399 A1 | 4/2005 | Bolmsjo et al. |
| 2005/0096582 A1 | 5/2005 | Burnett |
| 2005/0101923 A1 | 5/2005 | Elson et al. |
| 2005/0101924 A1 | 5/2005 | Elson et al. |
| 2005/0107735 A1 | 5/2005 | Lennox et al. |
| 2005/0107771 A1 | 5/2005 | Finkbeiner |
| 2005/0109648 A1 | 5/2005 | Kerzman et al. |
| 2005/0137522 A1 | 6/2005 | Aoki |
| 2005/0137582 A1 | 6/2005 | Kull-Osterlin et al. |
| 2005/0143690 A1 | 6/2005 | High |
| 2005/0148950 A1 | 7/2005 | Windheuser et al. |
| 2005/0177104 A1 | 8/2005 | Conway |
| 2005/0197531 A1 | 9/2005 | Cabiri et al. |
| 2005/0199521 A1 | 9/2005 | Givens |
| 2005/0209580 A1 | 9/2005 | Freyman |
| 2005/0214443 A1 | 9/2005 | Madsen |
| 2005/0245901 A1 | 11/2005 | Floyd |
| 2005/0251108 A1 | 11/2005 | Frassica |
| 2005/0256447 A1 | 11/2005 | Richardson et al. |
| 2005/0273034 A1 | 12/2005 | Burnett |
| 2005/0282977 A1 | 12/2005 | Stempel et al. |
| 2005/0283136 A1 | 12/2005 | Skarda |
| 2006/0025753 A1 | 2/2006 | Kubalak et al. |
| 2006/0027854 A1 | 2/2006 | Kim et al. |
| 2006/0030864 A1 | 2/2006 | Kennedy, et al. |
| 2006/0036208 A1 | 2/2006 | Burnett |
| 2006/0041246 A1 | 2/2006 | Provost-tine et al. |
| 2006/0054557 A1 | 3/2006 | Hori et al. |
| 2006/0058777 A1 | 3/2006 | Nielsen |
| 2006/0064065 A1 | 3/2006 | Russo |
| 2006/0079835 A1 | 4/2006 | Frassica |
| 2006/0079854 A1 | 4/2006 | Kay et al. |
| 2006/0100511 A1 | 5/2006 | Eriksen |
| 2006/0122566 A1 | 6/2006 | Huang et al. |
| 2006/0122568 A1 | 6/2006 | Elson et al. |
| 2006/0142737 A1 | 6/2006 | Tanghoj |
| 2006/0172096 A1 | 8/2006 | Kyle et al. |
| 2006/0184112 A1 | 8/2006 | Horn et al. |
| 2006/0184145 A1 | 8/2006 | Ciok et al. |
| 2006/0189962 A1 | 8/2006 | Burtoft |
| 2006/0196783 A1 | 9/2006 | Bruun et al. |
| 2006/0200079 A1 | 9/2006 | Magnusson |

(56)  References Cited

U.S. PATENT DOCUMENTS

| | | |
|---|---|---|
| 2006/0229576 A1 | 10/2006 | Conway et al. |
| 2006/0240069 A1 | 10/2006 | Utas et al. |
| 2006/0263404 A1 | 11/2006 | Nielsen et al. |
| 2006/0271019 A1 | 11/2006 | Stoller et al. |
| 2006/0276894 A1 | 12/2006 | Finley |
| 2006/0278546 A1 | 12/2006 | State et al. |
| 2006/0293642 A1 | 12/2006 | Israelsson et al. |
| 2007/0005024 A1 | 1/2007 | Weber et al. |
| 2007/0005041 A1 | 1/2007 | Frassica et al. |
| 2007/0010798 A1 | 1/2007 | Stoller et al. |
| 2007/0016168 A1 | 1/2007 | Conway |
| 2007/0016169 A1 | 1/2007 | Utas et al. |
| 2007/0049879 A1 | 3/2007 | Gutierrez |
| 2007/0059350 A1 | 3/2007 | Kennedy et al. |
| 2007/0066963 A1 | 3/2007 | Tanghoj |
| 2007/0084749 A1 | 4/2007 | Demelo et al. |
| 2007/0088330 A1 | 4/2007 | House |
| 2007/0106233 A1 | 5/2007 | Huang et al. |
| 2007/0108076 A1 | 5/2007 | Miller et al. |
| 2007/0112327 A1 | 5/2007 | Yun et al. |
| 2007/0112333 A1* | 5/2007 | Hoang ................. A61M 39/20 |
| | | 604/533 |
| 2007/0149929 A1 | 6/2007 | Utas et al. |
| 2007/0161971 A1 | 7/2007 | House |
| 2007/0197957 A1 | 8/2007 | Hunter et al. |
| 2007/0218102 A1 | 9/2007 | Chudzik et al. |
| 2007/0225635 A1 | 9/2007 | Lynn |
| 2007/0225649 A1 | 9/2007 | House |
| 2007/0225687 A1 | 9/2007 | House |
| 2007/0244449 A1 | 10/2007 | Najafi et al. |
| 2007/0287800 A1 | 12/2007 | Acquarulo et al. |
| 2007/0289887 A1 | 12/2007 | Murray et al. |
| 2008/0006554 A1 | 1/2008 | Duffy et al. |
| 2008/0015518 A1 | 1/2008 | Huang et al. |
| 2008/0015527 A1 | 1/2008 | House |
| 2008/0021382 A1 | 1/2008 | Freyman |
| 2008/0027414 A1 | 1/2008 | Tanghoj et al. |
| 2008/0033471 A1 | 2/2008 | Paz et al. |
| 2008/0050446 A1 | 2/2008 | Ziegler et al. |
| 2008/0051762 A1 | 2/2008 | Tsukada et al. |
| 2008/0051763 A1 | 2/2008 | Frojd |
| 2008/0063324 A1 | 3/2008 | Bernard et al. |
| 2008/0077099 A1 | 3/2008 | House |
| 2008/0082051 A1 | 4/2008 | Miller et al. |
| 2008/0085949 A1 | 4/2008 | McGhee |
| 2008/0086008 A1 | 4/2008 | Lhermitte et al. |
| 2008/0091145 A1 | 4/2008 | House |
| 2008/0097362 A1 | 4/2008 | Mosler et al. |
| 2008/0097394 A1 | 4/2008 | Lampropoulos et al. |
| 2008/0097411 A1 | 4/2008 | House |
| 2008/0103464 A1 | 5/2008 | Mosler et al. |
| 2008/0119803 A1 | 5/2008 | Lund |
| 2008/0125513 A1 | 5/2008 | Kristiansen |
| 2008/0140010 A1 | 6/2008 | Kennedy et al. |
| 2008/0140052 A1 | 6/2008 | Moller et al. |
| 2008/0171973 A1 | 7/2008 | House |
| 2008/0171998 A1 | 7/2008 | House |
| 2008/0172016 A1 | 7/2008 | House |
| 2008/0172040 A1 | 7/2008 | Smith |
| 2008/0172042 A1 | 7/2008 | House |
| 2008/0177217 A1 | 7/2008 | Polaschegg |
| 2008/0179208 A1 | 7/2008 | Murray et al. |
| 2008/0183262 A1 | 7/2008 | Dowling |
| 2008/0193497 A1 | 8/2008 | Samuelsen et al. |
| 2008/0200907 A1 | 8/2008 | Nestenborg |
| 2008/0215021 A1 | 9/2008 | Cisko, Jr. et al. |
| 2008/0243081 A1 | 10/2008 | Nance et al. |
| 2008/0243091 A1 | 10/2008 | Humphreys et al. |
| 2008/0249467 A1 | 10/2008 | Burnett et al. |
| 2008/0249482 A1 | 10/2008 | Erez |
| 2008/0275463 A1 | 11/2008 | High |
| 2008/0279907 A1 | 11/2008 | Ash et al. |
| 2008/0281291 A1 | 11/2008 | Tihon et al. |
| 2009/0000970 A1 | 1/2009 | Bordeau et al. |
| 2009/0005725 A1 | 1/2009 | Shorey |
| 2009/0012208 A1 | 1/2009 | Madsen et al. |
| 2009/0024111 A1 | 1/2009 | Borodulin et al. |
| 2009/0043287 A1 | 2/2009 | Mosler et al. |
| 2009/0048537 A1 | 2/2009 | Lydon et al. |
| 2009/0048570 A1 | 2/2009 | Jensen |
| 2009/0054876 A1 | 2/2009 | Borodulin et al. |
| 2009/0062754 A1 | 3/2009 | Tang |
| 2009/0065605 A1 | 3/2009 | Roche et al. |
| 2009/0071851 A1 | 3/2009 | Maki et al. |
| 2009/0099532 A1 | 4/2009 | Cuevas et al. |
| 2009/0101531 A1 | 4/2009 | Nordholm et al. |
| 2009/0112171 A1 | 4/2009 | Ng et al. |
| 2009/0131917 A1 | 5/2009 | Kavanagh et al. |
| 2009/0137985 A1 | 5/2009 | Tanghoej et al. |
| 2009/0137986 A1 | 5/2009 | Golden et al. |
| 2009/0149837 A1 | 6/2009 | Tanghoj et al. |
| 2009/0156882 A1 | 6/2009 | Chi Sing et al. |
| 2009/0163884 A1 | 6/2009 | Kull-Osterlin et al. |
| 2009/0200187 A1 | 8/2009 | Nestenborg et al. |
| 2009/0208368 A1 | 8/2009 | Waldrep et al. |
| 2009/0221992 A1 | 9/2009 | Hannon et al. |
| 2009/0299334 A1 | 12/2009 | Nishtala et al. |
| 2009/0314795 A1 | 12/2009 | Rapko et al. |
| 2009/0318900 A1 | 12/2009 | Tanghoj et al. |
| 2010/0010086 A1 | 1/2010 | Ash et al. |
| 2010/0030197 A1 | 2/2010 | House |
| 2010/0036363 A1 | 2/2010 | Watanabe et al. |
| 2010/0047123 A1* | 2/2010 | Solomon ............... A61M 39/20 |
| | | 422/28 |
| 2010/0086580 A1 | 4/2010 | Nyman et al. |
| 2010/0133172 A1 | 6/2010 | Song et al. |
| 2010/0152686 A1 | 6/2010 | Ryder et al. |
| 2010/0155268 A1 | 6/2010 | Murray et al. |
| 2010/0198195 A1 | 8/2010 | Nishtala et al. |
| 2010/0228233 A1 | 9/2010 | Kahn |
| 2010/0256576 A1 | 10/2010 | Aggarwal et al. |
| 2010/0258568 A1 | 10/2010 | Frederiksen et al. |
| 2010/0263327 A1 | 10/2010 | Murray et al. |
| 2010/0324540 A1 | 12/2010 | Paulen et al. |
| 2011/0028943 A1 | 2/2011 | Lawson et al. |
| 2011/0056852 A1 | 3/2011 | Frojd |
| 2011/0059874 A1 | 3/2011 | Rooijmans et al. |
| 2011/0060317 A1 | 3/2011 | Frojd |
| 2011/0114520 A1 | 5/2011 | Matthison-Hansen |
| 2011/0127186 A1 | 6/2011 | Enns et al. |
| 2011/0137243 A1 | 6/2011 | Hossainy et al. |
| 2011/0137296 A1 | 6/2011 | Tanghoj |
| 2011/0144579 A1 | 6/2011 | Elton |
| 2011/0147238 A1 | 6/2011 | Tanghoej et al. |
| 2011/0152843 A1 | 6/2011 | Wedlin et al. |
| 2011/0160704 A1* | 6/2011 | Park ................... A61M 25/0111 |
| | | 604/528 |
| 2011/0178507 A1 | 7/2011 | Bracken et al. |
| 2011/0184386 A1 | 7/2011 | House |
| 2011/0213025 A1 | 9/2011 | Finch, Jr. |
| 2011/0224653 A1 | 9/2011 | Torstensen |
| 2011/0284409 A1 | 11/2011 | Murray et al. |
| 2011/0295239 A1 | 12/2011 | Gustavsson |
| 2012/0037525 A1 | 2/2012 | Peck et al. |
| 2012/0168324 A1 | 7/2012 | Carleo |
| 2012/0179102 A1 | 7/2012 | Blanchard et al. |
| 2012/0179144 A1 | 7/2012 | Carleo |
| 2012/0193255 A1 | 8/2012 | Lareau et al. |
| 2012/0219742 A1 | 8/2012 | Gravesen et al. |
| 2012/0228165 A1 | 9/2012 | Murray et al. |
| 2012/0239005 A1 | 9/2012 | Conway et al. |
| 2012/0271101 A1 | 10/2012 | Tan |
| 2012/0284991 A1 | 11/2012 | Kusz et al. |
| 2012/0308805 A1 | 12/2012 | Sella |
| 2012/0310210 A1 | 12/2012 | Campbell et al. |
| 2012/0316515 A1 | 12/2012 | Terry |
| 2012/0330255 A1 | 12/2012 | Carlin |
| 2013/0006226 A1 | 1/2013 | Hong et al. |
| 2013/0037306 A1 | 2/2013 | Kim |
| 2013/0048516 A1 | 2/2013 | Nishtala et al. |
| 2013/0077899 A1 | 3/2013 | Odabashian et al. |
| 2013/0085469 A1 | 4/2013 | Polaschegg |
| 2013/0131647 A1 | 5/2013 | Nielsen |
| 2013/0138083 A1 | 5/2013 | Tennican |

(56) References Cited

U.S. PATENT DOCUMENTS

| | | |
|---|---|---|
| 2013/0138088 A1 | 5/2013 | Nielsen |
| 2013/0146599 A1 | 6/2013 | Murray et al. |
| 2013/0153446 A1 | 6/2013 | Utas et al. |
| 2013/0161208 A1 | 6/2013 | Gustavsson |
| 2013/0161227 A1 | 6/2013 | Gustavsson |
| 2013/0186778 A1 | 7/2013 | Terry |
| 2013/0218136 A1 | 8/2013 | Tanghoej et al. |
| 2013/0231641 A1 | 9/2013 | Gustavsson |
| 2013/0253426 A1 | 9/2013 | Campbell et al. |
| 2013/0261608 A1 | 10/2013 | Tanghoj |
| 2013/0264227 A1 | 10/2013 | Frojd |
| 2013/0289537 A1 | 10/2013 | Schertiger et al. |
| 2014/0066904 A1 | 3/2014 | Young |
| 2014/0066905 A1 | 3/2014 | Young |
| 2014/0193474 A1 | 7/2014 | Babcock et al. |
| 2014/0194857 A1 | 7/2014 | Eilat |
| 2014/0224678 A1 | 8/2014 | Schertiger et al. |
| 2014/0262859 A1 | 9/2014 | Knapp et al. |
| 2014/0271351 A1 | 9/2014 | Nielsen et al. |
| 2014/0271400 A1 | 9/2014 | Cheng et al. |
| 2014/0287172 A1 | 9/2014 | Finley et al. |
| 2015/0001107 A1 | 1/2015 | Gustavsson |
| 2015/0018962 A1 | 1/2015 | Matsumoto et al. |
| 2015/0051587 A1 | 2/2015 | Rolsted et al. |
| 2015/0068927 A1 | 3/2015 | McBurney et al. |
| 2015/0105756 A1 | 4/2015 | O'Brien et al. |
| 2015/0126975 A1 | 5/2015 | Wuthier |
| 2015/0132468 A1 | 5/2015 | Cage et al. |
| 2015/0133898 A1 | 5/2015 | Murray et al. |
| 2015/0202405 A1 | 7/2015 | Schertiger et al. |
| 2015/0231377 A1 | 8/2015 | Tierney et al. |
| 2015/0238726 A1 | 8/2015 | Terry |
| 2015/0258305 A1 | 9/2015 | Dye |
| 2015/0265801 A1 | 9/2015 | Rostami |
| 2015/0273116 A1 | 10/2015 | Knapp et al. |
| 2015/0273183 A1 | 10/2015 | Foley et al. |
| 2015/0297861 A1 | 10/2015 | Passalaqua et al. |
| 2015/0297862 A1 | 10/2015 | Sadik et al. |
| 2015/0306342 A1 | 10/2015 | Rostami et al. |
| 2015/0314103 A1 | 11/2015 | Hannon et al. |
| 2015/0335823 A1 | 11/2015 | Weikart et al. |
| 2015/0335854 A1 | 11/2015 | Dvarsater et al. |
| 2015/0335856 A1 | 11/2015 | Utas et al. |
| 2015/0335872 A1 | 11/2015 | Yang et al. |
| 2015/0343171 A1 | 12/2015 | Hannon |
| 2015/0352324 A1 | 12/2015 | Palmer |
| 2015/0359996 A1 | 12/2015 | Arora et al. |
| 2016/0001037 A1 | 1/2016 | Hong et al. |
| 2016/0038652 A1 | 2/2016 | Gilman |
| 2016/0038713 A1 | 2/2016 | Kearns et al. |
| 2016/0120688 A1 | 5/2016 | Lee |
| 2016/0166822 A1 | 6/2016 | Dodson et al. |
| 2016/0175488 A1 | 6/2016 | Klein et al. |
| 2016/0184551 A1 | 6/2016 | Nyman et al. |
| 2016/0193447 A1 | 7/2016 | Matthiassen |
| 2016/0220784 A1 | 8/2016 | Palmer |
| 2016/0317715 A1 | 11/2016 | Rostami et al. |
| 2016/0325088 A1* | 11/2016 | Nordquist .............. A61B 90/70 |
| 2016/0325089 A1* | 11/2016 | Burkholz .............. A61M 5/001 |
| 2017/0173300 A1 | 6/2017 | Hannon et al. |
| 2017/0217658 A1 | 8/2017 | Whitehurst |
| 2017/0296704 A1 | 10/2017 | Knapp et al. |
| 2017/0326334 A1 | 11/2017 | Terry |
| 2018/0021481 A1 | 1/2018 | Yin et al. |
| 2018/0050173 A1 | 2/2018 | Kearns |
| 2018/0071486 A1 | 3/2018 | O'Flynn |
| 2018/0104444 A1 | 4/2018 | Yin et al. |
| 2018/0110961 A1 | 4/2018 | Steindahl et al. |
| 2018/0163152 A1 | 6/2018 | Luo et al. |
| 2018/0169377 A1 | 6/2018 | Hickmott et al. |
| 2019/0047766 A1 | 2/2019 | Brooks et al. |
| 2019/0083746 A1 | 3/2019 | Murray et al. |
| 2019/0105462 A1 | 4/2019 | Schertiger |
| 2019/0110879 A1 | 4/2019 | Camp et al. |
| 2019/0126004 A1 | 5/2019 | O'Brien et al. |
| 2019/0151605 A1 | 5/2019 | McMenamin et al. |
| 2019/0151610 A1 | 5/2019 | Fletter |
| 2019/0216985 A1* | 7/2019 | Mcburney ............. A61L 27/505 |
| 2019/0255280 A1 | 8/2019 | Palmer |
| 2019/0321593 A1* | 10/2019 | Crawford .......... A61M 25/0097 |
| 2019/0358435 A1 | 11/2019 | Andersin et al. |
| 2019/0381272 A1 | 12/2019 | Terry |
| 2020/0001043 A1 | 1/2020 | Heneghan et al. |
| 2020/0016380 A1 | 1/2020 | Murray et al. |
| 2020/0031550 A1 | 1/2020 | Douglas et al. |
| 2020/0115102 A1 | 4/2020 | Hawry |
| 2020/0155261 A1 | 5/2020 | O'Flynn et al. |
| 2020/0155794 A1* | 5/2020 | Ziebol ................... A61M 39/16 |
| 2020/0155796 A1 | 5/2020 | Hannon et al. |
| 2020/0171218 A1 | 6/2020 | Dong et al. |
| 2020/0179647 A1 | 6/2020 | Conway et al. |
| 2020/0188631 A1 | 6/2020 | Hannon et al. |
| 2020/0222659 A1 | 7/2020 | Schertiger et al. |
| 2020/0230349 A1 | 7/2020 | McMenamin et al. |
| 2020/0238048 A1 | 7/2020 | Palmer |
| 2020/0246594 A1 | 8/2020 | Miller |
| 2020/0281751 A1 | 9/2020 | Schreck et al. |
| 2020/0282177 A1 | 9/2020 | Farrell |
| 2020/0345977 A1 | 11/2020 | Hickmott et al. |
| 2020/0361076 A1 | 11/2020 | Richart |
| 2020/0383822 A1 | 12/2020 | Palmer |
| 2020/0391005 A1 | 12/2020 | Murray et al. |
| 2020/0398023 A1 | 12/2020 | Conway et al. |
| 2020/0398024 A1 | 12/2020 | Fletter et al. |
| 2021/0008361 A1* | 1/2021 | Aronson ............... A61M 39/10 |
| 2021/0100979 A1 | 4/2021 | Donnelly et al. |
| 2021/0113808 A1 | 4/2021 | Yin et al. |
| 2021/0187238 A1 | 6/2021 | O'Brien et al. |
| 2021/0212808 A1 | 7/2021 | Wu et al. |
| 2021/0283367 A1 | 9/2021 | Peters |
| 2021/0290894 A1 | 9/2021 | Palmer |
| 2021/0290895 A1* | 9/2021 | Nielsen ............. A61M 25/0017 |
| 2021/0402135 A1 | 12/2021 | McMenamin et al. |
| 2022/0023585 A1 | 1/2022 | Schertiger et al. |
| 2022/0054295 A1* | 2/2022 | Becker ................ A61M 25/002 |
| 2022/0112018 A1 | 4/2022 | Montano et al. |
| 2022/0117850 A1 | 4/2022 | Romeo et al. |
| 2022/0142810 A1 | 5/2022 | Whittaker |
| 2022/0241549 A1* | 8/2022 | Murray ............... A61M 25/002 |
| 2022/0273837 A1 | 9/2022 | Paul et al. |
| 2022/0362536 A1 | 11/2022 | Nguyen et al. |
| 2023/0058911 A1 | 2/2023 | Nabors et al. |
| 2023/0072221 A1 | 3/2023 | Donnelly et al. |
| 2023/0073264 A1 | 3/2023 | Kandrac et al. |
| 2023/0075906 A1 | 3/2023 | Piashevich et al. |
| 2023/0077075 A1 | 3/2023 | Kandrac et al. |
| 2023/0166073 A1 | 6/2023 | Radmer |
| 2023/0293848 A1 | 9/2023 | Legaspi et al. |
| 2023/0364379 A1 | 11/2023 | Hughett, Sr. et al. |
| 2024/0108850 A1 | 4/2024 | Yin et al. |
| 2024/0269426 A1 | 8/2024 | Siddiqui |
| 2024/0325685 A1 | 10/2024 | Daw et al. |
| 2024/0342332 A1 | 10/2024 | Paras |
| 2025/0082897 A1 | 3/2025 | Pfleger |
| 2025/0114231 A1 | 4/2025 | Legaspi et al. |
| 2025/0288774 A1 | 9/2025 | Kulkarni et al. |
| 2025/0289618 A1 | 9/2025 | Simonsen et al. |
| 2025/0325785 A1 | 10/2025 | Kulkarni et al. |

FOREIGN PATENT DOCUMENTS

| | | |
|---|---|---|
| AU | 2022354188 A1 | 3/2024 |
| BR | PI0803737 A2 | 1/2010 |
| CA | 763930 A | 7/1967 |
| CA | 2770300 A1 | 2/2011 |
| CA | 2769026 C | 4/2015 |
| CA | 3083014 A1 | 5/2019 |
| CN | 1106744 A | 8/1995 |
| CN | 2532840 Y | 1/2003 |
| CN | 2907580 Y | 6/2007 |
| CN | 101035573 A | 9/2007 |
| CN | 101365501 A | 2/2009 |
| CN | 102939127 A | 2/2013 |
| CN | 102939129 A | 2/2013 |

(56) References Cited

FOREIGN PATENT DOCUMENTS

| CN | 102973986 | A | 3/2013 |
|---|---|---|---|
| CN | 102973987 | A | 3/2013 |
| CN | 107088243 | A | 8/2017 |
| CN | 111870742 | A | 11/2020 |
| CN | 217015042 | U | 7/2022 |
| CN | 116056746 | A | 5/2023 |
| DE | 352014 | C | 4/1922 |
| DE | 1913976 | U | 4/1965 |
| DE | 4135502 | C1 | 2/1993 |
| DE | 4303899 | A1 | 8/1994 |
| DE | 19826746 | C1 | 11/1999 |
| DE | 10038521 | A1 | 2/2002 |
| DE | 10213411 | A1 | 10/2003 |
| DE | 10259002 | A1 | 10/2003 |
| DE | 10334372 | A1 | 2/2005 |
| DE | 202005009946 U1 * | 9/2005 | .............. A61F 5/451 |
| DE | 202005009947 | U1 | 9/2005 |
| DE | 102007018275 | A1 | 3/2008 |
| DE | 102009025347 | A1 | 12/2010 |
| DE | 202012000538 | U1 | 3/2012 |
| DE | 202011107059 | U1 | 1/2013 |
| DE | 202013002466 | U1 | 3/2013 |
| DE | 102011085864 | A1 | 5/2013 |
| DE | 102012000844 | A1 | 7/2013 |
| DE | 102016120294 A1 * | 4/2018 | ......... A61M 25/002 |
| DE | 112018000170 | T5 | 10/2019 |
| EP | 0055023 | A2 | 6/1982 |
| EP | 0182409 | A1 | 5/1986 |
| EP | 0184629 | A2 | 6/1986 |
| EP | 0187846 | A1 | 7/1986 |
| EP | 0193406 | A2 | 9/1986 |
| EP | 0218203 | A1 | 4/1987 |
| EP | 0236458 | A1 | 9/1987 |
| EP | 247559 | A1 | 12/1987 |
| EP | 0252918 | A1 | 1/1988 |
| EP | 0298634 | A1 | 1/1989 |
| EP | 0303487 | A2 | 2/1989 |
| EP | 0335564 | A1 | 10/1989 |
| EP | 0352043 | A1 | 1/1990 |
| EP | 0390720 | A1 | 10/1990 |
| EP | 0407218 | A1 | 1/1991 |
| EP | 0217771 | B1 | 12/1991 |
| EP | 0471553 | A1 | 2/1992 |
| EP | 0479935 | A1 | 4/1992 |
| EP | 0528965 | A1 | 3/1993 |
| EP | 0553960 | A1 | 8/1993 |
| EP | 0590104 | A1 | 4/1994 |
| EP | 0598191 | A1 | 5/1994 |
| EP | 0663196 | A1 | 7/1995 |
| EP | 0677299 | A1 | 10/1995 |
| EP | 0680895 | A1 | 11/1995 |
| EP | 0685179 | A1 | 12/1995 |
| EP | 0699086 | A1 | 3/1996 |
| EP | 0767639 | A1 | 4/1997 |
| EP | 0768069 | A1 | 4/1997 |
| EP | 0795339 | A1 | 9/1997 |
| EP | 0815037 | A1 | 1/1998 |
| EP | 0909249 | A1 | 4/1999 |
| EP | 0923398 | A1 | 6/1999 |
| EP | 0935478 | A1 | 8/1999 |
| EP | 0959930 | A1 | 12/1999 |
| EP | 0977610 | A2 | 2/2000 |
| EP | 1018323 | A1 | 7/2000 |
| EP | 1023882 | A1 | 8/2000 |
| EP | 1047360 | A1 | 11/2000 |
| EP | 1115450 | A1 | 7/2001 |
| EP | 1131022 | A1 | 9/2001 |
| EP | 1175355 | A1 | 1/2002 |
| EP | 1237615 | A1 | 9/2002 |
| EP | 1245205 | A2 | 10/2002 |
| EP | 1308146 | A1 | 5/2003 |
| EP | 1321163 | A1 | 6/2003 |
| EP | 1347723 | A1 | 10/2003 |
| EP | 1406690 | A2 | 4/2004 |
| EP | 1409060 | A2 | 4/2004 |
| EP | 1090656 | B1 | 5/2004 |
| EP | 1420846 | A1 | 5/2004 |
| EP | 1420847 | A2 | 5/2004 |
| EP | 1427467 | A2 | 6/2004 |
| EP | 1485158 | A2 | 12/2004 |
| EP | 1498151 | A2 | 1/2005 |
| EP | 1567219 | A1 | 8/2005 |
| EP | 1578308 | A1 | 9/2005 |
| EP | 1145729 | B1 | 11/2005 |
| EP | 1606196 | A2 | 12/2005 |
| EP | 1615690 | A1 | 1/2006 |
| EP | 1629799 | A1 | 3/2006 |
| EP | 1629860 | | 3/2006 |
| EP | 1641510 | A1 | 4/2006 |
| EP | 1642610 | | 4/2006 |
| EP | 1642611 | | 4/2006 |
| EP | 1695678 | A1 | 8/2006 |
| EP | 1357868 | B1 | 9/2006 |
| EP | 1723980 | A2 | 11/2006 |
| EP | 1744803 | A2 | 1/2007 |
| EP | 1757251 | A2 | 2/2007 |
| EP | 1788990 | A1 | 5/2007 |
| EP | 1793938 | A1 | 6/2007 |
| EP | 1799163 | A1 | 6/2007 |
| EP | 1824534 | | 8/2007 |
| EP | 11824549 | | 8/2007 |
| EP | 1858575 | | 11/2007 |
| EP | 1904003 | | 4/2008 |
| EP | 1948279 | | 7/2008 |
| EP | 1955683 | A | 8/2008 |
| EP | 2060296 | | 5/2009 |
| EP | 2106821 | | 10/2009 |
| EP | 2275058 | | 1/2011 |
| EP | 2292293 | A1 | 3/2011 |
| EP | 2292294 | A1 | 3/2011 |
| EP | 2308542 | A1 | 4/2011 |
| EP | 2423125 | A1 | 2/2012 |
| EP | 2423127 | A1 | 2/2012 |
| EP | P423126 | A1 | 2/2012 |
| EP | 2450076 | A1 | 5/2012 |
| EP | 2459264 | A1 | 6/2012 |
| EP | 2464411 | A1 | 6/2012 |
| EP | 2468347 | A1 | 6/2012 |
| EP | 2500056 | A2 | 9/2012 |
| EP | 2515988 | A1 | 10/2012 |
| EP | 1786501 | B1 | 11/2012 |
| EP | 2542291 | A1 | 1/2013 |
| EP | 1578468 | B1 | 4/2013 |
| EP | 2574354 | A1 | 4/2013 |
| EP | 2424470 | B1 | 8/2013 |
| EP | 2504054 | B1 | 9/2013 |
| EP | 2644224 | A2 | 10/2013 |
| EP | 1962937 | | 8/2014 |
| EP | 2774648 | A1 | 9/2014 |
| EP | 2515985 | B1 | 12/2014 |
| EP | 2686054 | B1 | 12/2014 |
| EP | 2908897 | A1 | 8/2015 |
| EP | 2898918 | A3 | 9/2015 |
| EP | 2914222 | A1 | 9/2015 |
| EP | 2967968 | A1 | 1/2016 |
| EP | 1852139 | | 5/2016 |
| EP | 2777747 | B1 | 5/2017 |
| EP | 3199130 | A1 | 8/2017 |
| EP | 3231471 | A1 | 10/2017 |
| EP | 3078393 | B1 | 11/2017 |
| EP | 3272385 | A1 | 1/2018 |
| EP | 3222316 | B1 | 5/2018 |
| EP | 3352831 | A1 | 8/2018 |
| EP | 2782629 | B1 | 4/2019 |
| EP | 3313494 | B1 | 5/2019 |
| EP | 3478353 | A1 | 5/2019 |
| EP | 2826514 | B1 | 6/2019 |
| EP | 3490654 | A1 | 6/2019 |
| EP | 2946803 | B1 | 7/2019 |
| EP | 3551103 | A1 | 10/2019 |
| EP | 3566739 | A1 | 11/2019 |
| EP | 3570925 | A1 | 11/2019 |
| EP | 3092024 | B1 | 12/2019 |
| EP | 3583972 | A2 | 12/2019 |

(56) References Cited

FOREIGN PATENT DOCUMENTS

| EP | 3388103 B1 | 1/2020 |
| EP | 3590573 A1 | 1/2020 |
| EP | 3079752 B1 | 4/2020 |
| EP | 3100758 B1 | 4/2020 |
| EP | 2826515 B1 | 5/2020 |
| EP | 3079748 B1 | 5/2020 |
| EP | 3651844 A1 | 5/2020 |
| EP | 2651485 B1 | 6/2020 |
| EP | 3038690 B1 | 7/2020 |
| EP | 3119464 B1 | 9/2020 |
| EP | 3132823 B1 | 9/2020 |
| EP | 3299056 B1 | 9/2020 |
| EP | 3701993 A1 | 9/2020 |
| EP | 3709940 A1 | 9/2020 |
| EP | 3710095 A1 | 9/2020 |
| EP | 3711806 A1 | 9/2020 |
| EP | 3711807 A1 * | 9/2020 | .......... A61M 25/002 |
| EP | 3711808 A1 | 9/2020 |
| EP | 3713632 A2 | 9/2020 |
| EP | 3392167 B1 | 10/2020 |
| EP | 2468346 B1 | 11/2020 |
| EP | 3077031 B1 | 11/2020 |
| EP | 3738640 A1 | 11/2020 |
| EP | 3769803 A2 | 1/2021 |
| EP | 2995268 B1 | 3/2021 |
| EP | 3793627 A1 | 3/2021 |
| EP | 2968833 B1 | 5/2021 |
| EP | 3952973 A1 | 2/2022 |
| EP | 3082929 B1 | 3/2022 |
| EP | 3310421 B1 | 3/2022 |
| EP | 3725355 B1 | 5/2022 |
| EP | 2688629 B1 | 12/2022 |
| ES | 2645658 B1 | 10/2018 |
| FR | 1558162 A | 2/1969 |
| FR | 96086 E | 5/1972 |
| FR | 2127704 A5 | 10/1972 |
| FR | 2351634 A1 | 12/1977 |
| FR | 2731345 A1 | 9/1996 |
| FR | 2794638 A1 | 12/2000 |
| FR | 2855399 A1 | 12/2004 |
| FR | 3042716 B1 | 10/2021 |
| GB | 322426 A | 12/1929 |
| GB | 1131865 A | 10/1968 |
| GB | 2007507 A | 5/1979 |
| GB | 2106784 A | 4/1983 |
| GB | 2150938 A | 7/1985 |
| GB | 2187670 A | 9/1987 |
| GB | 2231801 A | 11/1990 |
| GB | 2239804 A | 7/1991 |
| GB | 2319507 | 5/1998 |
| GB | 2284764 B | 8/1998 |
| GB | 2427362 B | 9/2008 |
| GB | 2462267 A | 2/2010 |
| GB | 2469824 B | 8/2011 |
| GB | 2532459 B | 12/2016 |
| GB | 2565585 A | 2/2019 |
| GB | 2561843 B | 9/2021 |
| JP | S5512265 B2 | 3/1980 |
| JP | S59218157 A | 12/1984 |
| JP | S59228856 A | 12/1984 |
| JP | H0218157 A | 1/1990 |
| JP | H09206370 A | 8/1997 |
| JP | H10151094 A | 6/1998 |
| JP | H10277144 A | 10/1998 |
| JP | 2001500414 A | 1/2001 |
| JP | 200150329 A | 2/2001 |
| JP | 2002530148 A | 9/2002 |
| JP | 2002282275 A | 10/2002 |
| JP | 2002543885 A | 12/2002 |
| JP | 2007501656 A | 2/2007 |
| JP | 2007167158 A | 7/2007 |
| JP | 2008-51549 A | 3/2008 |
| JP | 2008508077 A | 3/2008 |
| JP | 2008526377 A | 7/2008 |
| JP | 2009125583 A | 6/2009 |

| JP | 2010538106 A | 12/2010 |
| JP | 2011510110 A | 3/2011 |
| JP | 2013500125 A | 1/2013 |
| JP | 2013515572 | 5/2013 |
| KR | 1020160035437 A | 3/2016 |
| RU | 2009105497 A | 8/2010 |
| WO | 1984001102 A1 | 3/1984 |
| WO | 198401296 A1 | 4/1984 |
| WO | 1986000816 A1 | 2/1986 |
| WO | 1986006284 A1 | 11/1986 |
| WO | 1987001582 A1 | 3/1987 |
| WO | 1989003232 A1 | 4/1989 |
| WO | 1989009626 A1 | 10/1989 |
| WO | 1990004431 A1 | 5/1990 |
| WO | 1991005577 A1 | 5/1991 |
| WO | 1991010466 A1 | 7/1991 |
| WO | 1991017728 A1 | 11/1991 |
| WO | 1992008426 A1 | 5/1992 |
| WO | 1992010220 A1 | 6/1992 |
| WO | 1992011826 A1 | 7/1992 |
| WO | 1992019192 A1 | 11/1992 |
| WO | 1993000054 A1 | 1/1993 |
| WO | 9311821 A1 | 6/1993 |
| WO | 9314806 A1 | 8/1993 |
| WO | 1994006377 A1 | 3/1994 |
| WO | 1994016747 A1 | 8/1994 |
| WO | 1994026215 A1 | 11/1994 |
| WO | 1995008968 A1 | 4/1995 |
| WO | 1995009667 A1 | 4/1995 |
| WO | 1995017862 A1 | 7/1995 |
| WO | 1995034253 A1 | 12/1995 |
| WO | 1996000541 A1 | 1/1996 |
| WO | 1996004119 A1 | 2/1996 |
| WO | 9607447 A1 | 3/1996 |
| WO | 1996019254 A1 | 6/1996 |
| WO | 1996026688 A1 | 9/1996 |
| WO | 1996030277 A1 | 10/1996 |
| WO | 1996034587 A1 | 11/1996 |
| WO | 9641653 A1 | 12/1996 |
| WO | 1996038192 A1 | 12/1996 |
| WO | 1996039096 A1 | 12/1996 |
| WO | 1997025947 A1 | 7/1997 |
| WO | 1997026937 A1 | 7/1997 |
| WO | 1997041811 A1 | 11/1997 |
| WO | 1998006642 | 2/1998 |
| WO | 1998011932 | 3/1998 |
| WO | 1998019729 | 5/1998 |
| WO | 9846176 A1 | 10/1998 |
| WO | 1999007313 A1 | 2/1999 |
| WO | 1999030761 A1 | 6/1999 |
| WO | 1999036009 A1 | 7/1999 |
| WO | 2000016843 | 3/2000 |
| WO | 2000025848 A2 | 5/2000 |
| WO | 0030696 A1 | 6/2000 |
| WO | 2000030575 A1 | 6/2000 |
| WO | 2000047494 A1 | 8/2000 |
| WO | 2001043807 A1 | 6/2001 |
| WO | 0152763 A1 | 7/2001 |
| WO | 2001093935 A1 | 12/2001 |
| WO | 2002036192 A1 | 5/2002 |
| WO | 2002053070 A1 | 7/2002 |
| WO | 2002060361 A2 | 8/2002 |
| WO | 03008028 A2 | 1/2003 |
| WO | 2003002177 | 1/2003 |
| WO | 2003002178 A2 | 1/2003 |
| WO | 2003008029 | 1/2003 |
| WO | 2003022333 A1 | 3/2003 |
| WO | 2003064279 A1 | 8/2003 |
| WO | 03092779 A1 | 11/2003 |
| WO | 03093357 A1 | 11/2003 |
| WO | 2004004611 A1 | 1/2004 |
| WO | 2004004796 A1 | 1/2004 |
| WO | 2004030722 A2 | 4/2004 |
| WO | 2004032992 A2 | 4/2004 |
| WO | 2004045696 | 6/2004 |
| WO | 2004050155 A1 | 6/2004 |
| WO | 2004052440 A1 | 6/2004 |
| WO | 2004056290 A1 | 7/2004 |
| WO | 2004056414 A1 | 7/2004 |

(56)  References Cited

FOREIGN PATENT DOCUMENTS

| | | | |
|---|---|---|---|
| WO | 2004056909 | A1 | 7/2004 |
| WO | 2004075944 | A2 | 9/2004 |
| WO | 2004089454 | A1 | 10/2004 |
| WO | 2005004964 | A1 | 1/2005 |
| WO | 2005014055 | A2 | 2/2005 |
| WO | 2005061035 | A1 | 7/2005 |
| WO | 2005092418 | A1 | 10/2005 |
| WO | 2006005349 | A2 | 1/2006 |
| WO | 2006009509 | A1 | 1/2006 |
| WO | 2006009596 | A1 | 1/2006 |
| WO | 2006017439 | A2 | 2/2006 |
| WO | 2006021590 | A1 | 3/2006 |
| WO | 2006027349 | A1 | 3/2006 |
| WO | 2006033234 | A1 | 3/2006 |
| WO | 2006037321 | A1 | 4/2006 |
| WO | 2006097109 | A2 | 9/2006 |
| WO | 2006110695 | A2 | 10/2006 |
| WO | 2006112782 | A1 | 10/2006 |
| WO | 2006130776 | A2 | 12/2006 |
| WO | 2007001526 | A2 | 1/2007 |
| WO | 2007038988 | A1 | 4/2007 |
| WO | 2007050685 | | 5/2007 |
| WO | 2007083033 | A2 | 7/2007 |
| WO | 2008089770 | A1 | 7/2008 |
| WO | 2008104573 | A2 | 9/2008 |
| WO | 2008104603 | A1 | 9/2008 |
| WO | 2008138351 | A1 | 11/2008 |
| WO | 2008138352 | A1 | 11/2008 |
| WO | 2008151074 | A1 | 12/2008 |
| WO | 2009000277 | A1 | 12/2008 |
| WO | 2009012336 | A1 | 1/2009 |
| WO | 2009017541 | A1 | 2/2009 |
| WO | 2009043872 | A1 | 4/2009 |
| WO | 2009068043 | A2 | 6/2009 |
| WO | 2009080265 | A1 | 7/2009 |
| WO | 2009108243 | A1 | 9/2009 |
| WO | 2010006620 | A1 | 1/2010 |
| WO | 2010041084 | A1 | 4/2010 |
| WO | 2010054659 | A1 | 5/2010 |
| WO | 2010054666 | A1 | 5/2010 |
| WO | 2010129362 | A1 | 11/2010 |
| WO | 2010130261 | A1 | 11/2010 |
| WO | 2010149174 | A1 | 12/2010 |
| WO | 2010149175 | A1 | 12/2010 |
| WO | 2010151682 | A2 | 12/2010 |
| WO | 2011011023 | A1 | 1/2011 |
| WO | 2011014201 | A1 | 2/2011 |
| WO | 2011019359 | A1 | 2/2011 |
| WO | 2011026929 | A1 | 3/2011 |
| WO | 2011026930 | A1 | 3/2011 |
| WO | 2011063816 | A1 | 6/2011 |
| WO | 2011073403 | A1 | 6/2011 |
| WO | 2011076211 | A1 | 6/2011 |
| WO | 2011079129 | A1 | 6/2011 |
| WO | 2011109393 | A1 | 9/2011 |
| WO | 2012016570 | A2 | 2/2012 |
| WO | 2012016571 | A2 | 2/2012 |
| WO | 2012079590 | A1 | 6/2012 |
| WO | 2012085124 | A1 | 6/2012 |
| WO | 2012126474 | A1 | 9/2012 |
| WO | 2012134804 | A1 | 10/2012 |
| WO | 2012139214 | A1 | 10/2012 |
| WO | 2013010745 | A1 | 1/2013 |
| WO | 2013029621 | A1 | 3/2013 |
| WO | 2013075725 | A1 | 5/2013 |
| WO | 2014062225 | A1 | 4/2014 |
| WO | 2014081859 | A1 | 5/2014 |
| WO | 2014142917 | A1 | 9/2014 |
| WO | 2014142923 | A1 | 9/2014 |
| WO | 2014165046 | A1 | 10/2014 |
| WO | 15069843 | A2 | 5/2015 |
| WO | 2015075841 | A1 | 5/2015 |
| WO | 15090338 | A1 | 6/2015 |
| WO | 2015089189 | A2 | 6/2015 |
| WO | 2015105942 | A1 | 7/2015 |
| WO | 15142506 | A1 | 9/2015 |
| WO | 2015184365 | A1 | 12/2015 |
| WO | 201603323 | A1 | 1/2016 |
| WO | 2016008493 | A1 | 1/2016 |
| WO | 2016116915 | A1 | 7/2016 |
| WO | 2016206701 | A1 | 12/2016 |
| WO | 2017185052 | A1 | 10/2017 |
| WO | 2018029279 | A1 | 2/2018 |
| WO | 2018059637 | A1 | 4/2018 |
| WO | 2018134748 | A1 | 7/2018 |
| WO | 2018150975 | A1 | 8/2018 |
| WO | 2018156589 | A2 | 8/2018 |
| WO | 2018219433 | A1 | 12/2018 |
| WO | 2019002066 | A2 | 1/2019 |
| WO | 2019014344 | A1 | 1/2019 |
| WO | 2019070984 | A1 | 4/2019 |
| WO | 2019083104 | A1 | 5/2019 |
| WO | 2019083839 | A1 | 5/2019 |
| WO | 2019099845 | A1 | 5/2019 |
| WO | 2019099975 | A2 | 5/2019 |
| WO | 2019113203 | A1 | 6/2019 |
| WO | 2019123004 | A1 | 6/2019 |
| WO | WO-2019123005 | A1 * | 6/2019 | ............ A61M 25/00 |
| WO | 2019245679 | A1 | 12/2019 |
| WO | 2020006527 | A1 | 1/2020 |
| WO | 2020015804 | A1 | 1/2020 |
| WO | 2020106822 | A1 | 5/2020 |
| WO | 2020125908 | A1 | 6/2020 |
| WO | 2020223146 | A1 | 11/2020 |
| WO | 2020237286 | A1 | 12/2020 |
| WO | 2020251961 | A1 | 12/2020 |
| WO | 2020252003 | A1 | 12/2020 |
| WO | 2020263859 | A1 | 12/2020 |
| WO | 2021034487 | A1 | 2/2021 |
| WO | 2021041703 | A1 | 3/2021 |
| WO | 2021051158 | A1 | 3/2021 |
| WO | 2021077103 | A1 | 4/2021 |
| WO | 2021087099 | A1 | 5/2021 |
| WO | 2021092271 | A1 | 5/2021 |
| WO | 2021097519 | A1 | 5/2021 |
| WO | 2021108115 | A1 | 6/2021 |
| WO | 2021115840 | A1 | 6/2021 |
| WO | 2021127040 | A1 | 6/2021 |
| WO | 2021183718 | A1 | 9/2021 |
| WO | 2022031520 | A1 | 2/2022 |
| WO | 2022031550 | A1 | 2/2022 |
| WO | 2022056263 | A2 | 3/2022 |
| WO | 2022223978 | A1 | 10/2022 |
| WO | 2022223980 | A1 | 10/2022 |
| WO | 2022223983 | A1 | 10/2022 |
| WO | 2022223985 | A1 | 10/2022 |
| WO | 2022223987 | A1 | 10/2022 |
| WO | 2022260831 | A1 | 12/2022 |
| WO | 2023003682 | A1 | 1/2023 |
| WO | 2023055832 | A1 | 4/2023 |
| WO | 2023180707 | A1 | 9/2023 |
| WO | 2023211421 | A1 | 11/2023 |
| WO | 2024112323 | A1 | 5/2024 |
| WO | 2024112324 | A1 | 5/2024 |
| WO | 2024112325 | A1 | 5/2024 |
| WO | 2024112799 | A1 | 5/2024 |
| WO | 2024112805 | A1 | 5/2024 |
| WO | 2025193963 | A1 | 9/2025 |
| WO | 2025221562 | A1 | 10/2025 |

OTHER PUBLICATIONS

U.S. Appl. No. 13/662,278, filed Oct. 26, 2012 Final Office Action dated Feb. 20, 2015.
U.S. Appl. No. 13/662,278, filed Oct. 26, 2012 Final Office Action dated Oct. 19, 2016.
U.S. Appl. No. 13/662,278, filed Oct. 26, 2012 Non-Final Office Action dated Jul. 7, 2016.
U.S. Appl. No. 13/662,278, filed Oct. 26, 2012 Non-Final Office Action dated Sep. 12, 2014.
U.S. Appl. No. 13/662,278, filed Oct. 26, 2012 Non-Final Office Action dated Sep. 17, 2015.

(56)  References Cited

OTHER PUBLICATIONS

U.S. Appl. No. 13/802,095, filed Mar. 13, 2013 Non-Final Office Action dated Aug. 15, 2014.

U.S. Appl. No. 13/802,095, filed Mar. 13, 2013 Notice of Allowance dated Nov. 28, 2014.

U.S. Appl. No. 14/681,023, filed Apr. 7, 2015 Non-Final Office Action dated Nov. 9, 2016.

U.S. Appl. No. 14/681,023, filed Apr. 7, 2015 Notice of Allowance dated Mar. 8, 2017.

U.S. Appl. No. 14/707,954, filed May 8, 2015 Non-Final Office Action dated Dec. 1, 2016.

U.S. Appl. No. 15/506,723, filed Feb. 24, 2017 Final Office Action dated Dec. 9, 2019.

U.S. Appl. No. 15/506,723, filed Feb. 24, 2017 Non-Final Office Action dated Aug. 27, 2019.

U.S. Appl. No. 15/506,723, filed Feb. 24, 2017 Notice of Allowance dated Jul. 29, 2020.

U.S. Appl. No. 15/639,844, filed Jun. 30, 2017 Non-Final Office Action dated Jul. 10, 2019.

U.S. Appl. No. 15/639,844, filed Jun. 30, 2017 Notice of Allowance dated Aug. 13, 2019.

U.S. Appl. No. 15/669,697, filed Aug. 4, 2017 Non-Final Office Action dated Oct. 18, 2018.

U.S. Appl. No. 15/669,697, filed Aug. 4, 2017 Notice of Allowance dated Mar. 1, 2019.

U.S. Appl. No. 15/724,879, filed Oct. 4, 2017 Advisory Action dated Jan. 29, 2019.

U.S. Appl. No. 15/724,879, filed Oct. 4, 2017 Examiner's Answer dated Jul. 25, 2019.

U.S. Appl. No. 15/724,879, filed Oct. 4, 2017 Final Office Action dated Dec. 4, 2018.

U.S. Appl. No. 15/724,879, filed Oct. 4, 2017 Non-Final Office Action dated Jul. 19, 2018.

U.S. Appl. No. 15/724,879, filed Oct. 4, 2017 Notice of Allowance dated Aug. 14, 2020.

U.S. Appl. No. 15/724,879, filed Oct. 4, 2017 PTAB Decision on Appeal dated Jul. 1, 2020.

U.S. Appl. No. 15/724,879, filed Oct. 4, 2017 Restriction Requirement dated Mar. 7, 2018.

U.S. Appl. No. 16/453,809, filed Jun. 26, 2019 Notice of Allowance dated Apr. 14, 2020.

U.S. Appl. No. 17/114,275, filed Dec. 7, 2020 Final Office Action dated May 23, 2023.

U.S. Appl. No. 17/114,275, filed Dec. 7, 2020 Non-Final Office Action dated Jan. 31, 2023.

U.S. Appl. No. 17/114,275, filed Dec. 7, 2020 Notice of Allowance dated Aug. 9, 2023.

Wong, "Hydrogels, water-absorbing polymers" Catalyst, vol. 18, Issue 1, pp. 18-21, Sep. 2007.

PCT/US2022/026177 filed Apr. 25, 2022 International Search Report & Written Opinion dated Mar. 20, 2023.

U.S. Appl. No. 17/796,611, filed Jul. 29, 2022 Non-Final Office Action dated Mar. 20, 2025.

"Medifilm." Datasheet [online]. Mylan Technologies Inc., 2003 [retrieved on Febuary 14, 2020]. Retrieved from the Internet: <URL: https://web.archive.org/web/20030205090818/http://www.mylantech.com/products/medifilm.html>.

"Tripartite Biocompatibility Guidance for Medical Devices," DSMA (Apr. 24, 1987).

Akzo Nobel, "Ethomeen C/25 technical data sheet" Mar. 10, 2009.

Amirkhai IL et al., "Nitric Oxide Complexes of Trimethylaluminium" Journal of Organometallic Chemistry, 149 (1978).

Angus "Chemie GmbHTechnical Data Sheet", AMP-95, TDS 10A (2000).

AU 2014248744 filed Jul. 9, 2015 Examiner's Report dated Jul. 26, 2017.

AU 2015306630 filed Feb. 2, 2017 Office Action dated Aug. 2, 2018.

BR PI 0506836-3 filed Jan. 18, 2005, Technical Report dated Jul. 28, 2015.

BR1120170040301 filed Feb. 21, 2017 Office Action dated Aug. 20, 2019.

CA 2,769,026 filed Jan. 24, 2012 First Examination Report dated Nov. 4, 2013.

CN 201080058895.4 filed Jun. 21, 2012 First Office Action dated Feb. 27, 2014.

CN 201080058895.4 filed Jun. 21, 2012 Second Office Action dated Nov. 3, 2014.

CN 201080058895.4 filed Jun. 21, 2012 Third Office Action dated May 4, 2015.

CN 201480013064.3 filed Sep. 8, 2015 Office Action dated Jun. 29, 2017.

CN 201480013064.3 filed Sep. 8, 2015 Office Action dated Oct. 10, 2016.

CN 20158004662.3 filed Feb. 24, 2017 Office Action dated Jul. 8, 2019.

CN 20158004662.3 filed Feb. 24, 2017 Office Action dated Sep. 20, 2019.

EP 09848341.5 filed Feb. 27, 2012 extended European Search Report dated Apr. 4, 2013.

EP 09848341.5 filed Feb. 27, 2012 supplemental European Search Report dated Nov. 8, 2013.

EP 10840071.4 filed Jul. 4, 2012 Exam Report dated Apr. 29, 2014.

EP 10840071.4 filed Jul. 4, 2012 extended European Search Report dated Apr. 17, 2013.

EP 10840071.4 filed Jul. 4, 2012 Notice of Opposition dated Apr. 24, 2017.

EP 10840071.4 filed Jul. 4, 2012 Office Action dated Jul. 9, 2015.

EP 11751198.0 filed Sep. 28, 2012 Exam Report dated Feb. 7, 2014.

EP 11751198.0 filed Sep. 28, 2012 extended European search report dated Jul. 9, 2013.

EP 14779919.1 filed Sep. 10, 2015 Extended European Search Report dated Aug. 23, 2016.

EP 14779919.1 filed Sep. 10, 2015 Office Action dated Jul. 4, 2017.

EP 15836062.8 filed Feb. 17, 2017 Extended European Search Report dated Feb. 20, 2018.

EP 15836062.8 filed Feb. 17, 2017 Office Action dated Feb. 19, 2019.

EP 16171279.9 filed May 25, 2016 Extended European Search Report, dated Aug. 23, 2016.

EP 16171279.9 filed May 25, 2016 Intent to Grant, dated Jun. 13, 2017.

EP 17201044.9 filed Nov. 10, 2017 Extended European Search Report dated Jan. 18, 2018.

EP 17201044.9 filed Nov. 10, 2017 Office Action dated Jul. 4, 2019.

Hollister, "Vapro intermittent catheter brochure" (2009).

Johnson et al. "Activities of a Nitrofurazone-Containing Urinary Catheter and a Silver Hydrogel Catheter against Multidrug-Resistant Bacteria Characteristic of Catheter-Associated Urinary Tract Infection" Antimicrobial Agents and Chemotherapy, Dec. 1999.

JP 2012-546157 filed Jun. 12, 2012 Decision of Rejection dated Aug. 21, 2015.

JP 2012-546157 filed Jun. 12, 2012 First Office Action dated Sep. 16, 2014.

JP 2015-243156 filed Dec. 14, 2015 Office Action dated Sep. 16, 2016.

JP 2016-501444 filed Sep. 11, 2015 Office Action dated Dec. 14, 2017.

JP 2017-511223 filed Feb. 24, 2017 Office Action dated Jun. 4, 2019.

Lubrizol, "Neutralizing Carbopol®* and Pemulen™* Polymers in Aqueous and Hydroalcoholic Systems" Technical Data Sheet TDS-237 Edition: Sep. 16, 2009.

Moore et al., "The Swelling of Cotton in Water: A Microscopical Study," Textile Research Journal, vol. 20, Issue 9 pp. 620-630, Sep. 1, 1950.

MX/a/2015/009904 filed Jul. 30, 2015 Office Action dated Jun. 29, 2018.

MX/a/2017/002457 filed Feb. 23, 2017 Office Action dated Sep. 4, 2019.

(56)          References Cited

OTHER PUBLICATIONS

Newman "Intermittent Catheterization and Current Best Practices: Catheter Design and Types"; http://www.medscape.com/viewarticle/745908_8, last accessed May 31, 2013.

Newman et al. "Review of Intermittent Catheterization and Current Best Practices," Urological Nursing, vol. 31, No. 1 pp. 12-29, 48, Jan. 2011.

Norton, J.A et al., Surgery: Basic Science and Clinical Evidence Springer, 2nd ed., 2008, p. 281.

PCT/US2006/041633 filed Oct. 25, 2006 International Preliminary Report on Patentability dated Mar. 24, 2009.

PCT/US2006/041633 filed Oct. 25, 2006 Search Report dated Aug. 12, 2008.

PCT/US2006/041633 filed Oct. 25, 2006 Written Opinion dated Aug. 12, 2008.

PCT/US2021/043771 filed Jul. 29, 2021 International Search Report and Written Opinion dated Jan. 24, 2022.

PCT/US2021/044021 filed Jul. 30, 2021 International Search Report and Written Opinion dated Jan. 24, 2022.

PCT/US2021/049867 filed Sep. 10, 2021 International Search Report and Written Opinion dated Mar. 11, 2022.

PCT/US2009/055389 filed Aug. 28, 2009 International Search Report dated Oct. 20, 2009.

PCT/US2009/055389 filed Aug. 28, 2009 Written Opinion dated Oct. 20, 2009.

PCT/US2009/055395 filed Aug. 28, 2009 International Preliminary Report on Patentability dated Jan. 31, 2012.

PCT/US2009/055395 filed Aug. 28, 2009 International Search Report dated Oct. 15, 2009.

PCT/US2009/055395 filed Aug. 28, 2009 Written Opinion dated Oct. 15, 2009.

PCT/US2010/061597 filed Dec. 21, 2010 International Preliminary Report on Patentability dated Jun. 26, 2012 and Written Opinion dated Feb. 28, 2011.

PCT/US2010/061597 filed Dec. 21, 2010 International Search Report dated Feb. 28, 2011.

PCT/US2011/026681 filed Mar. 1, 2011 International Preliminary Report on Patentability dated Sep. 4, 2012.

PCT/US2011/026681 filed Mar. 1, 2011 International Search Report dated Apr. 27, 2011.

PCT/US2011/026681 filed Mar. 1, 2011 Written Opinion dated Apr. 27, 2011.

PCT/US2014/024231 filed Mar. 12, 2014 International Search Report and Written Opinion dated Jul. 10, 2014.

PCT/US2022/029431 filed May 16, 2022 International Search Report and Written Opinion dated Sep. 15, 2022.

PCT/US2022/035565 filed Jun. 29, 2022 International Search Report and Written Opinion dated Sep. 27, 2022.

PCTUS2018054378 filed Oct. 4, 2018 International Preliminary Report on Patentability dated Jan. 2, 2019.

PCTUS2018054378 filed Oct. 4, 2018 International Search Report and Written opinion dated Jan. 2, 2019.

Peppas, "Hydrogels," Biomaterial Science: An Introduction to Materials in Medicine. 2nd Edition, pp. 100-107, Aug. 18, 2004.

Piyush Gupta et al. Hydrogels: from controlled release to pH-responsive drug delivery, May 2002, DDT vol. 7, No. 10, pp. 569-579. (Year: 2002).

RU 2015140616 filed Sep. 24, 2015 Office Action dated Feb. 21, 2018.

U.S. Appl. No. 12/091,916, filed Feb. 2, 2009 Final Office Action dated Sep. 22, 2011.

U.S. Appl. No. 12/091,916, filed Feb. 2, 2009 Non-Final Office Action dated May 10, 2011.

U.S. Appl. No. 12/091,916, filed Feb. 2, 2009 Non-Final Office Action dated Nov. 24, 2010.

U.S. Appl. No. 12/091,916, filed Feb. 2, 2009 Notice of Allowance dated Aug. 17, 2012.

U.S. Appl. No. 13/387,447, filed Mar. 22, 2012 Advisory Action dated Feb. 27, 2014.

U.S. Appl. No. 13/387,447, filed Mar. 22, 2012 Examiner's Answer dated Oct. 5, 2016.

U.S. Appl. No. 13/387,447, filed Mar. 22, 2012 Final Office Action dated Dec. 11, 2013.

U.S. Appl. No. 13/387,447, filed Mar. 22, 2012 Final Office Action dated Oct. 31, 2014.

U.S. Appl. No. 13/387,447, filed Mar. 22, 2012 Final Office Action dated Oct. 5, 2015.

U.S. Appl. No. 13/387,447, filed Mar. 22, 2012 Non-Final Office Action dated Jan. 15, 2013.

U.S. Appl. No. 13/387,447, filed Mar. 22, 2012 Non-Final Office Action dated Jul. 15, 2014.

U.S. Appl. No. 13/387,447, filed Mar. 22, 2012 Non-Final Office Action dated Jun. 6, 2013.

U.S. Appl. No. 13/387,447, filed Mar. 22, 2012 Non-Final Office Action dated Mar. 12, 2015.

U.S. Appl. No. 13/387,447, filed Mar. 22, 2012 Notice of Allowance dated Jul. 30, 2018.

U.S. Appl. No. 13/387,447, filed Mar. 22, 2012 Patent Board Decision dated Jun. 1, 2018.

U.S. Appl. No. 13/389,753, filed Mar. 20, 2012 Decision on Appeal dated Jun. 29, 2017.

U.S. Appl. No. 13/389,753, filed Mar. 20, 2012 Examiner's Answer dated Aug. 27, 2015.

U.S. Appl. No. 13/389,753, filed Mar. 20, 2012 Final Office Action dated Dec. 10, 2014.

U.S. Appl. No. 13/389,753, filed Mar. 20, 2012 Non-Final Office Action dated Jul. 21, 2014.

U.S. Appl. No. 13/389,753, filed Mar. 20, 2012 Notice of Allowance dated Jul. 5, 2017.

U.S. Appl. No. 13/516,660, filed Aug. 27, 2012 Advisory Action dated Nov. 19, 2019.

U.S. Appl. No. 13/516,660, filed Aug. 27, 2012 Advisory Action dated Sep. 22, 2016.

U.S. Appl. No. 13/516,660, filed Aug. 27, 2012 Board Decision dated Jan. 22, 2019.

U.S. Appl. No. 13/516,660, filed Aug. 27, 2012 Examiner's Answer dated Nov. 22, 2017.

U.S. Appl. No. 13/516,660, filed Aug. 27, 2012 Final Office Action dated Jun. 29, 2016.

U.S. Appl. No. 13/516,660, filed Aug. 27, 2012 Final Office Action dated Sep. 9, 2019.

U.S. Appl. No. 13/516,660, filed Aug. 27, 2012 Non-Final Office Action dated Jan. 8, 2020.

U.S. Appl. No. 13/516,660, filed Aug. 27, 2012 Non-Final Office Action dated Mar. 15, 2019.

U.S. Appl. No. 13/516,660, filed Aug. 27, 2012 Non-Final Office Action dated Mar. 8, 2016.

U.S. Appl. No. 13/516,660, filed Aug. 27, 2012 Notice of Allowance dated Oct. 27, 2020.

U.S. Appl. No. 13/582,698, filed Sep. 4, 2012 Non-Final Office Action dated Sep. 24, 2014.

U.S. Appl. No. 13/662,278, filed Oct. 26, 2012 Board Decision dated Aug. 23, 2018.

EP 24164460.8 filed Mar. 19, 2024 Extended European Search Report dated Jun. 19, 2024.

PCT/US2022/045084 filed Sep. 28, 2022 International Search Report and Written Opinion dated Jan. 3, 2023.

PCT/US2023/080761 filed Nov. 21, 2023 International Search Report and Written Opinion dated Apr. 9, 2024.

PCT/US2023/080769 filed Nov. 21, 2023 International Search Report and Written Opinion dated Mar. 15, 2024.

PCT/US2025/019799 filed Mar. 13, 2025 International Search Report and Written Opinion dated Jun. 4, 2025.

U.S. Appl. No. 18/019,464, filed Feb. 2, 2023 Restriction Requirement dated May 6, 2025.

U.S. Appl. No. 18/025,875, filed Mar. 10, 2023 Restriction Requirement dated Jun. 4, 2025.

PCT/US2022/050645 filed Nov. 21, 2022 International Search Report and Written Opinion dated Jun. 28, 2023.

PCT/US2022/050646 filed Nov. 21, 2022 International Search Report and Written Opinion dated May 30, 2023.

(56) References Cited

OTHER PUBLICATIONS

PCT/US2022/050648 filed Nov. 21, 2022 International Search Report and Written Opinion dated Jun. 16, 2023.

PCT/US2025/023972 filed Apr. 9, 2025 International Search Report and Written Opinion dated Sep. 18, 2025.

U.S. Appl. No. 17/796,611, filed Jul. 29, 2022 Final Office Action dated Sep. 24, 2025.

U.S. Appl. No. 18/019,464, filed Feb. 2, 2023 Non-Final Office Action dated Jul. 30, 2025.

U.S. Appl. No. 18/025,875, filed Mar. 10, 2023 Non-Final Office Action dated Aug. 28, 2025.

U.S. Appl. No. 18/604,394, filed Mar. 13, 2024 Non-Final Office Action dated Jul. 15, 2025.

U.S. Appl. No. 18/641,181, filed Apr. 19, 2024 Restriction Requirement dated Oct. 21, 2025.

U.S. Appl. No. 17/796,611, filed Jul. 29, 2022 Advisory Action dated Nov. 28, 2025.

U.S. Appl. No. 17/796,611, filed Jul. 29, 2022 Non-Final Office Action dated Jan. 8, 2026.

U.S. Appl. No. 18/019,464, filed Feb. 2, 2023 Notice of Allowance dated Nov. 25, 2025.

U.S. Appl. No. 18/025,875, filed Mar. 10, 2023 Notice of Allowance dated Jan. 14, 2026.

U.S. Appl. No. 18/536,063, filed Dec. 11, 2023 Non-Final Office Action dated Nov. 12, 2025.

U.S. Appl. No. 18/580,449, filed Jan. 19, 2024 Non-Final Office Action dated Feb. 2, 2026.

U.S. Appl. No. 18/604,394, filed Mar. 13, 2024 Final Office Action dated Jan. 23, 2026.

U.S. Appl. No. 18/641,181, filed Apr. 19, 2024 Non-Final Office Action dated Jan. 12, 2026.

U.S. Appl. No. 18/536,063, filed Dec. 11, 2023 Notice of Allowance dated Mar. 31, 2026.

U.S. Appl. No. 18/568,208, filed Dec. 7, 2023 Non-Final Office Action dated Apr. 1, 2026.

U.S. Appl. No. 18/604,394, filed Mar. 13, 2024 Notice of Allowance dated Apr. 20, 2026.

U.S. Appl. No. 18/641,181, filed Apr. 19, 2024 Final Office Action dated Apr. 28, 2026.

* cited by examiner

INTERMITTENT-CATHETER ASSEMBLIES AND METHODS THEREOF

PRIORITY

This application is a U.S. national stage of International Application No. PCT/US2021/044021, filed Jul. 30, 2021, which claims the benefit of priority to U.S. Provisional Application No. 63/060,627, filed Aug. 3, 2020, each of which is incorporated by reference in its entirety into this application.

BACKGROUND

Users of urinary catheters such as intermittent catheters self-catheterize four to six times a day. However, catheterization with such intermittent catheters can be messy. Indeed, existing intermittent catheters often include water or lubricant in packages thereof for lubrication the intermittent catheters prior to insertion. A user often dumps most of the water or lubricant out of a package before catheterization to mitigate any mess via spillage of the water of lubricant. What is needed is a simple-to-use intermittent catheter that facilitates cleanliness before and after use.

Disclosed herein are intermittent-catheter assemblies and methods thereof that address the foregoing.

SUMMARY

Disclosed herein is an intermittent-catheter assembly including, in some embodiments, an intermittent catheter and a catheter housing. The intermittent catheter includes a proximal piece including a neck, a cap configured to cap a proximal opening of the proximal piece, and a catheter tube fluidly connected to the proximal piece. The catheter housing is around at least the catheter tube. The catheter housing includes a distal piece and a collapsible sheath. The distal piece includes a chamber or receptacle including a lubricant or lubricating sponge for lubricating the catheter tube when the distal piece is proximally slid over the catheter tube. The collapsible sheath includes a distal portion coupled to the distal piece and a proximal portion coupled to the neck of the proximal piece of the intermittent catheter. An entirety of the catheter tube is disposed in the catheter housing in a packaged state of the intermittent-catheter assembly.

In some embodiments, the cap is configured to cap the proximal piece when not actively placing the intermittent catheter for voiding urine, voiding urine, or removing the intermittent catheter after voiding urine.

In some embodiments, the cap is configured to sit over a flange in a proximal portion of the proximal piece. The flange includes a gasket over the flange configured to sit between the cap and the proximal piece and form a fluidly tight seal when the cap caps the proximal piece.

In some embodiments, the cap is coupled to the proximal piece by a living hinge.

In some embodiments, a proximal portion of the cap includes a receptacle configured to ouroborosly accept a ribbed portion of the distal piece of the catheter housing inserted therein.

In some embodiments, the distal piece inserted into the receptacle of the cap forms an after-use storage state of the intermittent-catheter assembly configured to prevent urine leakage from the intermittent-catheter assembly after voiding urine therewith.

In some embodiments, the catheter tube includes a plurality of eyelets proximate a catheter tip. The eyelets are fluid communication with the proximal opening of the proximal piece.

In some embodiments, the intermittent-catheter assembly further includes a removable foil seal over a distal opening of the distal piece in the packaged state of the intermittent-catheter assembly. The foil seal is configured to maintain sterility of the intermittent catheter prior to use thereof.

In some embodiments, the foil seal is further configured to retain the lubricant in the intermittent-catheter assembly while the intermittent-catheter assembly is in the packaged state thereof.

In some embodiments, the catheter housing further includes an internal piece slidably disposed around the catheter tube. The internal piece is coupled to the sheath between a proximal portion of the sheath and a distal portion of the sheath providing support to the sheath.

In some embodiments, the proximal portion of the sheath is pleated or bellowed and the distal portion of the sheath is not pleated or bellowed.

In some embodiments, the distal piece and the internal piece are configured for placing the intermittent catheter. The distal piece and the internal piece form a two-piece handle for placing the intermittent catheter when at least the distal piece is proximally slid over the catheter tube to the internal piece, which sliding also exposes a distal portion of the catheter tube for placing the intermittent catheter.

Also disclosed herein is a package of intermittent-catheter assemblies including, in some embodiments, resealable packaging and a set of intermittent-catheter assemblies disposed therein. The packaging includes a kerfed portion, a removable piece, and a main body. The kerfed portion includes kerfs configured for tearing the removable piece off the package. The main body includes a cavity and a ziplock in an end portion of the main body for resealing the package after removing the removable piece. The set of intermittent-catheter assemblies are disposed in the cavity of the packaging. Each intermittent-catheter assembly of the one-or-more intermittent-catheter assemblies is in a packaged state thereof.

Also disclosed herein is a carrying case for one or more intermittent-catheter assemblies including, in some embodiments, a main body, a top, and a cavity formed between the main body and the top. The top of the carrying case is coupled to the main body of the carrying case by a living hinge. The cavity, which is formed between the main body and the top, is configured to contain the one-or-more intermittent-catheter assemblies in one or more states thereof.

Also disclosed herein is a method of an intermittent-catheter assembly including, in some embodiments, a catheter obtaining step, an uncapping step, a catheter tub e-exposing step, a catheter tube-inserting step, and a urine-voiding step. The catheter obtaining step includes obtaining the intermittent-catheter assembly in a packaged state thereof. The intermittent-catheter assembly includes a catheter housing including a sheath around at least a catheter tube of an intermittent catheter. The uncapping step includes uncapping a cap capping a proximal opening of a proximal piece of the intermittent catheter. The cap is coupled to the proximal piece by a living hinge. The catheter tube-exposing step includes exposing an insertable portion of the catheter tube, which is effectuated by proximally sliding a distal piece of the catheter housing over the catheter tube, which, in turn, lubricates the catheter tube with a lubricant or lubricating sponge in a chamber or receptacle of the distal piece. The catheter tube-inserting step includes inserting the catheter tube into a urethra. The urine-voiding step includes voiding urine from a bladder upon proper placement of the intermittent catheter therein.

In some embodiments, the intermittent-catheter assembly in the packaged state thereof is further packaged in a package of intermittent-catheter assemblies providing about a day's supply thereof.

In some embodiments, the method further includes a foil-removing step. The foil-removing step includes removing a foil seal from a distal opening of the distal piece before the catheter tube-exposing step.

In some embodiments, proximally sliding the distal piece over the catheter tube in accordance with the catheter tube-exposing step includes sliding the distal piece to an internal piece of the catheter housing to form a two-piece handle for inserting the catheter tube into the urethra. A distal portion of the sheath collapses between the distal piece and the internal piece when the distal piece is slid to the internal piece.

In some embodiments, the catheter tube-exposing step further includes proximally sliding the internal piece of the catheter housing or the two-piece handle over the catheter tube to the proximal piece of the intermittent catheter. A proximal portion of the sheath collapses between the internal piece and the proximal piece when the internal piece or the two-piece handle is slide to the proximal piece.

In some embodiments, the method further includes a catheter tube-removing step, a capping step, and a catheter tube-covering step. The catheter tube-removing step includes removing the catheter tube from the urethra after the urine-voiding step. The capping step includes capping the proximal opening of the proximal piece with the cap. The catheter tube-covering step includes covering the insertable portion of the catheter tube by distally sliding the distal piece over the catheter tube.

In some embodiments, the method further includes a joining step. The joining step includes inserting a ribbed portion of the distal piece into a receptacle in a proximal portion of the cap by bending proximal and distal ends of the intermittent-catheter assembly toward each other. The joining step forms an after-use storage state of the intermittent-catheter assembly configured to prevent urine leakage from the intermittent-catheter assembly after the urine-voiding step.

In some embodiments, the method further includes a catheter assembly-storing step. The catheter assembly-storing step includes placing the intermittent-catheter assembly in the after-use storage state thereof into a multiple-use hard-shell carrying case for future disposal of the intermittent-catheter assembly.

Also disclosed herein is another intermittent-catheter assembly including, in some embodiments, an intermittent catheter and a catheter housing coupled to the intermittent catheter. The intermittent catheter includes a proximal piece and a catheter tube fluidly connected to the proximal piece. The proximal piece includes a neck. The catheter housing includes a distal piece and a collapsible sheath. The distal piece is configured to proximally slide over the catheter tube. The collapsible sheath includes a distal portion coupled to the distal piece and a proximal portion coupled to the neck of the proximal piece of the intermittent catheter. An entirety of the catheter tube is disposed in the catheter housing in a packaged state of the intermittent-catheter assembly.

In some embodiments, a distal portion of the distal piece includes a flared receptacle and a proximal portion of the proximal piece includes a flange. The receptacle is configured to ouroborosly accept insertion of the flange therein.

In some embodiments, each piece of the distal piece and the proximal piece includes a medial portion having circumferential ridges. The circumferential ridges are configured for gripping the distal and proximal pieces when inserting the flange into the receptacle.

In some embodiments, the circumferential ridges of the distal piece are also configured for gripping the distal piece when sliding the distal piece over the catheter tube toward the proximal piece to unsheath the catheter tube. The circumferential ridges of the distal piece are also configured for gripping the distal piece when sliding the distal piece over the catheter tube away from the proximal piece to resheath the catheter tube.

In some embodiments, the receptacle includes an inner lip and the flange includes an integrated gasket. The inner lip and the gasket are configured to form a fluidly tight seal when the flange is inserted into the receptacle.

In some embodiments, the flange inserted into the receptacle forms the packaged state of the intermittent-catheter assembly. The packaged state of the intermittent-catheter assembly is configured to retain a hydrophilic coating over the catheter tube, retain a moisture content of the hydrophilic coating, and maintain sterility of the intermittent catheter prior to use thereof.

In some embodiments, the flange inserted into the receptacle after use of the intermittent catheter forms an after-use storage state of the intermittent-catheter assembly. The after-use storage state of the intermittent-catheter assembly is configured to prevent urine leakage from the intermittent-catheter assembly of any residual urine present in the intermittent catheter after voiding urine therewith.

In some embodiments, the catheter tube includes a plurality of eyelets proximate a catheter tip, the eyelets in fluid communication with a proximal opening of the proximal piece.

Also disclosed herein is another method of an intermittent-catheter assembly including, in some embodiments, a catheter-obtaining step, a flange-removing step, a catheter tube-exposing step, a catheter tube-inserting step, and a urine-voiding step. The catheter-obtaining step includes obtaining the intermittent-catheter assembly in a packaged state thereof. The intermittent-catheter assembly includes a catheter housing including a sheath around at least a catheter tube of an intermittent catheter. The flange-removing step includes removing a flange in a proximal portion of a proximal piece of the intermittent catheter from a flared receptacle of a distal portion of a distal piece of the catheter housing. The catheter tube-exposing step includes exposing an insertable portion of the catheter tube including proximally sliding the distal piece over the catheter tube toward the proximal piece. The sheath collapses between the distal piece and the proximal piece with the sliding of the distal piece over the catheter tube, thereby unsheathing the catheter tube. The catheter tube-inserting step includes inserting the catheter tube into a urethra. The urine-voiding step includes voiding urine from a bladder upon proper placement of the intermittent catheter therein.

In some embodiments, the flange is ouroborosly inserted in the receptacle in packaged state of the intermittent-catheter assembly.

In some embodiments, proximally sliding the distal piece over the catheter tube toward the proximal piece forms a two-piece handle between the distal and proximal pieces for the catheter tube-inserting step.

In some embodiments, the method further includes a catheter tube-removing step, a catheter tube-resheathing step, a catheter assembly-bending step, and a joining step. The catheter tube-removing step includes removing the catheter tube from the urethra after the voiding of the urine from the bladder. The catheter tube-resheathing step includes covering the insertable portion of the catheter tube with the sheath by distally sliding the distal piece over the catheter tube, thereby resheathing the catheter tube. The catheter assembly-bending step includes bending proximal and distal portions of the intermittent-catheter assembly toward each other. The joining step includes ouroborosly inserting the flange of the proximal piece into the receptacle of the distal piece, thereby forming an after-use storage state of the intermittent-catheter assembly. The after-use storage state of the intermittent-catheter assembly is configured to prevent urine leakage from the intermittent-catheter assembly after the voiding of the urine from the bladder.

In some embodiments, the method further includes a storing step. The storing step includes placing the intermittent-catheter assembly in the after-use storage state thereof into a multiple-use hard-shell carrying case for future disposal of the intermittent-catheter assembly.

In some embodiments, the intermittent-catheter assembly in the packaged or after-use storage state thereof is further packaged in the carrying case with about a day's supply of other intermittent-catheter assemblies.

These and other features of the concepts provided herein will become more apparent to those of skill in the art in view of the accompanying drawings and following description, which describe particular embodiments of such concepts in greater detail.

DRAWINGS

DESCRIPTION

Figure 1:
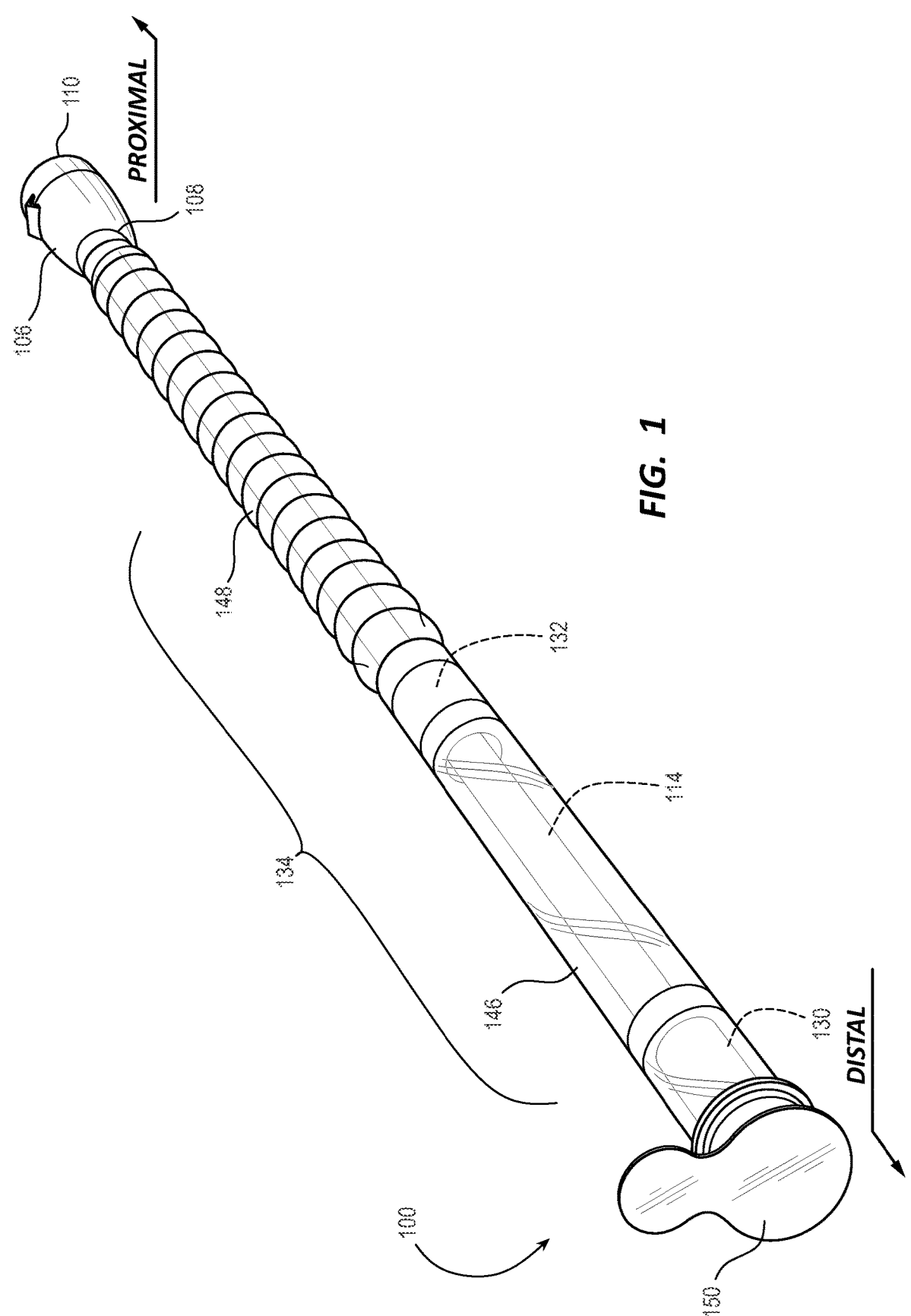
FIG. 1 illustrates a perspective view of an intermittent-catheter assembly in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, catheterization with intermittent catheters can be messy. Indeed, existing intermittent catheters often include water or lubricant in packages thereof for lubrication the intermittent catheters prior to insertion. A user often dumps most of the water or lubricant out of a package before catheterization to mitigate any mess via spillage of the water of lubricant. What is needed is a simple-to-use intermittent catheter that facilitates cleanliness before and after use.

Disclosed herein are intermittent-catheter assemblies and methods thereof that address the foregoing.

Intermittent-Catheter Assemblies

Figures 2, 3, 4, 5:
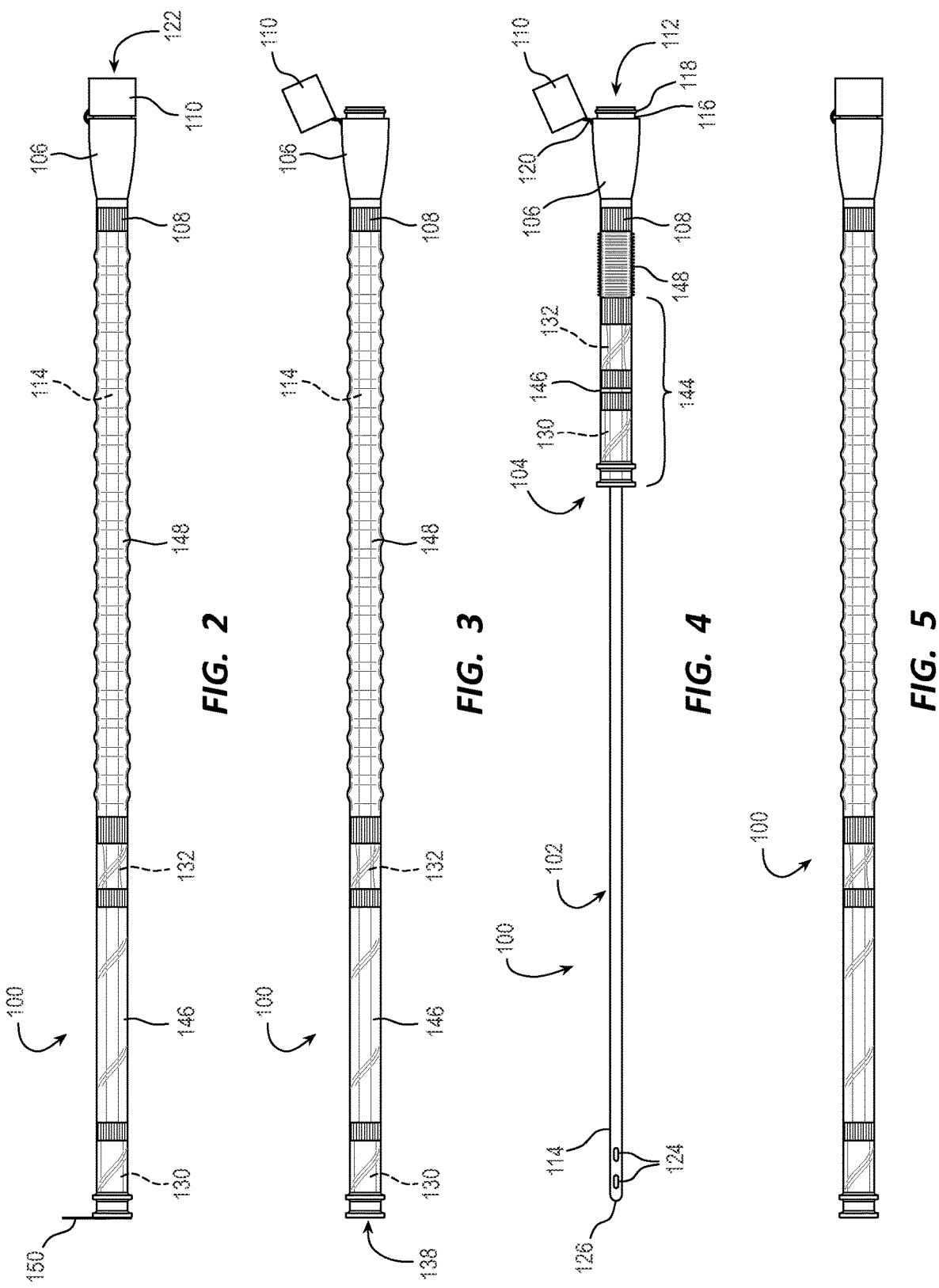
FIG. 2 illustrates a side view of the intermittent-catheter assembly of FIG. 1 in a packaged state thereof in accordance with some embodiments.
FIG. 3 illustrates a side view of the intermittent-catheter assembly of FIG. 1 when uncapped in accordance with some embodiments.
FIG. 4 illustrates a side view of the intermittent-catheter assembly of FIG. 1 with a fully exposed catheter tube in accordance with some embodiments.
FIG. 5 illustrates a side view of the intermittent-catheter assembly of FIG. 1 when capped in accordance with some embodiments.
Figure 6A:
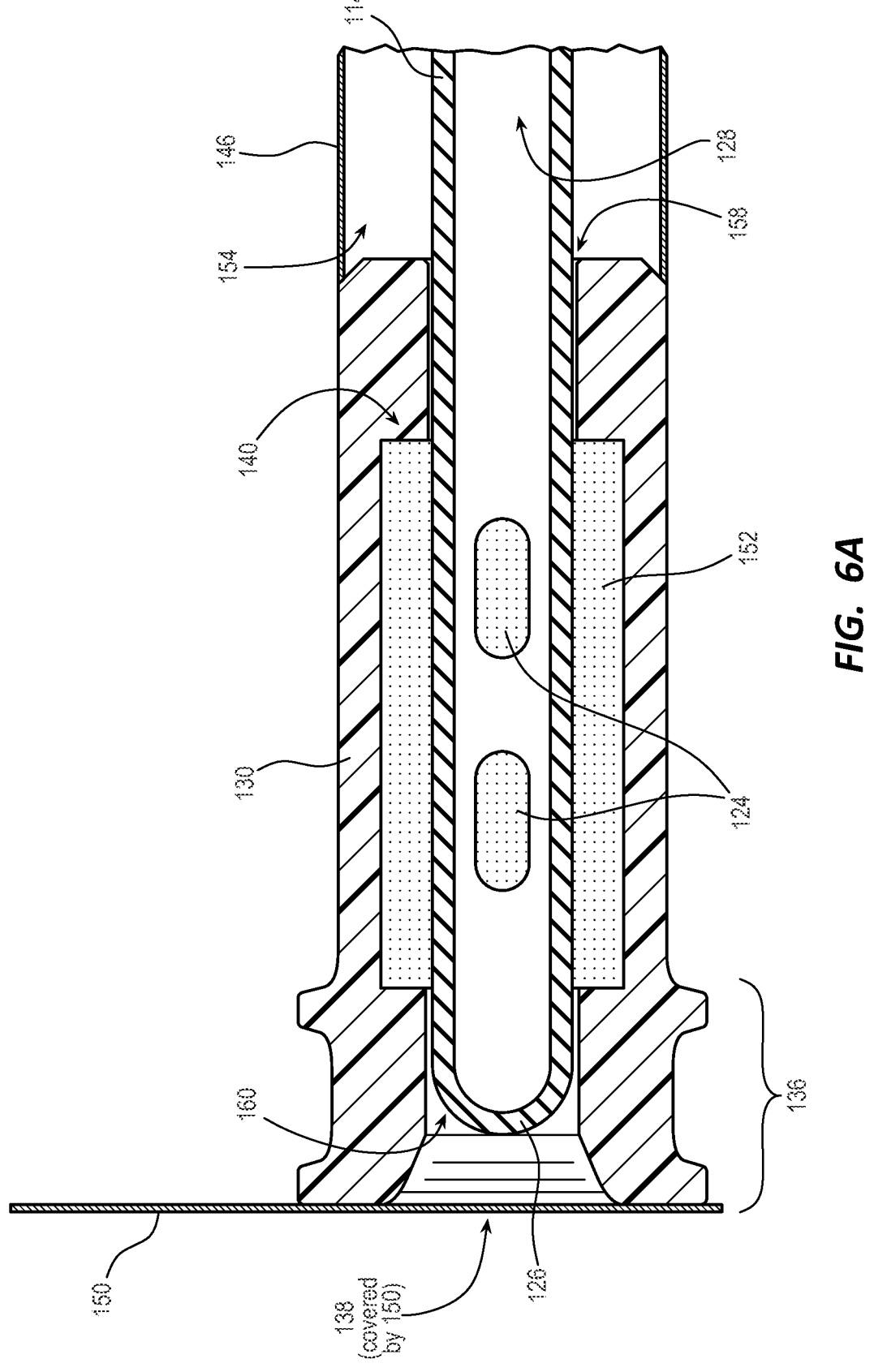
FIG. 6A illustrates a longitudinal cross-section of a distal portion of the intermittent-catheter assembly of FIG. 1 including a lubricant-filled chamber in accordance with some embodiments.
Figure 6B:
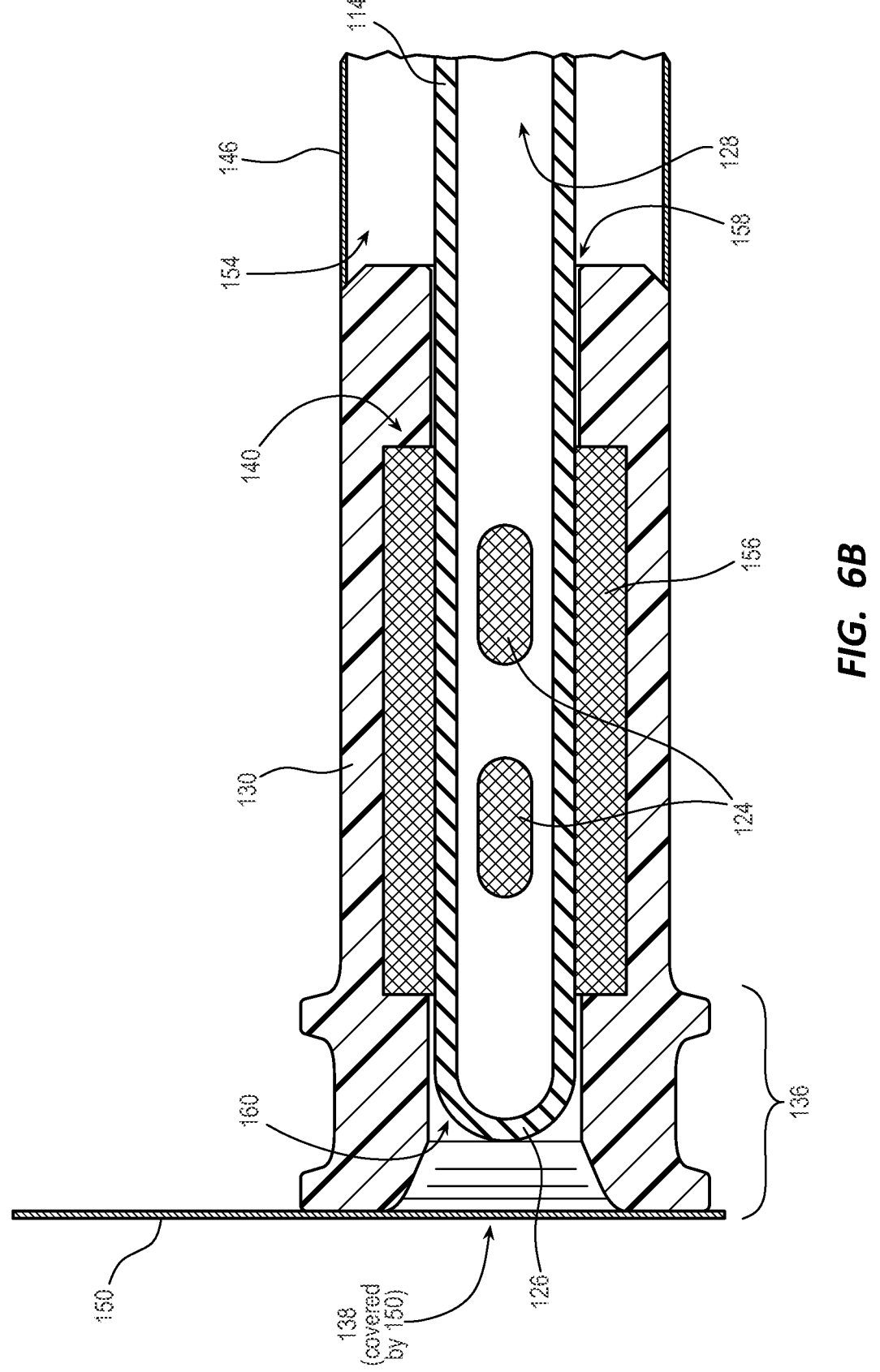
FIG. 6B illustrates the longitudinal cross-section of the distal portion of the intermittent-catheter assembly of FIG. 1 including a lubricating sponge-filled chamber in accordance with some embodiments.
Figure 6C:
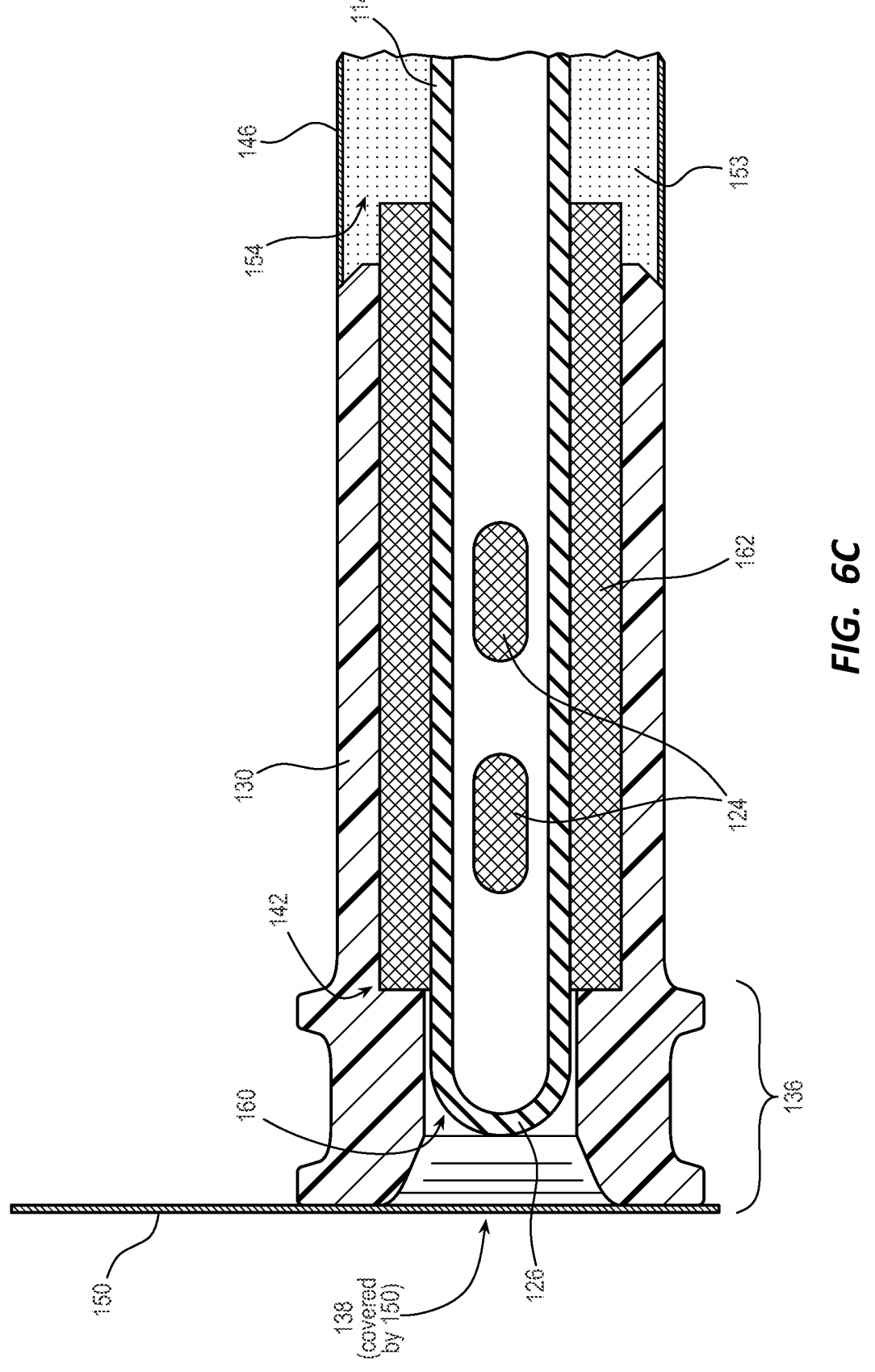
FIG. 6C illustrates the longitudinal cross-section of the distal portion of the intermittent-catheter assembly of FIG. 1 including a lubricating sponge-filled receptacle in accordance with some embodiments.
Figures 7, 8:
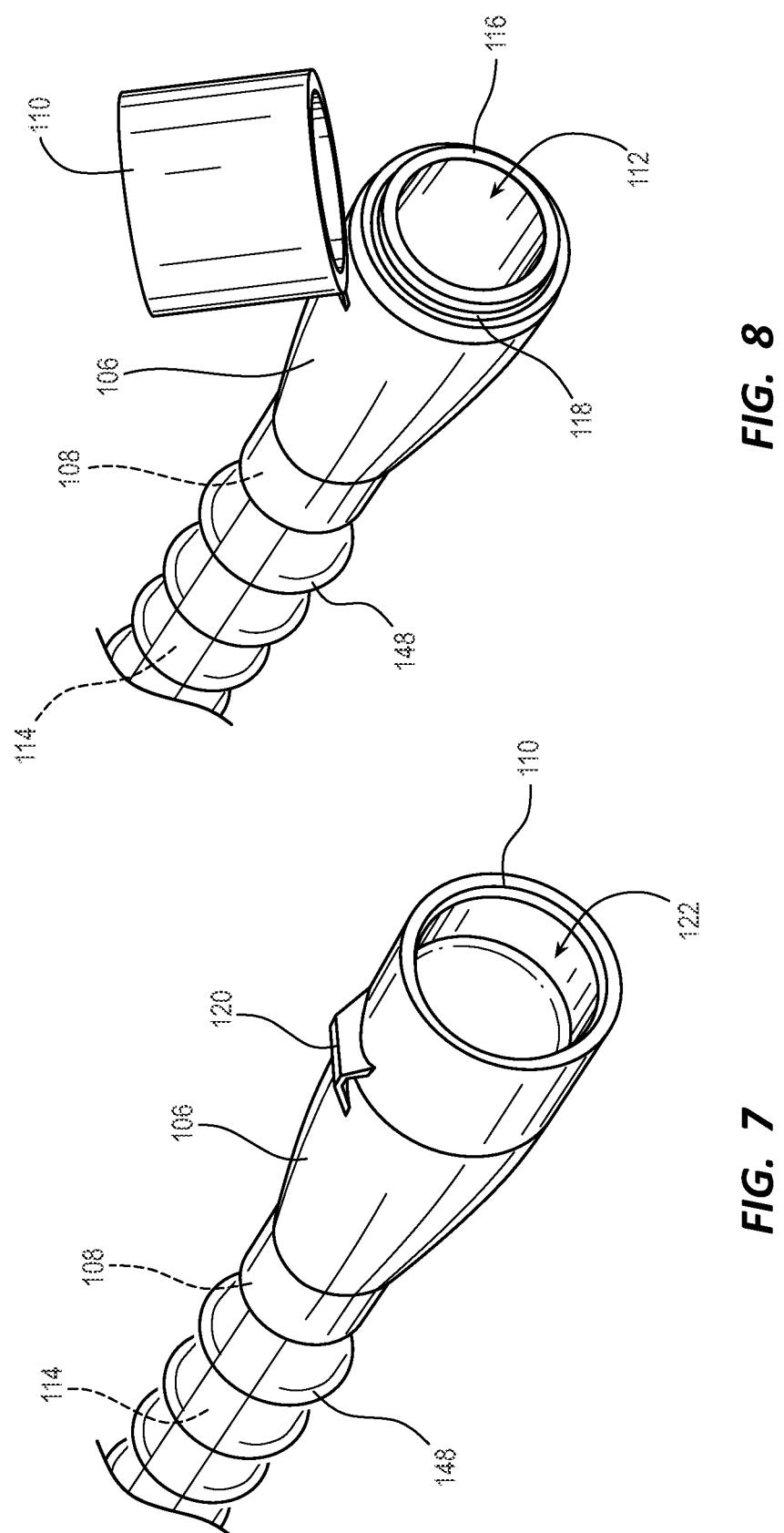
FIG. 7 illustrates a perspective view of a proximal portion of the intermittent-catheter assembly of FIG. 1 when capped in accordance with some embodiments.
FIG. 8 illustrates a perspective view of the proximal portion of the intermittent-catheter assembly of FIG. 1 when uncapped in accordance with some embodiments.

FIGS. 1-5 illustrate various views of an intermittent-catheter assembly 100 in various states accordance with some embodiments. For example: The intermittent-catheter assembly 100 of FIGS. 1 and 2 are in a packaged state thereof as set forth below. The intermittent-catheter assembly 100 of FIG. 3 is in a pre-insertion state thereof such as before the catheter tube-exposing step of the method set forth below. The intermittent-catheter assembly 100 of FIG. 4 is in a pre-insertion state thereof such as after the catheter tube-exposing step of the method set forth below, an insertion state thereof such as during the urine-voiding step of the method set forth below, or in a post-insertion state thereof such as after the catheter tube-removing step of the method set forth below. The intermittent-catheter assembly 100 of FIG. 5 is in a pre joined state thereof such as before the joining step of the method set forth below. Continuing with FIGS. 6A-6C, 7, and 8, a longitudinal cross-section of a distal portion of the intermittent-catheter assembly 100 is illustrated in FIGS. 6A-6C in accordance with some embodiments, whereas FIGS. 7 and 8 illustrate a perspective view of a proximal portion of the intermittent-catheter assembly 100 in accordance with some embodiments.

As shown, the intermittent-catheter assembly 100 includes, in some embodiments, an intermittent catheter 102 (e.g., a male intermittent catheter) and a catheter housing 104. Description for each of the primary components of the intermittent-catheter assembly 100 (i.e., the intermittent catheter 102 and the catheter housing 104) is set forth, in turn, below. Following the description for the primary components of the intermittent-catheter assembly 100 is description for additional features of the intermittent-catheter assembly 100.

The intermittent catheter 102 includes a proximal piece 106 including a neck 108, a cap 110 configured to cap a proximal opening 112 of the proximal piece 106, and a catheter tube 114 fluidly connected to the proximal piece 106.

The proximal piece 106 is configured to provide a handle for holding the intermittent-catheter assembly 100 while voiding urine through the proximal opening 112 of the proximal piece 106. The proximal piece 106 includes a flange 116 with a gasket 118 (e.g., 'O'-ring) thereover in a proximal portion of the proximal piece 106. The gasket 118 is configured to sit between the flange 116 and the cap 110 and form a fluidly tight seal when the cap 110 caps the proximal piece 106.

The cap 110 (e.g., a flip-top cap) is configured to cap the proximal piece 106 when not actively placing the intermittent catheter 102 for voiding urine, voiding urine, or removing the intermittent catheter 102 after voiding urine. The cap 110 is coupled to the proximal piece 106 by a living hinge 120. The cap 110 is configured to sit over the flange 116 of the proximal piece 106 such that the gasket 118 is between the cap 110 and the flange 116, thereby forming a fluidly tight seal when the cap 110 caps the proximal piece 106.

The cap 110 is also configured for effectuating an after-use storage state of the intermittent-catheter assembly 100 as set forth below. Indeed, the cap 110 includes a receptacle 122 for the ribbed portion 136 of the distal piece 130 of the catheter housing 104 set forth below for effectuating the after-use storage state of the intermittent-catheter assembly 100. The after-use storage state of the intermittent-catheter assembly 100 prevents urine leakage from the intermittent-catheter assembly 100 after voiding urine therewith. (See, for example, FIGS. 9 and 10.)

The catheter tube 114 is configured for insertion into a urethra for voiding urine from a bladder. The catheter tube 114 in one embodiment includes a plurality of eyelets 124 proximate a catheter tip 126. The eyelets 124 are fluid communication with the proximal opening 112 of the proximal piece 106 by way of a catheter-tube lumen 128 extending along a length of the catheter tube 114. Although two eyelets 124 are shown, any number or shape of openings are possible and within the scope of the invention, such as one large opening, more than two openings, etc. Also, the one-or-more openings can be spaced around the circumference of the catheter tube 114.

The catheter housing 104 includes a distal piece 130, an internal piece 132, and a sheath 134. An entirety of the catheter tube 114 is disposed in the catheter housing 104 in the packaged state of the intermittent-catheter assembly 100 as shown in FIGS. 1 and 2. However, the catheter housing 104 is around at least a portion of the catheter tube 114 in an any state of the intermittent-catheter assembly 100. (See, for example, FIGS. 1 and 2, 4, and 10.)

The distal piece 130 is configured to form the two-piece handle 144 with the internal piece 132 as set forth below for placing the intermittent catheter 102. The distal piece 130 is thusly slidably disposed around the catheter tube 114 for sliding the distal piece 130 to the internal piece 132.

The distal piece 130 is also configured for effectuating the after-use storage state of the intermittent-catheter assembly 100 as set forth below. Indeed, the distal piece 130 includes a ribbed portion 136 in a distal portion of the distal piece 130 for effectuating the after-use storage state of the intermittent-catheter assembly 100. Again, the after-use storage state of the intermittent-catheter assembly 100 prevents urine leakage from the intermittent-catheter assembly 100 after voiding urine therewith. (See, for example, FIGS. 9 and 10.)

The distal piece 130 is also configured for mitigating liquid (e.g., water, lubricant, or a combination thereof) migration into the eyelets 124 of the catheter tube 114, through the lumen 128 of the catheter tube 114, and out the proximal opening 112 of the proximal piece 106 when uncapped or out of a distal opening 138 of the distal piece 130 when the foil seal 150 is removed, each of which mitigates any mess that might otherwise occur when a user commences using the intermittent-catheter assembly 100. Indeed, the distal piece 130 includes a chamber 140 or a receptacle 142 for mitigating the liquid migration as set forth below.

Figures 9, 10:
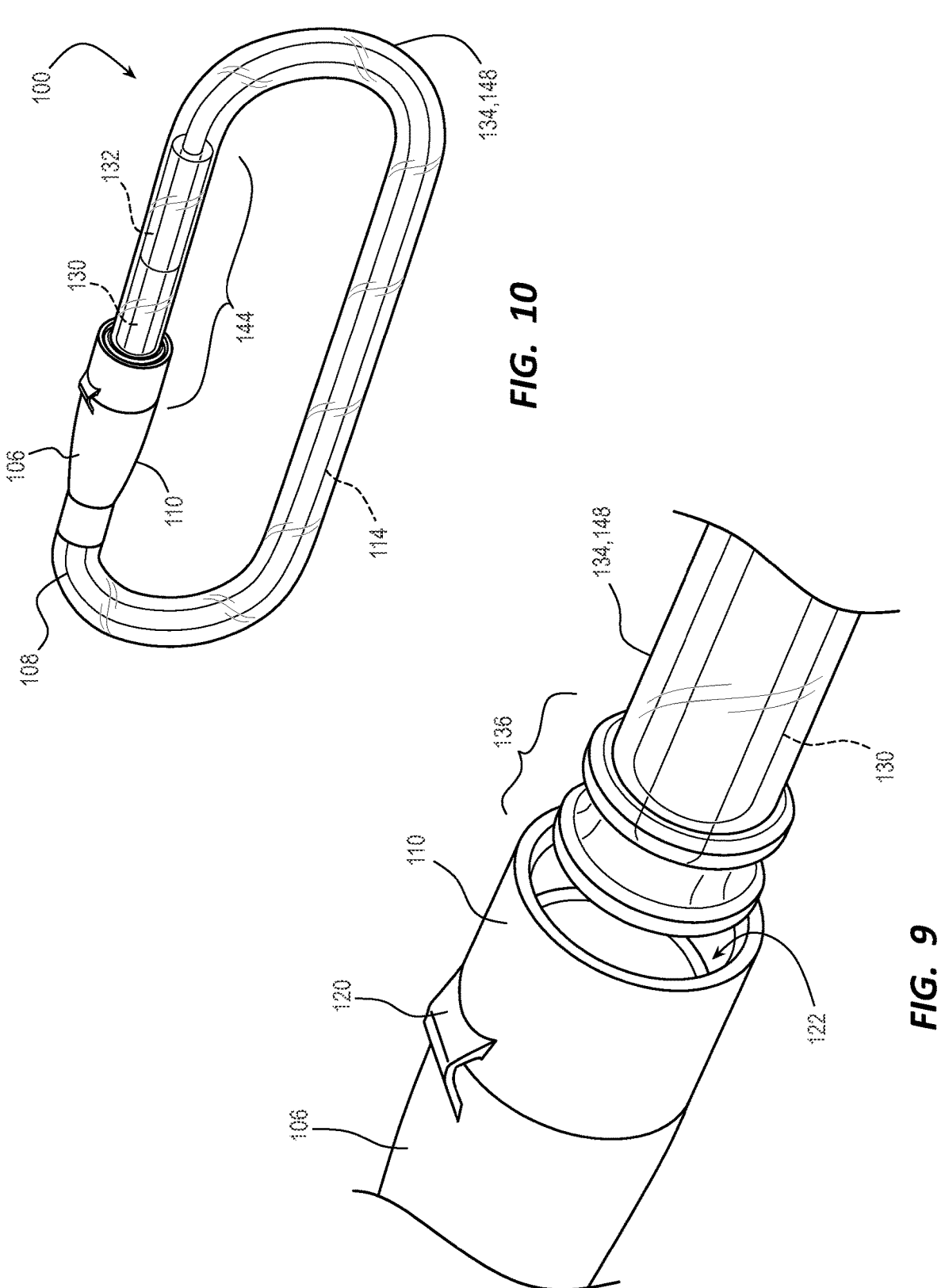
FIG. 9 illustrates a detailed view of joining a distal piece of a catheter housing of the intermittent-catheter assembly of FIG. 1 to a cap of an intermittent catheter of the intermittent-catheter assembly in accordance with some embodiments.
FIG. 10 illustrates a perspective view of the distal piece inserted into the cap of the intermittent catheter forming an after-use storage state of the intermittent-catheter assembly of FIG. 1 in accordance with some embodiments.

The internal piece 132 is configured to form a two-piece handle 144 with the distal piece 130 for at least placing the intermittent catheter 102. The internal piece 132 is thusly slidably disposed around the catheter tube 114 for independently sliding the internal piece 132 or sliding the internal piece 132 together with the distal piece 130. Indeed, the distal piece 130 and the internal piece 132 form the two-piece handle 144 for placing the intermittent catheter 102 when at least the distal piece 130 is proximally slid over the catheter tube 114 to the internal piece 132, which, incidentally, also exposes a distal portion of the catheter tube 114 for placing the intermittent catheter 102, or the internal piece 132 is distally slid over the catheter tube 114 to the distal piece 130. FIG. 4 illustrates the former in which the two-piece handle 144 is in a proximal position of the intermittent-catheter assembly 100 for the pre-insertion state thereof such as after the catheter tube-exposing step of the method set forth below, the insertion state thereof such as during the urine-voiding step of the method set forth below, or in the post-insertion state thereof such as after the catheter tube-removing step of the method set forth below. FIG. 10 illustrates the latter in which the two-piece handle 144 is in a distal position of the intermittent-catheter assembly 100 for the after-use storage state thereof.

The internal piece 132 is also configured to provide an internal structural support for the sheath 134. Indeed, the internal piece 132 is coupled to the sheath 134 between the distal portion 146 of the sheath 134 and the proximal portion 148 of the sheath 134 set forth below providing structural support to the sheath 134.

The sheath 134 is configured to maintain sterility of the catheter tube 114 in at least the packaged state of the intermittent-catheter assembly 100, as well as retain urine in the after-use storage state of the intermittent-catheter assembly 100.

The sheath 134 is collapsible for transitioning between different states of the intermittent-catheter assembly 100. The sheath 134 includes a distal portion 146 coupled to the distal piece 130, a proximal portion 148 coupled to the neck 108 of the proximal piece 106, a portion between the distal portion 146 and the proximal portion 148 of the sheath 134 (e.g., a medial portion of the sheath 134) coupled to the internal piece 132. The proximal portion 148 of the sheath 134 is pleated or bellowed for extension over the catheter tube 114 in the after-use storage state of the intermittent-catheter assembly 100. (See FIG. 10.) However, the distal portion 146 of the sheath 134 need not pleated or bellowed as shown in the illustrated embodiment.

The intermittent-catheter assembly 100 further includes a removable foil seal 150 over the distal opening 138 of the distal piece 130 of the catheter housing 104 in the packaged state of the intermittent-catheter assembly 100. (See FIGS. 1 and 2.) The foil seal 150 is configured to maintain sterility of the intermittent catheter 102 prior to use thereof.

The intermittent-catheter assembly 100 can further include a liquid (e.g., a lubricant 152, water 153, or a combination thereof) disposed in the intermittent-catheter assembly 100 in a sheath lumen 154 between the catheter tube 114 and the sheath 134 for lubricating the catheter tube 114. The foil seal 150 is further configured to retain the liquid in the intermittent-catheter assembly 100 while the intermittent-catheter assembly 100 is in the packaged state thereof. Additional or alternative lubricating means for lubricating the catheter tube 114 are respectively shown in FIGS. 6A-6C, each of which includes a liquid-retaining means for retaining the liquid (e.g., the lubricant 152, the water 153, or the combination thereof) in the intermittent-catheter assembly 100 as well.

FIGS. 6A-6C illustrate the longitudinal cross-section of the distal portion of the intermittent-catheter assembly 100 respectively including a lubricant-filled chamber 140 in the distal piece 130, a lubricating sponge-filled chamber 140 in the distal piece 130, and a lubricating sponge-filled receptacle 142 in the distal piece 130 in accordance with some embodiments.

The lubricating means shown in FIGS. 6A-6C is configured for lubricating the catheter tube 114 as it passes through the chamber 140 or the receptacle 142 (e.g., as the distal piece 130 is proximally slid over the catheter tube 114). The associated liquid-retaining means is configured for mitigating the liquid (e.g., the lubricant 152, the water 153, or the combination thereof) from migrating into the eyelets 124 of the catheter tube 114, through the lumen 128 of the catheter tube 114, and out of the proximal opening 112 of the proximal piece 106 when uncapped or migrating out of the distal opening 138 of the distal piece 130 when the foil seal 150 is removed. Mitigating the liquid from migrating out of the proximal opening 112 of the proximal piece 106 or the distal opening 138 of the distal piece 130 mitigates any mess that might otherwise occur when a user commences using the intermittent-catheter assembly 100 (e.g., uncapping the cap 110 capping the proximal opening 112 of the proximal piece 106 of the intermittent catheter 102, removing the foil seal 150 from the distal opening 138 of the distal piece 130, etc.).

As shown, the distal piece 130 of the intermittent-catheter assembly 100 in each figure of FIGS. 6A and 6B includes the chamber 140, wherein the chamber 140 shown in FIG. 6A includes the liquid (e.g., the lubricant 152, the water 153, or the combination thereof) for lubricating the catheter tube 114 as needed, and wherein the chamber 140 shown in FIG. 6B includes a lubricating sponge 156 (e.g., a sponge impregnated with the liquid) for lubricating the catheter tube 114 as needed. Due to a narrow cylindrical gap 158 between the chamber 140 and the sheath lumen 154 proximal of the distal piece 130, ingress of any of the liquid into the chamber 140 from the sheath lumen 154 is minimal to none, particularly if the liquid is relatively viscous (e.g., a lubricating gel). This limits an amount of the liquid that can migrate into the eyelets 124 of the catheter tube 114 and out the proximal opening 112 of the proximal piece 106 when uncapped. Similarly, a narrow cylindrical gap 160 between the chamber 140 and the distal opening 138 of the distal piece 130 limits egress of any of the liquid out of the chamber 140, thereby limiting an amount of the liquid that can migrate out of the distal opening 138 of the distal piece 130 when the foil seal 150 is removed. As to the lubricating sponge 156, the lubricating sponge 156 further mitigates ingress or egress of any of the liquid into or out of the chamber 140 on account of its rate-limiting wicking mechanism. Furthermore, the lubricating sponge 156 does not wick any of the liquid into the chamber 140 from the sheath lumen 154 when the lubricating sponge is already saturated.

While the distal piece 130 of the intermittent-catheter assembly 100 in FIG. 6C includes the receptacle 142 instead of the chamber 140 of the intermittent-catheter assembly 100 shown in FIG. 6A or 6B, the receptacle 142 still limits egress of any of the liquid (e.g., the lubricant 152, the water 153, or the combination thereof) out of the receptacle 142 through the narrow cylindrical gap 160 between the receptacle 142 and the distal opening 138 of the distal piece 130 like the chamber 140 set forth above. In addition, a lubricating sponge 162 having a distal portion disposed in the liquid in the sheath lumen 154 also mitigates ingress or egress of any of the liquid into or out of the receptacle 142 on account of its rate-limiting wicking mechanism and reluctance to wick any of the liquid into the receptacle 142 from the sheath lumen 154 when the lubricating sponge is already saturated therewith.

FIG. 9 illustrates a detailed view of joining the distal piece 130 of the catheter housing 104 to the cap 110 of the intermittent catheter 102 in accordance with some embodiments. FIG. 10 illustrates a perspective view of the distal piece 130 of the catheter housing 104 inserted into the cap 110 of the intermittent catheter 102 forming the after-use storage state of the intermittent-catheter assembly 100 in accordance with some embodiments.

As alluded to above, the cap 110 and the distal piece 130 are both configured to effectuate the after-use storage state of the intermittent-catheter assembly 100. Indeed, the cap 110 includes the receptacle 122 and the distal piece 130 includes the ribbed portion 136, which receptacle 122 is configured to accept the ribbed portion 136 inserted therein when the intermittent-catheter assembly 100 is bent in an end-to-end fashion akin to that of a dragon or serpent eating its own tail (e.g., the ouroboros of ancient Egyptian iconography). The distal piece 130 is further configured to effectuate the after-use storage state of the intermittent-catheter assembly 100 together with the internal piece 132 of the catheter housing 104 in the two-piece handle 144. Indeed, when the two-piece handle 144 is in the distal position of the intermittent-catheter assembly 100 in the after-use storage state thereof as shown in FIG. 10, the two-piece handle 144 provides structural support to counter circumferential stress in that location while the intermittent-catheter assembly 100 is in the after-use storage state thereof. Again, the after-use storage state of the intermittent-catheter assembly 100 prevents urine leakage from the intermittent-catheter assembly 100 after voiding urine therewith.

Figures 13, 14, 15:
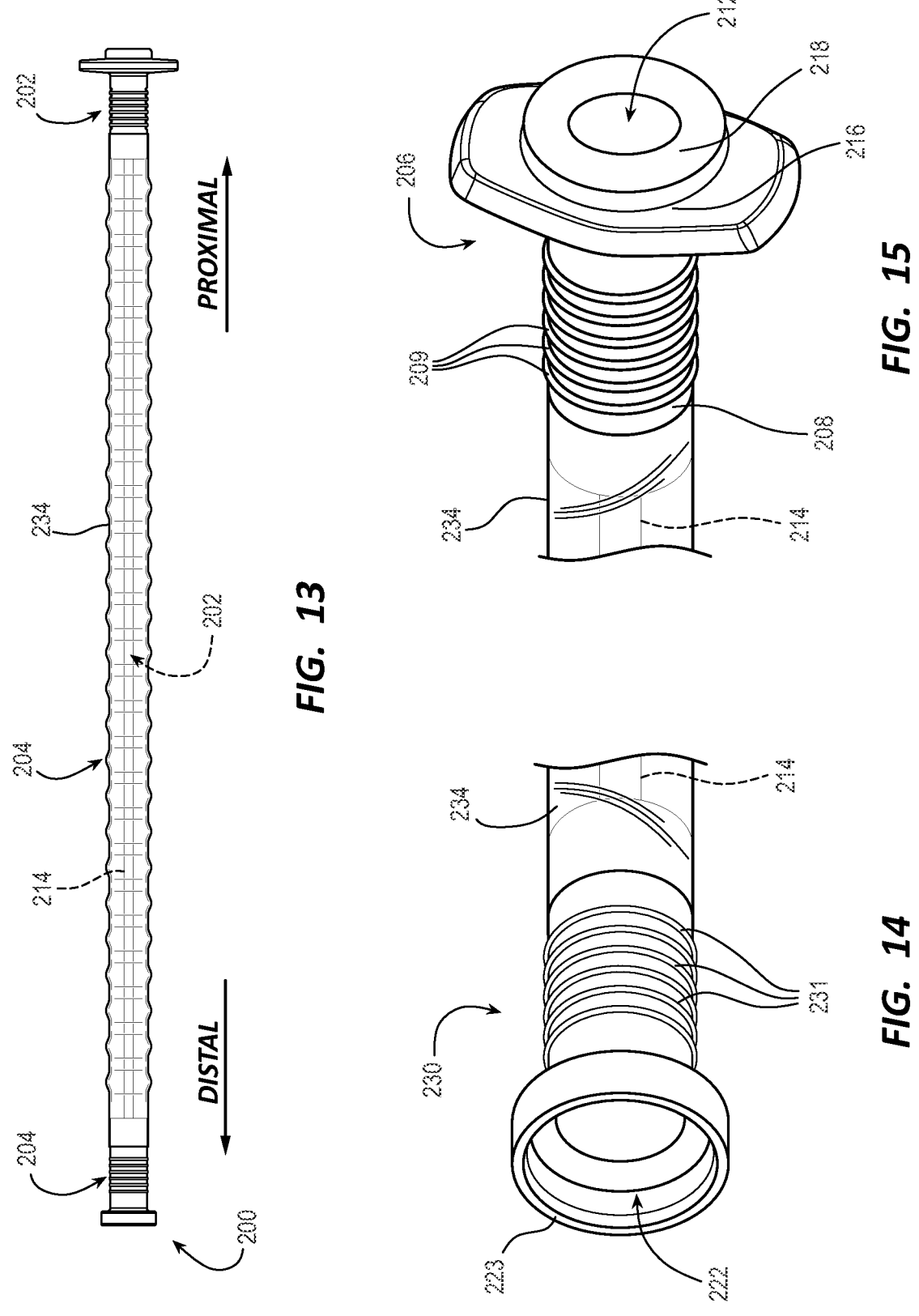
FIG. 13 illustrates a side view of another intermittent-catheter assembly in accordance with some embodiments.
FIG. 14 illustrates a perspective view of a distal portion of the intermittent-catheter assembly of FIG. 13 in accordance with some embodiments.
FIG. 15 illustrates a perspective view of a proximal portion of the intermittent-catheter assembly of FIG. 13 in accordance with some embodiments.
Figure 16:
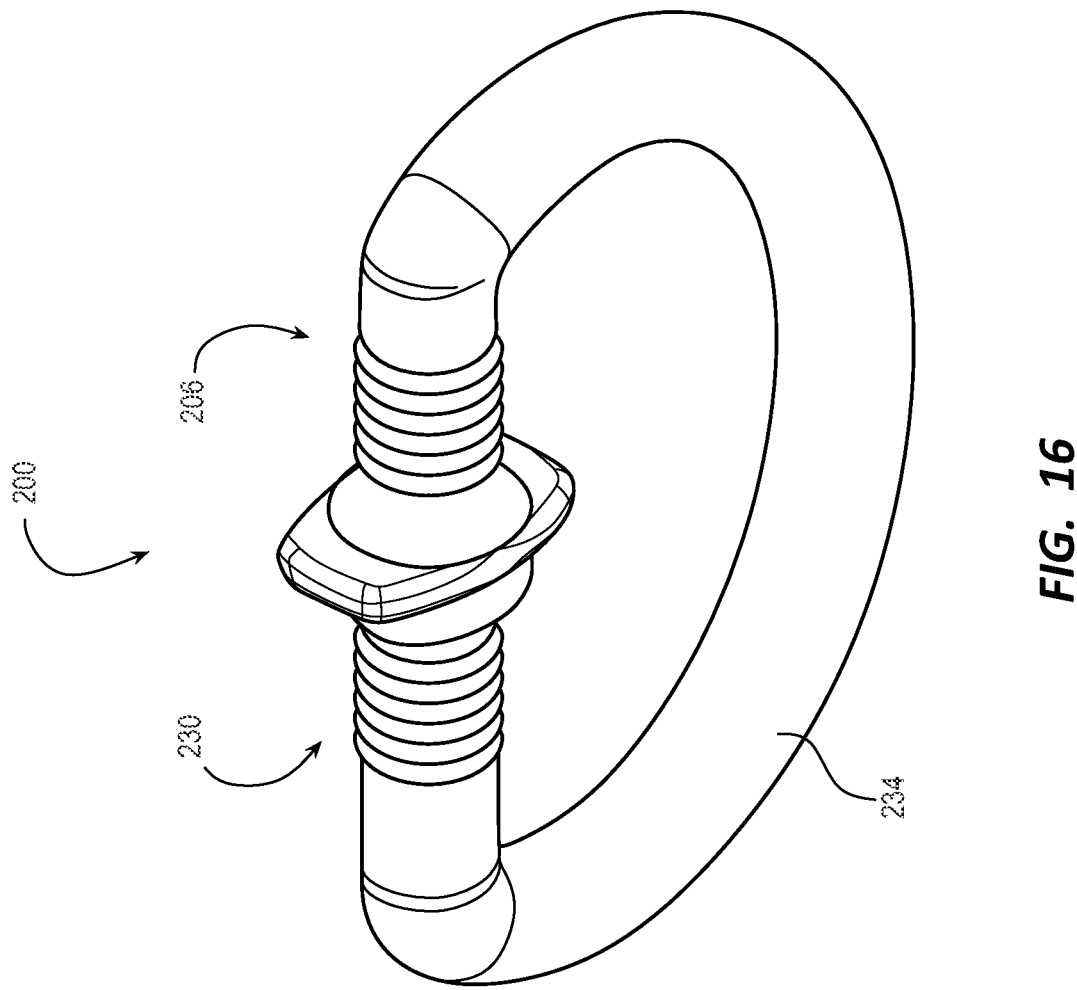
FIG. 16 illustrates a perspective view of a distal piece of the catheter housing inserted into a proximal piece of the intermittent catheter forming a packaged state or an after-use storage state of the intermittent-catheter assembly of FIG. 13 in accordance with some embodiments.
Figure 17:
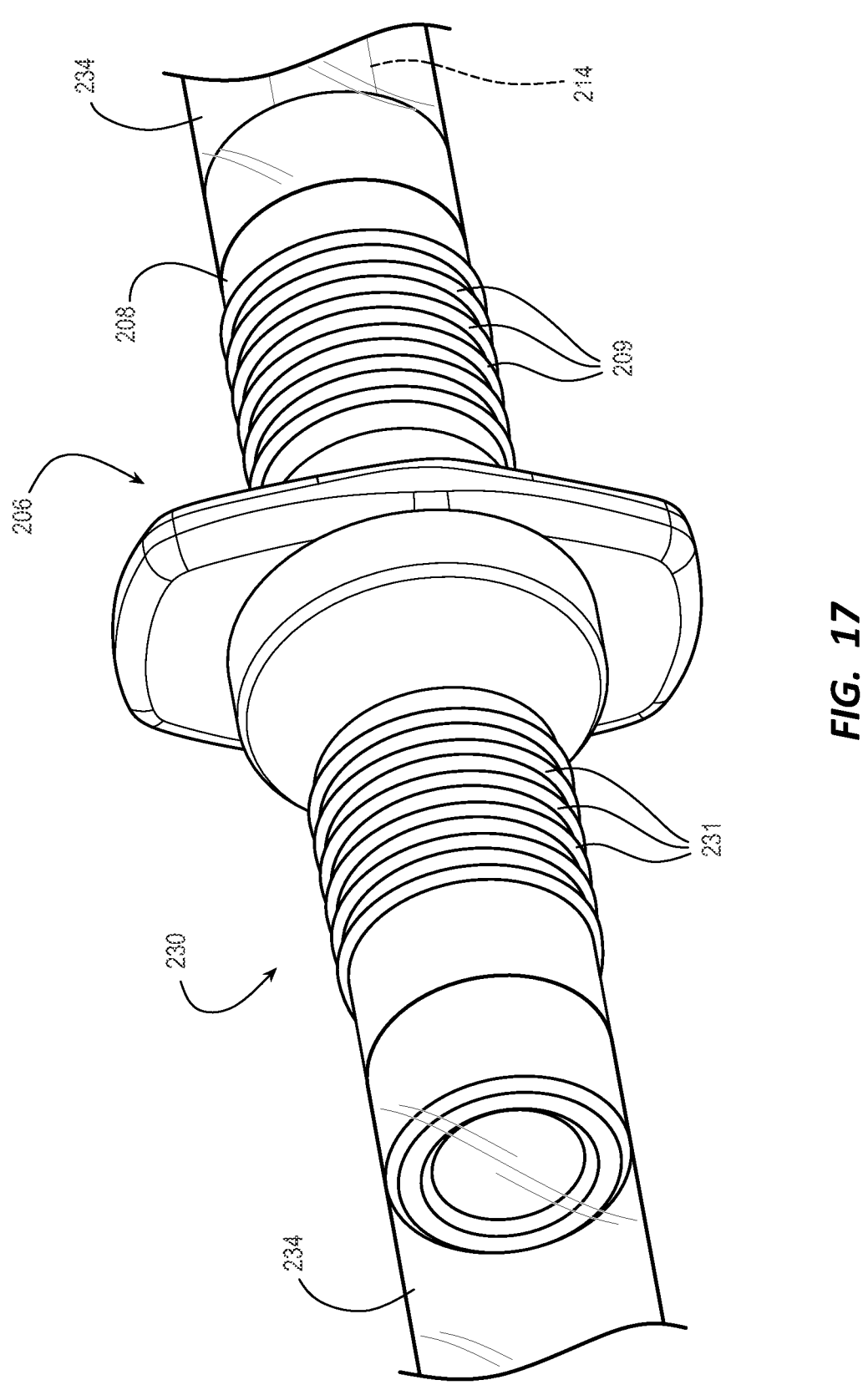
FIG. 17 illustrates a detailed view of the distal piece inserted into the proximal piece of the intermittent catheter forming the packaged state or the after-use storage state of the intermittent-catheter assembly of FIG. 13 in accordance with some embodiments.

FIGS. 13-17 illustrate various views of an intermittent-catheter assembly 200 in various states accordance with some embodiments. For example: The intermittent-catheter assembly 200 of FIG. 13 is in a pre-insertion state thereof such as before the catheter tube-exposing step of the method set forth below. Alternatively, the intermittent-catheter assembly 200 of FIG. 13 is in a pre-joined state thereof such as before the joining step of the method set forth below. The intermittent-catheter assembly 200 of FIG. 16 is in a packaged state thereof as set forth below. Alternatively, the intermittent-catheter assembly 200 of FIG. 16 is in an after-use storage state thereof as set forth below.

As shown, the intermittent-catheter assembly 200 includes, in some embodiments, an intermittent catheter 202 (e.g., a male intermittent catheter) and a catheter housing 204 coupled to the intermittent catheter 202. Description for each of the primary components of the intermittent-catheter assembly 200 (i.e., the intermittent catheter 202 and the catheter housing 204) is set forth, in turn, below.

The intermittent catheter 202 includes a proximal piece 206 including a neck 208 as well as a catheter tube 214 fluidly connected to the proximal piece 206.

The proximal piece 206 is configured to provide a handle or a portion of the two-piece handle set forth below for holding the intermittent-catheter assembly 200 while voiding urine through the proximal opening 212 of the proximal piece 206. Indeed, the proximal piece 206 includes a medial portion having circumferential ridges 209 configured for gripping the proximal piece 206 while voiding urine through the proximal opening 212 of the proximal piece 206. The proximal piece 206 includes a flange 216 with an integrated gasket 218 (e.g., an integrated 'O'-ring) thereover in a proximal portion of the proximal piece 206. The gasket 218 is configured to form a fluidly tight seal when the flange 216 is inserted into the receptacle 222 set forth below. Notably, the circumferential ridges 209 are also configured for gripping the proximal piece 206 when inserting the flange 216 into the receptacle 222.

The catheter tube 214 is configured for insertion into a urethra for voiding urine from a bladder. As to insertion into the urethra, the catheter tube 214 includes an activated or wetted hydrophilic coating over the catheter tube 214. As to voiding urine from the bladder, the catheter tube 214 in one embodiment includes a plurality of eyelets proximate a catheter tip. (See, for example, the eyelets 124 and the catheter tip 126 of the catheter tube 114 in FIG. 4.) The eyelets are fluid communication with the proximal opening 212 of the proximal piece 206 by way of a catheter-tube lumen extending along a length of the catheter tube 214. (See, for example, the catheter-tube lumen 128 of the catheter tube 114 in FIGS. 6A-6C.)

Figure 19:
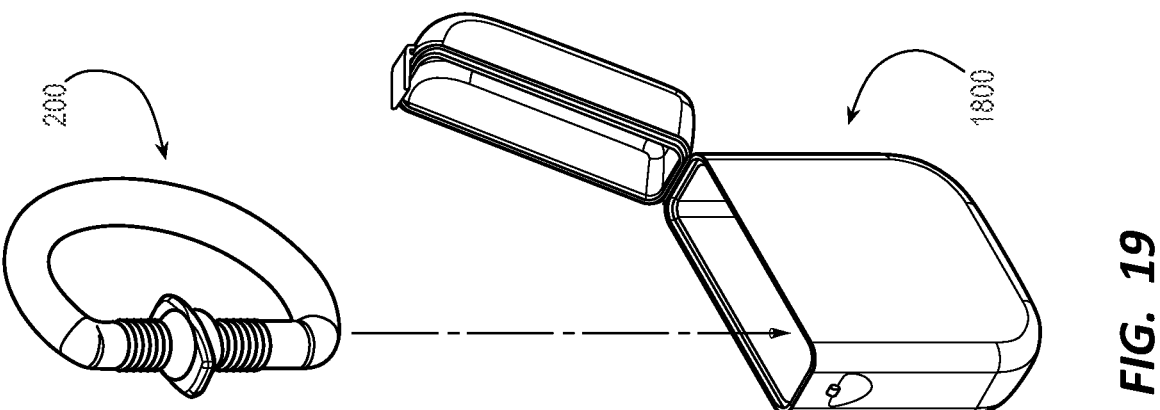
FIG. 19 illustrates removal of the intermittent catheter assembly of FIG. 13 from the carrying case of FIG. 18 or disposal of the intermittent catheter assembly in the carrying case in accordance with some embodiments.

The catheter housing 204 includes a distal piece 230 and a sheath 234. An entirety of the catheter tube 214 is disposed in the catheter housing 204 in the packaged state of the intermittent-catheter assembly 200 as shown in FIGS. 16 and 19. However, the catheter housing 204 is around at least a portion of the catheter tube 214 in an any state of the intermittent-catheter assembly 200.

The distal piece 230 is slidably disposed around the catheter tube 214 for proximally sliding the distal piece 230 over the catheter tube 214 to the proximal piece 206 to unsheath the catheter tube 214 for catheterization therewith. The distal piece 230 is slidably disposed around the catheter tube 214 for distally sliding the distal piece 230 over the catheter tube 214 away from the proximal piece 206 to resheath the catheter tube 214 after catheterization therewith. Like the proximal piece 206, the distal piece 230 includes a medial portion having circumferential ridges 231 configured for gripping the distal piece 230 while proximally or distally sliding the distal piece 230 over the catheter tube 214. In addition, the distal piece 230 is configured to form a two-piece handle with the proximal piece 206 when proximally slid over the catheter tube 214 to the proximal piece 206. (See, for example, the proximal piece 106 and the distal piece 130 of the intermittent-catheter assembly 100 in FIG. 4.) Aided by the circumferential ridges 209 and 231 of both the proximal and distal pieces 206 and 230, the two-piece handle is configured for holding the intermittent-catheter assembly 200 while voiding urine through the proximal opening 212 of the proximal piece 206. Notably, the circumferential ridges 231 are also configured for gripping the distal piece 230 when inserting the flange 216 into the receptacle 222 set forth below.

The distal piece 230 is also configured for effectuating both the packaged state and the after-use storage state of the intermittent-catheter assembly 200. Indeed, the distal piece 230 includes a flared receptacle 222 with an inner lip 223 in a distal portion of the distal piece 230 for forming a fluidly tight seal when the flange 216 is inserted into the receptacle 222. Insertion of the flange 216 into the receptacle 222 effectuates both the original, packaged state of the intermittent-catheter assembly 200 as well as the after-use storage state of the intermittent-catheter assembly 200. The after-use storage state of the intermittent-catheter assembly 200 is configured to prevent urine leakage from the intermittent-catheter assembly 200 of any residual urine present in the intermittent catheter 202 after voiding urine therewith. (See, for example, FIGS. 16 and 19.)

The sheath 234 is configured to retain the hydrophilic coating over the catheter tube 214 in the packaged state of the intermittent-catheter assembly 200, maintain a moisture content of the hydrophilic coating in the packaged state of the intermittent-catheter assembly 200, and maintain sterility of the intermittent catheter 202 in the packaged state of the intermittent-catheter assembly 200 prior to use thereof. The sheath 234 is also configured to prevent urine leakage from the intermittent-catheter assembly 200 in the after-use storage state of the intermittent-catheter assembly 200. However, other features of the intermittent-catheter assembly 200 for effectuating the foregoing states of the intermittent-catheter assembly 200 also contribute to the foregoing as well.

The sheath 234 is collapsible for transitioning between different states of the intermittent-catheter assembly 200. The sheath 234 includes a distal portion coupled to the distal piece 230 and a proximal portion coupled to the neck 208 of the proximal piece 206. The sheath 234 is pleated or bellowed to facilitate transitioning between the different states of the intermittent-catheter assembly 200 including the packaged state of the intermittent-catheter assembly 200 and the after-use storage state of the intermittent-catheter assembly 200.

As alluded to above, the distal piece 230 and the proximal piece 206 are both configured to effectuate the packaged state of the intermittent-catheter assembly 200 and the after-use storage state of the intermittent-catheter assembly 200. Indeed, the distal piece 230 includes the receptacle 222 and the proximal piece 206 includes the flange 216, which receptacle 222 is configured to accept the flange 216 inserted therein when the intermittent-catheter assembly 200 is bent in an end-to-end fashion akin to that of a dragon or serpent eating its own tail (e.g., the ouroboros of ancient Egyptian iconography). In the packaged state of the intermittent-catheter assembly 200, the hydrophilic coating over the catheter tube 214 is retained, the moisture content of the hydrophilic coating is maintained, and sterility of the intermittent catheter 202 is maintained prior to use thereof. In the after-use storage state of the intermittent-catheter assembly 200, urine leakage from the intermittent-catheter assembly 200 is prevented.

Packaged Intermittent-Catheter Assemblies

Figures 11, 12:
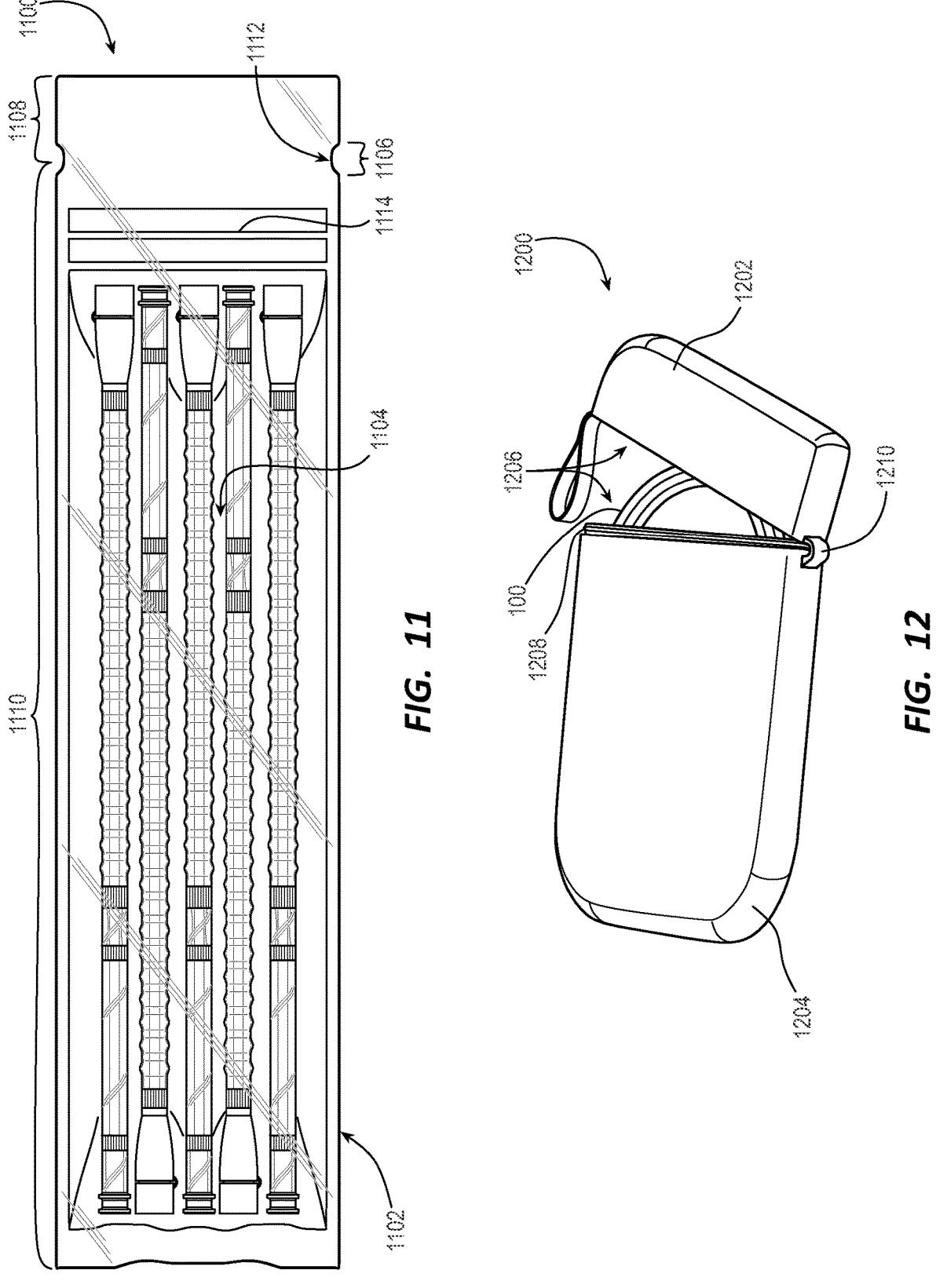
FIG. 11 illustrates a package of intermittent-catheter assemblies such as the intermittent catheter assembly of FIG. 1 in accordance with some embodiments.
FIG. 12 illustrates a carrying case for one or more intermittent-catheter assemblies such as the intermittent catheter assembly of FIG. 1 in accordance with some embodiments.

FIG. 11 illustrates a package of intermittent-catheter assemblies 1000 in accordance with some embodiments.

As shown the package of intermittent-catheter assemblies 1000 includes, in some embodiments, resealable packaging 1102 and a set of intermittent-catheter assemblies 1104 disposed therein.

The packaging 1102 includes a kerfed portion 1106, a removable piece 1108, and a main body 1110.

The kerfed portion 1106 of the packaging 1102 includes kerfs 1112 configured for tearing the removable piece 1108 off the package 1000 or the packaging 1102 thereof.

The main body 1110 includes a cavity and a ziplock 1114 in an end portion of the main body 1110 for resealing the package 1000 or the packaging 1102 thereof after removing the removable piece 1108.

The set of intermittent-catheter assemblies 1104 (e.g., about a day's supply) are disposed in the cavity of the packaging 1102. Each intermittent-catheter assembly 100 of the set of intermittent-catheter assemblies 1104 is disposed in the packaging 1102 in its extended form to minimize curvature thereof, which curvature could complicate insertion. IN addition, each intermittent-catheter assembly 100 is disposed in the packaging 1102 in the packaged state thereof as set forth above.

Carrying Cases

FIG. 12 illustrates a carrying case 1200 for one or more intermittent-catheter assemblies such as the intermittent-catheter assembly 100 in accordance with some embodiments.

As shown, the carrying case 1200 is a multiple-use hard-shell carrying case including, in some embodiments, a top 1202, a main body 1204, and a cavity 1206 formed between the top 1202 and the main body 1204. The carrying case 1200 including the top 1202 and the main body 1204 of the carrying case 1200 can be rigid to prevent damage to any intermittent-catheter assemblies disposed therein and promote longer-term use of the carrying case.

The top 1202 of the carrying case 1200 is configured to sit over a flange 1208 about an open end of the main body 1204 of the carrying case 1200, which facilitates keeping the carrying case 1200 closed by way of an interference fit between the top 1202 and the flange 1208. The top 1202 of the carrying case 1200 is coupled to the main body 1204 of the carrying case 1200 by a living hinge 1210, which facilitates fitting the top 1202 over the flange 1208 of the main body 1204, as well as eliminates misplacement of the top 1202.

The cavity 1206, which is formed between the main body 1204 of the carrying case 1200 and the top 1202 of the carrying case 1200 when the top 1202 is fitted over the open end of the main body 1204, is configured to contain the one-or-more intermittent-catheter assemblies in one or more states thereof.

Figure 18:
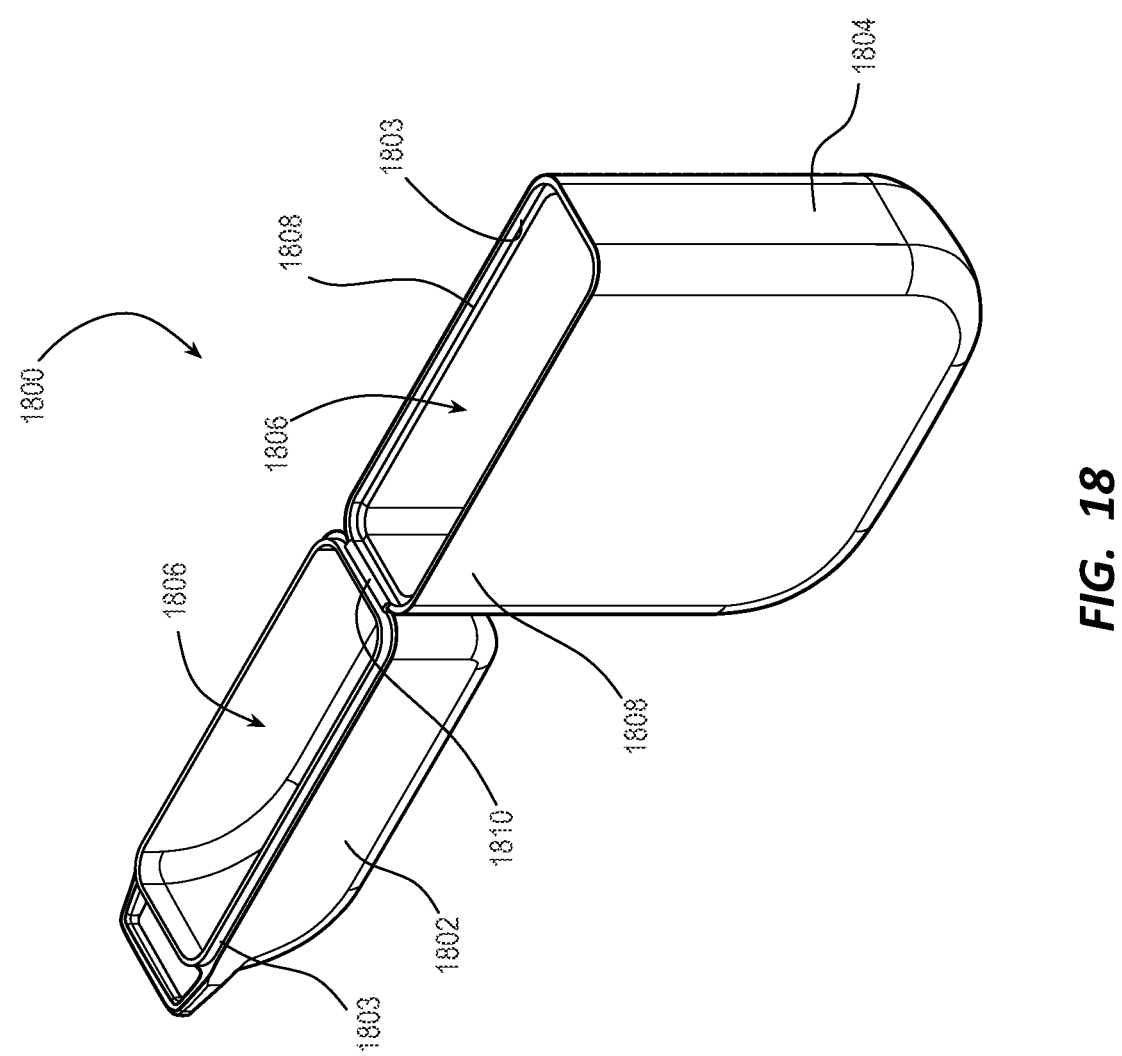
FIG. 18 illustrates a carrying case for one or more intermittent-catheter assemblies such as the intermittent catheter assembly of FIG. 13 in accordance with some embodiments.

FIG. 18 illustrates a carrying case 1800 for one or more intermittent-catheter assemblies such as the intermittent-catheter assembly 200 in accordance with some embodiments.

Like the carrying case 1200, the carrying case 1800 is a multiple-use hard-shell carrying case including, in some embodiments, a top 1802, a main body 1804, and a cavity 1806 formed between the top 1802 and the main body 1804. The carrying case 1800 including the top 1802 and the main body 1804 of the carrying case 1800 can be rigid to prevent damage to any intermittent-catheter assemblies disposed therein and promote longer-term use of the carrying case 1800.

A perimetrical edge 1803 extending from the top 1802 of the carrying case 1800 is configured to sit on an inner lip 1808 about an open end of the main body 1804 of the carrying case 1800, which facilitates keeping the carrying case 1800 closed by way of an interference fit between the perimetrical edge 1803 and a perimetrical edge 1805 extending from the main body 1804 over the inner lip 1808. The top 1802 of the carrying case 1800 is coupled to the main body 1804 of the carrying case 1800 by a living hinge 1810, which facilitates fitting the top 1802 over the main body 1804, as well as eliminates misplacement of the top 1802.

The cavity 1806, which is formed between the main body 1804 of the carrying case 1800 and the top 1802 of the carrying case 1800 when the top 1802 is fitted over the open end of the main body 1804, is configured to contain the one-or-more intermittent-catheter assemblies in one or more states thereof.

Methods

Methods of the intermittent-catheter assembly 100 of FIGS. 1-10 include methods of using the intermittent-catheter assembly 100. For example, a method of the intermittent-catheter assembly 100 includes, in some embodiments, a catheter obtaining step, an uncapping step, a catheter tube-exposing step, a catheter tube-inserting step, and a urine-voiding step.

The catheter obtaining step includes obtaining the intermittent-catheter assembly 100 in the packaged state thereof. The intermittent-catheter assembly 100 in the packaged state thereof can be further packaged in the package of intermittent-catheter assemblies 1100 providing about a day's supply thereof. As set forth above, the intermittent-catheter assembly 100 includes the catheter housing 104 including the sheath 134 around at least the catheter tube 114 of the intermittent catheter 102.

The uncapping step includes uncapping the cap 110 capping the proximal opening 112 of the proximal piece 106 of the intermittent catheter 102. A set forth above, the cap 110 is coupled to the proximal piece 106 by the living hinge 120.

The method further includes a foil-removing step. The foil-removing step includes removing the foil seal 150 from the distal opening 138 of the distal piece 130 of the catheter housing 104 before the catheter tube-exposing step.

The catheter tube-exposing step includes exposing an insertable portion of the catheter tube 114, which is effectuated by proximally sliding the distal piece 130 of the catheter housing 104 over the catheter tube 114. Proximally sliding the distal piece 130 of the catheter housing 104 over the catheter tube 114 in accordance with the catheter tube-exposing step includes sliding the distal piece 130 to the internal piece 132 of the catheter housing 104 to form the two-piece handle 144 for inserting the catheter tube 114 into the urethra. The distal portion 146 of the sheath 134 collapses between the distal piece 130 and the internal piece 132 when the distal piece 130 is slid to the internal piece 132. The catheter tube-exposing step further includes proximally sliding the internal piece 132 of the catheter housing 104 or the two-piece handle 144 over the catheter tube 114 to the proximal piece 106 of the intermittent catheter 102. The proximal portion 148 of the sheath 134 collapses between the internal piece 132 and the proximal piece 106 when the internal piece 132 or the two-piece handle 144 is slide to the proximal piece 106.

The catheter tube-inserting step includes inserting the catheter tube 114 into a urethra.

The urine-voiding step includes voiding urine from a bladder upon proper placement of the intermittent catheter 102 therein.

The method further includes a catheter tube-removing step, a capping step, and a catheter tube-covering step.

The catheter tube-removing step includes removing the catheter tube 114 from the urethra after the urine-voiding step.

The capping step includes capping the proximal opening 112 of the proximal piece 106 with the cap 110 after the catheter tube-removing step.

The catheter tube-covering step includes covering the insertable portion of the catheter tube 114 by distally sliding the distal piece 130 of the catheter housing 104 over the catheter tube 114.

The method can further include a joining step. The joining step includes inserting the ribbed portion 136 of the distal piece 130 of the catheter housing 104 into the receptacle 122 in the proximal portion of the cap 110 by bending proximal and distal ends of the intermittent-catheter assembly 100 toward each other. The joining step forms the after-use storage state of the intermittent-catheter assembly 100 configured to prevent urine leakage from the intermittent-catheter assembly 100 after the urine-voiding step.

The method further can further include a catheter assembly-storing step. The catheter assembly-storing step includes placing the intermittent-catheter assembly 100 in the after-use storage state thereof into the carrying case 1200 or another container for future disposal of the intermittent-catheter assembly 100.

Methods of the intermittent-catheter assembly 200 of FIGS. 13-17 and 19 include methods of using the intermittent-catheter assembly 200. For example, a method of the intermittent-catheter assembly 200 includes, in some embodiments, a catheter-obtaining step, a flange-removing step, a catheter tube-exposing step, a catheter tube-inserting step, and a urine-voiding step.

The catheter-obtaining step includes obtaining the intermittent-catheter assembly 200 in the packaged state thereof. As set forth above, the intermittent-catheter assembly 200 includes the catheter housing 204 including the sheath 234 around at least the catheter tube 214 of the intermittent catheter, wherein the flange 216 is ouroborosly inserted in the receptacle 222 in the packaged state of the intermittent-catheter assembly 200. Notably, the intermittent-catheter assembly 200 in the packaged state thereof can be further packaged in the carrying case with about a day's supply of other intermittent-catheter assemblies.

The flange-removing step includes removing the flange 216 in the proximal portion of the proximal piece 206 of the intermittent catheter 202 from the flared receptacle 222 of the distal portion of the distal piece 230 of the catheter housing 204.

The catheter tube-exposing step includes exposing the insertable portion of the catheter tube 214 including proximally sliding the distal piece 230 over the catheter tube 214 toward the proximal piece 206. The sheath 234 collapses between the distal piece 230 and the proximal piece 206 with the sliding of the distal piece 230 over the catheter tube 214, thereby unsheathing the catheter tube 214. Notably, proximally sliding the distal piece 230 over the catheter tube 214 toward the proximal piece 206 forms a two-piece handle between the proximal and distal pieces 206 and 230 for the catheter tube-inserting step.

The catheter tube-inserting step includes inserting the catheter tube 214 into a urethra.

The urine-voiding step includes voiding urine from a bladder upon proper placement of the intermittent catheter 202 therein.

The method further includes a catheter tube-removing step, a catheter tube-resheathing step, a catheter assembly-bending step, and a storage state-forming step.

The catheter tube-removing step includes removing the catheter tube 214 from the urethra after the voiding of the urine from the bladder.

The catheter tube-resheathing step includes covering the insertable portion of the catheter tube 214 with the sheath 234 by distally sliding the distal piece 230 over the catheter tube 214, thereby resheathing the catheter tube 214.

The catheter assembly-bending step includes bending proximal and distal portions of the intermittent-catheter assembly 200 toward each other.

The storage state-forming step includes ouroborosly inserting the flange 216 of the proximal piece 206 into the receptacle 222 of the distal piece 230, thereby forming an after-use storage state of the intermittent-catheter assembly 200. The after-use storage state of the intermittent-catheter assembly 200 is configured to prevent urine leakage from the intermittent-catheter assembly 200 after the voiding of the urine from the bladder.

The method can further include a storing step. The storing step includes placing the intermittent-catheter assembly 200 in the after-use storage state thereof into the multiple-use hard-shell carrying case for future disposal of the intermittent-catheter assembly 200. The intermittent-catheter assembly 200 in the after-use storage state thereof can be stored of packaged in the carrying case with the day's supply of other intermittent-catheter assemblies set forth above.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An intermittent-catheter assembly, comprising:
an intermittent catheter including:
    a proximal piece including a neck;
    a cap coupled to the proximal piece of the intermittent catheter by a living hinge, the cap configured to cap a proximal opening of the proximal piece after voiding urine through the intermittent catheter; and
    a catheter tube fluidly connected to the proximal piece; and
a catheter housing coupled to the intermittent catheter, the catheter housing comprising:
    a distal piece including:
        a ribbed portion configured to ouroborosly insert into a receptacle located in a proximal portion of the cap coupled to the proximal piece of the intermittent catheter while the cap caps the proximal opening of the proximal piece; and
        a chamber or a receptacle including a lubricant or a lubricating sponge for lubricating the catheter tube when the distal piece is proximally slid over the catheter tube;

an internal piece slidably disposed around the catheter tube, wherein the distal piece and the internal piece form a slidable two-piece handle for placing the intermittent catheter after sliding the distal piece proximally over the catheter tube to the internal piece, thereby exposing a distal portion of the catheter tube; and
a collapsible sheath including a distal portion coupled to the distal piece and a proximal portion coupled to the neck of the proximal piece of the intermittent catheter, wherein an entirety of the catheter tube is disposed in the catheter housing in a packaged state of the intermittent-catheter assembly.

2. The intermittent-catheter assembly of claim 1, wherein the cap is configured to sit over a flange in a proximal portion of the proximal piece of the intermittent catheter, and wherein the flange includes a gasket thereover configured to sit between the cap and the proximal piece and form a fluidly tight seal when the cap caps the proximal piece.

3. The intermittent-catheter assembly of claim 1, wherein the distal piece inserted into the receptacle of the cap forms an after-use storage state of the intermittent-catheter assembly configured to prevent urine leakage from the intermittent-catheter assembly after voiding urine therewith.

4. The intermittent-catheter assembly of claim 1, wherein the catheter tube includes a plurality of eyelets proximate a catheter tip, the plurality of eyelets in fluid communication with the proximal opening of the proximal piece of the intermittent catheter.

5. The intermittent-catheter assembly of claim 1, further comprising a removable foil seal over a distal opening of the distal piece in the packaged state of the intermittent-catheter assembly, wherein the removable foil seal is configured to maintain sterility of the intermittent catheter prior to use thereof.

6. The intermittent-catheter assembly of claim 5, wherein the removable foil seal is further configured to retain the lubricant in the intermittent-catheter assembly while the intermittent-catheter assembly is in the packaged state thereof.

7. The intermittent-catheter assembly of claim 1, wherein the internal piece is coupled to the collapsible sheath between a proximal portion of the collapsible sheath and a distal portion of the collapsible sheath providing support thereto.

8. The intermittent-catheter assembly of claim 7, wherein the proximal portion of the collapsible sheath is pleated or bellowed, and wherein the distal portion of the collapsible sheath is not pleated or bellowed.

9. The intermittent-catheter assembly of claim 1, wherein the slidable two-piece handle has a proximal position over the catheter tube in an insertion state of the intermittent-catheter assembly.

10. The intermittent-catheter assembly of claim 9, wherein the slidable two-piece handle has a distal position over the catheter tube in an after-use storage state of the intermittent-catheter assembly.

11. An intermittent-catheter assembly, comprising:
an intermittent catheter including:
    a proximal piece including a neck;
    a cap coupled to the proximal piece of the intermittent catheter by a living hinge, the cap configured to cap a proximal opening of the proximal piece after voiding urine through the intermittent catheter; and
    a catheter tube fluidly connected to the proximal piece; and a catheter housing coupled to the intermittent catheter, the catheter housing comprising:

a distal piece configured to proximally slide over the catheter tube, the distal piece including a ribbed portion configured to ouroborosly insert into a receptacle located in a proximal portion of the cap coupled to the proximal piece of the intermittent catheter while the cap caps the proximal opening of the proximal piece;

an internal piece slidably disposed around the catheter tube, wherein the distal piece and the internal piece form a slidable two-piece handle for placing the intermittent catheter after sliding the distal piece proximally over the catheter tube to the internal piece, thereby exposing a distal portion of the catheter tube; and a collapsible sheath including a distal portion coupled to the distal piece and a proximal portion coupled to the neck of the proximal piece of the intermittent catheter, wherein an entirety of the catheter tube is disposed in the catheter housing in a packaged state of the intermittent-catheter assembly.

12. The intermittent-catheter assembly of claim 11, wherein the catheter tube includes a plurality of eyelets proximate a catheter tip, the plurality of eyelets in fluid communication with the proximal opening of the proximal piece of the intermittent catheter.

13. The intermittent-catheter assembly of claim 11, further comprising a removable foil seal over a distal opening of the distal piece in the packaged state of the intermittent-catheter assembly, wherein the removable foil seal is configured to maintain sterility of the intermittent catheter prior to use thereof.

14. The intermittent-catheter assembly of claim 13, wherein the removable foil seal is further configured to retain a lubricant in the intermittent-catheter assembly while the intermittent-catheter assembly is in the packaged state thereof.

15. The intermittent-catheter assembly of claim 14, wherein the distal piece includes a chamber or a receptacle including the lubricant for lubricating the catheter tube when the distal piece is proximally slid over the catheter tube.

16. The intermittent-catheter assembly of claim 11, wherein the internal piece is coupled to the collapsible sheath between a proximal portion of the collapsible sheath and a distal portion of the collapsible sheath providing support thereto.

17. The intermittent-catheter assembly of claim 16, wherein the proximal portion of the collapsible sheath is pleated or bellowed, and wherein the distal portion of the collapsible sheath is not pleated or bellowed.

18. The intermittent-catheter assembly of claim 11, wherein the cap is configured to sit over a flange in a proximal portion of the proximal piece of the intermittent catheter, and wherein the flange includes a gasket thereover configured to sit between the cap and the proximal piece and form a fluidly tight seal when the cap caps the proximal piece.

19. The intermittent-catheter assembly of claim 11, wherein the distal piece of the catheter housing inserted into the receptacle of the cap forms an after-use storage state of the intermittent-catheter assembly configured to prevent urine leakage from the intermittent-catheter assembly after voiding urine therewith.

\* \* \* \* \*